United States Patent
Miyamoto et al.

(10) Patent No.: US 7,972,345 B2
(45) Date of Patent: Jul. 5, 2011

(54) SURGICAL INSTRUMENT

(75) Inventors: Manabu Miyamoto, Hachioji (JP);
Takumi Dejima, Sagamihara (JP);
Kazuo Banju, Hachioji (JP); Shuhei Iizuka, Hamamatsu (JP)

(73) Assignee: Olympus Corporation, Tokyo (JP)

( * ) Notice: Subject to any disclaimer, the term of this patent is extended or adjusted under 35 U.S.C. 154(b) by 1113 days.

(21) Appl. No.: 11/599,543

(22) Filed: Nov. 14, 2006

(65) Prior Publication Data

US 2008/0021499 A1 Jan. 24, 2008

Related U.S. Application Data

(63) Continuation of application No. PCT/JP2005/008482, filed on May 10, 2005.

(30) Foreign Application Priority Data

May 14, 2004 (JP) ................. 2004-145699
Jan. 14, 2005 (JP) ................. 2005-008153

(51) Int. Cl.
*A61B 17/04* (2006.01)
*A61B 17/00* (2006.01)

(52) U.S. Cl. ...................... 606/148; 606/205

(58) Field of Classification Search .............. 606/139, 606/144, 148, 205, 170
See application file for complete search history.

(56) References Cited

U.S. PATENT DOCUMENTS

| | | | |
|---|---|---|---|
| 5,254,130 A | 10/1993 | Poncet et al. | |
| 5,374,277 A | 12/1994 | Hassler | |
| 5,437,682 A * | 8/1995 | Grice et al. | 606/148 |
| 5,951,575 A | 9/1999 | Bolduc et al. | |
| 5,993,466 A | 11/1999 | Yoon | |
| 6,063,098 A * | 5/2000 | Houser et al. | 606/170 |
| 6,224,614 B1 | 5/2001 | Yoon | |
| 2002/0156497 A1 | 10/2002 | Nagase et al. | |

FOREIGN PATENT DOCUMENTS

| | | |
|---|---|---|
| EP | 0 908 141 A1 | 4/1999 |
| JP | 7-505801 | 6/1995 |
| JP | 07-265326 | 10/1995 |
| JP | 08-206120 | 8/1996 |
| JP | 10-192288 | 7/1998 |
| JP | 11-188042 | 7/1999 |
| JP | 2002-253554 | 9/2002 |
| WO | WO 98/57585 | 12/1998 |
| WO | WO 99/65398 | 12/1999 |

* cited by examiner

*Primary Examiner* — Julian W Woo
(74) *Attorney, Agent, or Firm* — Scully, Scott, Murphy & Presser, P.C.

(57) ABSTRACT

A surgical instrument of the present invention comprises an insertion unit; an operating unit provided on one end of the insertion unit; a treatment unit provided so as to protrude from the other end of the insertion unit; a first shaft member for transmitting turning force to the treatment unit in conjunction with the turning operation of a turning operation member provided on the operating unit; and a second shaft member for transmitting opening/closing force to the treatment unit in conjunction with the opening/closing operation of an opening/closing member provided on the operating unit.

12 Claims, 34 Drawing Sheets

SURGICAL INSTRUMENT

CROSS-REFERENCE TO RELATED APPLICATION

This application is a continuation application of PCT/JP2005/008482 filed on May 10, 2005, and claims benefit of Japanese Applications No. 2004-145699 filed in Japan in May 14, 2004, and No. 2005-008153 filed in Japan on Jan. 14, 2005. The entire contents of these applications are incorporated herein by this reference.

BACKGROUND OF THE INVENTION

1. Field of the Invention

The present invention relates to a surgical instrument for grasping a needle and performing tissue anastomosis and so forth under the observation by endoscope.

2. Description of the Related Art

A type of bypass surgery has been known during which coronary artery revascularization of the heart for example is performed using an endoscope, wherein an endoscope, a surgical instrument to be used as a needle-holding device, and forceps and so forth are inserted into the chest cavity via a trocar which punctures the chest wall, an anastomosis opening is created by cutting open a portion of the coronary artery with scissors, the internal thoracic artery is brought to the anastomosis opening with the grasping forceps, and the internal thoracic artery is anastomosed to the anastomosis opening and connected thereto with the surgical instruments.

With such a surgery, U.S. Pat. No. 5,951,575 for example describes a known configuration wherein an insertion unit having a curved portion on the tip portion is provided, and a pair of jaws which can turn about the axis of the insertion unit and which can open and close at the tip portion of the insertion unit are provided, as a surgical instrument which anastomoses tissue particularly by grasping a suture needle. A driving cable for transmitting turning force and opening/closing force to the tip of the insertion unit is passed from the operating unit through the insertion unit to the tip.

Also, USP 2002/156497 discloses a surgical device with a configuration having forceps with a large degree of freedom, which transmits turning force and opening/closing force of the treatment unit with three links.

SUMMARY OF THE INVENTION

The object of the present invention is to provide a surgical instrument of which the operation is facilitated.

The surgical instrument in accordance with a first aspect of the present invention comprises: an insertion unit; an operating unit provided on one end of the insertion unit; a treatment unit provided so as to protrude from the other end of the insertion unit; a first shaft member for transmitting turning force to the treatment unit in conjunction with the turning operation of a turning operation member provided on the operating unit; and a second shaft member for transmitting opening/closing force to the treatment unit in conjunction with the opening/closing operation of an opening/closing member provided on the operating unit; wherein the first shaft member and the second shaft member are positioned on approximately the same axis; and wherein the treatment unit can turn about the axis in the protruding direction according to the turning operation with the turning operation member, and the treatment unit can move at least one of two gripping members, each having a gripping face according to the opening/closing operation with the opening/closing operation member, and so can be opened or closed.

The surgical instrument in accordance with a second aspect of the present invention comprises: an insertion unit; an operating unit provided on one end of the insertion unit; a treatment unit provided so as to protrude from the other end of the insertion unit; a shaft member for both transmitting turning force and transmitting opening/closing force, in conjunction with the turning operation of a turning operation member provided on the operating unit for transmitting turning force to the treatment unit, and in conjunction with the opening/closing operation of an opening/closing member provided on the operating unit for transmitting opening/closing force to the treatment unit; wherein the treatment unit can turn about the axis in the protruding direction according to the turning operation with the turning operation member, and the treatment unit can move at least one of two gripping members, each having a flat face according to the opening/closing operation with the opening/closing operation member, and so can be opened or closed.

The surgical instrument in accordance with a third aspect of the present invention comprises: an insertion unit; an operating unit provided on one end of the insertion unit; a treatment unit provided so as to protrude from the other end of the insertion unit; a first shaft member for transmitting turning force to the treatment unit in conjunction with the turning operation of a turning operation member provided on the operating unit; a second shaft member for transmitting opening/closing force to the treatment unit in conjunction with the opening/closing operation of an opening/closing member provided on the operating unit; and a third shaft member for transmitting angle-variable force which changes the angle in the protruding direction of the treatment unit as to the axis of the insertion unit in conjunction with an angle-variable operation of a angle-variable operating unit provided on the operating unit; wherein the first shaft member, the second shaft member, and the third shaft member are positioned on approximately the same axis; and wherein the treatment unit can turn about the axis in the protruding direction according to the turning operation with the turning operation member, and the treatment unit can move at least one of two gripping members, each having a gripping face according to the opening/closing operation with the opening/closing operation member, and so can be opened or closed, and the treatment unit can change the angle in the protruding direction according to the angle-variable operation with the angle-variable operating unit.

The surgical instrument in accordance with a fourth aspect of the present invention comprises: an insertion unit; an operating unit provided on one end of the insertion unit; a treatment unit provided so as to protrude from the other end of the insertion unit; first shaft means for transmitting turning force to the treatment unit in conjunction with the turning operation of turning operation means provided on the operating unit; and second shaft means for transmitting opening/closing force to the treatment unit in conjunction with the opening/closing operation of opening/closing means provided on the operating unit; wherein the first shaft means and the second shaft means are positioned on approximately the same axis; and wherein the treatment unit can turn about the axis in the protruding direction according to the turning operation with the turning operation means, and the treatment unit can move at least one of two gripping members, each having a gripping face according to the opening/closing operation with the opening/closing operation means, and so can be opened or closed.

The surgical instrument in accordance with a fifth aspect of the present invention comprises: an insertion unit; an operating unit provided on one end of the insertion unit; a treatment unit provided so as to protrude from the other end of the insertion unit; shaft means for both transmitting turning force and transmitting opening/closing force, in conjunction with the turning operation of turning operation means provided on the operating unit for transmitting turning force to the treatment unit, and in conjunction with the opening/closing operation of opening/closing means provided on the operating unit for transmitting opening/closing force to the treatment unit; wherein the treatment unit can turn about the axis in the protruding direction according to the turning operation with the turning operation means, and the treatment unit can move at least one of two gripping members, each having a flat face according to the opening/closing operation with the opening/closing operation means, and so can be opened or closed.

The surgical instrument in accordance with a sixth aspect of the present invention comprises: an insertion unit; an operating unit provided on one end of the insertion unit; a treatment unit provided so as to protrude from the other end of the insertion unit; first shaft means for transmitting turning force to the treatment unit in conjunction with the turning operation of a turning operation means provided on the operating unit; second shaft means for transmitting opening/closing force to the treatment unit in conjunction with the opening/closing operation of opening/closing means provided on the operating unit; and third shaft means for transmitting angle-variable force which changes the angle in the protruding direction of the treatment unit as to the axis of the insertion unit in conjunction with an angle-variable operation of a angle-variable operating unit provided on the operating unit; wherein the first shaft means, the second shaft means, and the third shaft means are positioned on approximately the same axis; and wherein the treatment unit can turn about the axis in the protruding direction according to the turning operation with the turning operation means, and the treatment unit can move at least one of two gripping members, each having a gripping face according to the opening/closing operation with the opening/closing operation means, and so can be opened or closed, and the treatment unit can change the angle in the protruding direction according to the angle-variable operation with the angle-variable operating unit.

The surgical instrument in accordance with a seventh aspect of the present invention comprises: an insertion unit; an operating unit provided on one end of the insertion unit; a treatment unit provided so as to protrude from the other end of the insertion unit; a turning operation member provided on the operating unit for turning the treatment unit about an axis in the protruding direction according to the turning operation; an opening/closing operation member provided on the operating unit to open or close the treatment unit by moving at least one of two gripping members thereof in response to an opening/closing operation input; a first shaft member in a pipe shape provided in the insertion unit for transmitting a first force to turn the treatment unit in conjunction with the turning operation input from the turning operation member; and a second shaft member provided in the insertion unit and inserted within the first shaft member for transmitting a second force to open or close the treatment unit in conjunction with the opening/closing operation input from the opening/closing operation member.

The surgical instrument in accordance with a eighth aspect of the present invention comprises: an insertion unit; an operating unit provided on one end of the insertion unit; a treatment unit provided so as to protrude from the other end of the insertion unit; a turning operation member provided on the operating unit for turning the treatment unit about an axis in the protruding direction according to the turning operation; an opening/closing operation member provided on the operating unit to open or close the treatment unit by moving at least one of two gripping members thereof in response to an opening/closing operation input; and a shaft member for transmitting a first force to turn the treatment unit in conjunction with the turning operation input from the turning operation member and transmitting a second force to open or close the treatment unit in conjunction with the opening/closing operation input from the opening/closing operation member.

The surgical instrument in accordance with a ninth aspect of the present invention comprises: an insertion unit; an operating unit provided on one end of the insertion unit; a treatment unit provided so as to protrude from the other end of the insertion unit; a first operation member provided on the operating unit for turning the treatment unit about an axis in the protruding direction according to the turning operation; a second operation member provided on the operating unit to open or close the treatment unit by moving at least one of two gripping members thereof in response to an opening/closing operation; a third operation member provided on the operating unit for changing the angle in the protruding direction of the treatment unit as to the axis of the insertion unit in response to an angle-variable operation; a first shaft member in a pipe shape for transmitting a first force to turn the treatment unit in conjunction with the turning operation input from the first operation member; a second shaft member inserted within the first shaft member for transmitting a second force to open or close the treatment unit in conjunction with the opening/closing operation input from the second operation member; and a third shaft member in a pipe shape which is provided in the insertion unit and within which the first shaft member is inserted, for transmitting a third force to change the angle in conjunction with an angle-variable operation input from the third operation member.

The surgical instrument in accordance with a tenth aspect of the present invention comprises: an insertion unit; an operating unit provided on one end of the insertion unit; a treatment unit provided so as to protrude from the other end of the insertion unit; turning operation means provided on the operating unit for turning the treatment unit about an axis in the protruding direction according to the turning operation; opening/closing operation means provided on the operating unit to open or close the treatment unit by moving at least one of two gripping members thereof in response to an opening/closing operation input; first shaft means in a pipe shape provided in the insertion unit for transmitting a first force to turn the treatment unit in conjunction with the turning operation input from the turning operation means; and second shaft means provided in the insertion unit and inserted within the first shaft means for transmitting a second force to open or close the treatment unit in conjunction with the opening/closing operation input from the opening/closing operation means.

The surgical instrument in accordance with a eleventh aspect of the present invention comprises: an insertion unit; an operating unit provided on one end of the insertion unit; a treatment unit provided so as to protrude from the other end of the insertion unit; turning operation means provided on the operating unit for turning the treatment unit about an axis in the protruding direction according to the turning operation; opening/closing operation means provided on the operating unit to open or close the treatment unit by moving at least one of two gripping members thereof in response to an opening/closing operation input; and shaft means for transmitting a first force to turn the treatment unit in conjunction with the turning operation input from the turning operation means and transmitting a second force to open or close the treatment unit in conjunction with the opening/closing operation input from the opening/closing operation means.

The surgical instrument in accordance with a twelfth aspect of the present invention comprises: an insertion unit; an operating unit provided on one end of the insertion unit; a treatment unit provided so as to protrude from the other end of the insertion unit; first operation means provided on the operating unit for turning the treatment unit about an axis in the protruding direction according to the turning operation; second operation means provided on the operating unit to open or close the treatment unit by moving at least one of two gripping members thereof in response to an opening/closing operation; third operation means provided on the operating unit for changing the angle in the protruding direction of the treatment unit as to the axis of the insertion unit in response to an angle-variable operation; first shaft means in a pipe shape for transmitting a first force to turn the treatment unit in conjunction with the turning operation input from the first operation means; second shaft means inserted within the first shaft means for transmitting a second force to open or close the treatment unit in conjunction with the opening/closing operation input from the second operation means; and third shaft means in a pipe shape which is provided in the insertion unit and within which the first shaft means is inserted, for transmitting a third force to change the angle in conjunction with an angle-variable operation input from the third operation means.

DESCRIPTION OF THE PREFERRED EMBODIMENTS

Embodiments of the present invention will now be described with reference to the drawings.

First Embodiment

Figure 1:
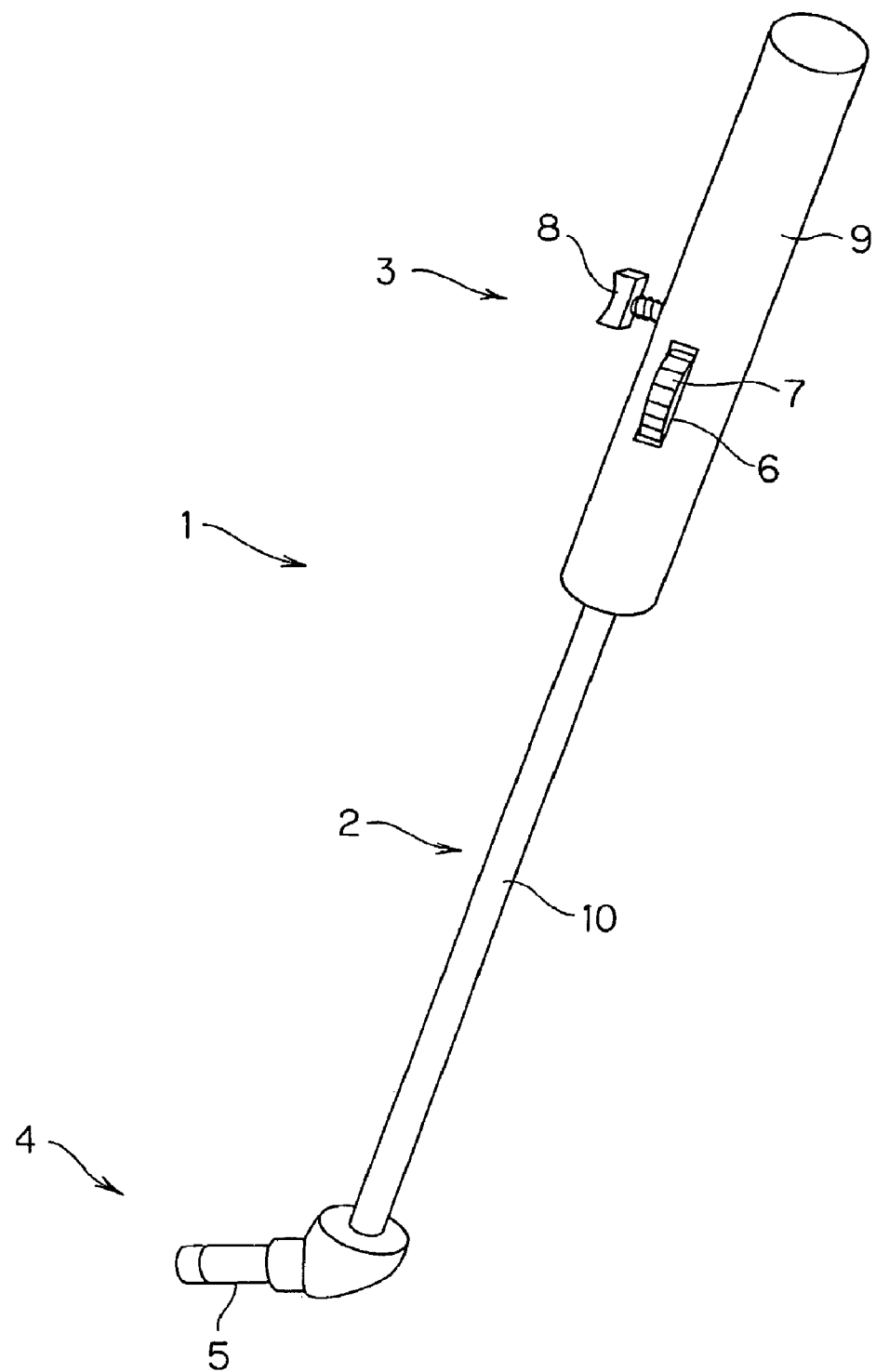
FIG. 1 is a perspective view of a needle driver according to a first embodiment of the present invention.
Figure 2:
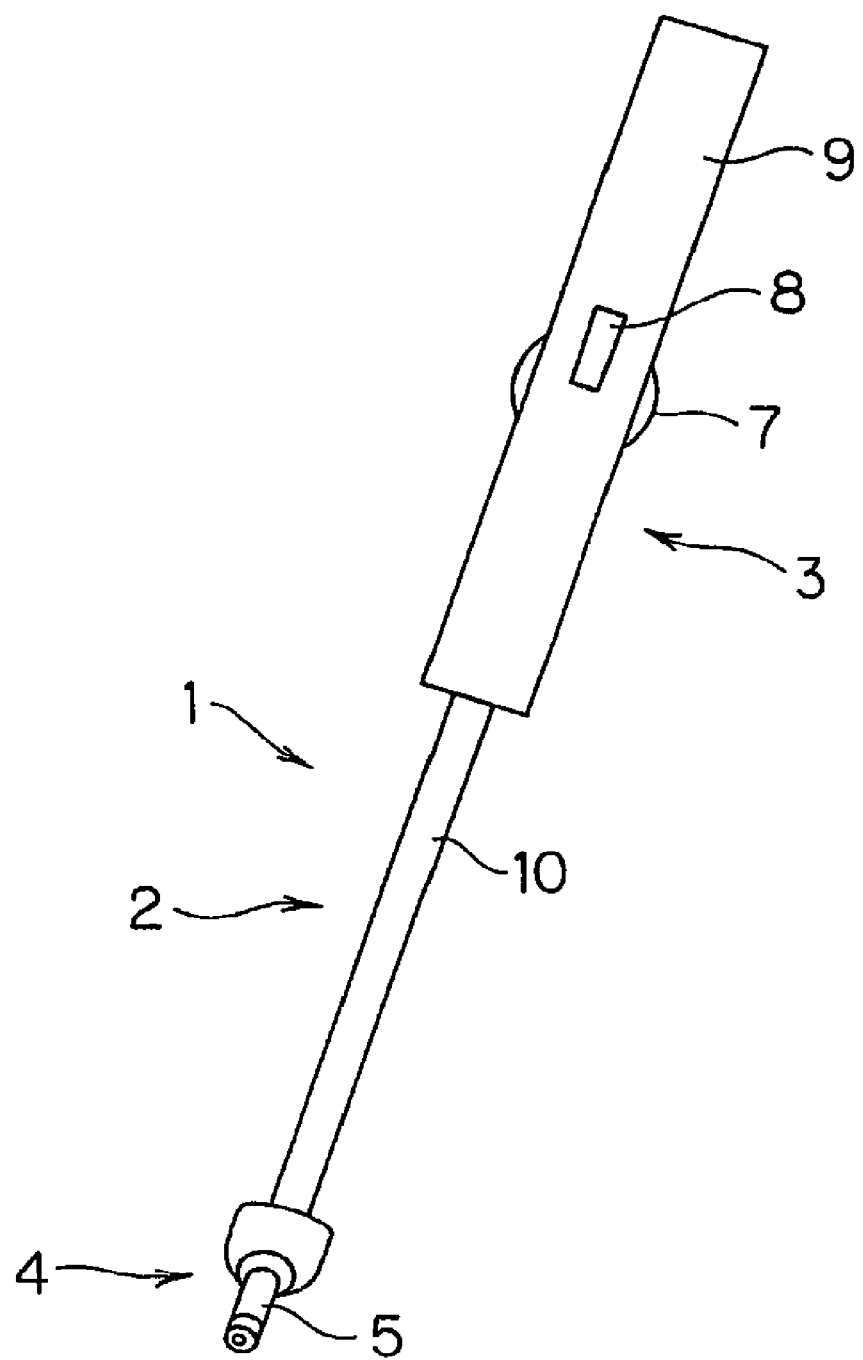
FIG. 2 is a plan view of a needle driver according to the first embodiment of the present invention.
Figure 3:
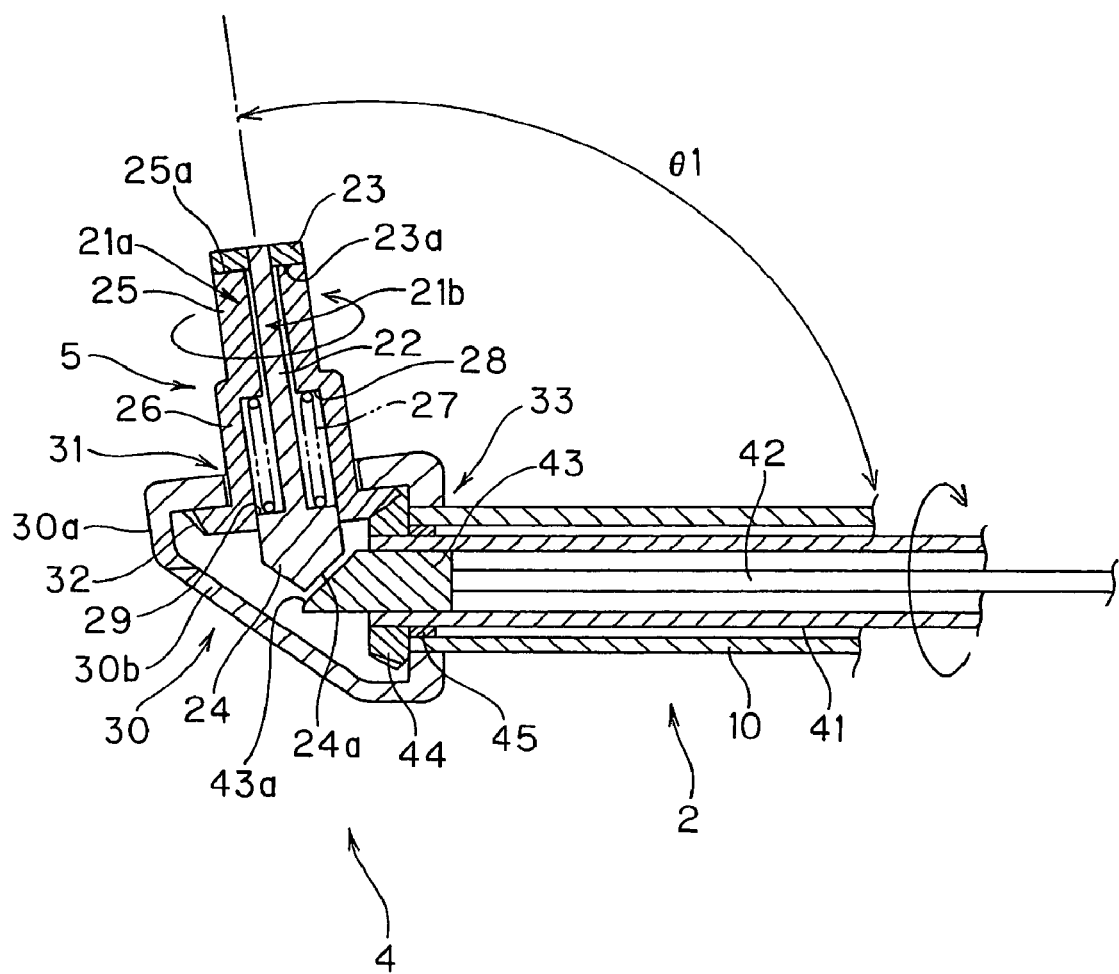
FIG. 3 is a cross-sectional view of a tip portion, including a treatment unit, of a needle driver according to the first embodiment of the present invention.
Figure 4:
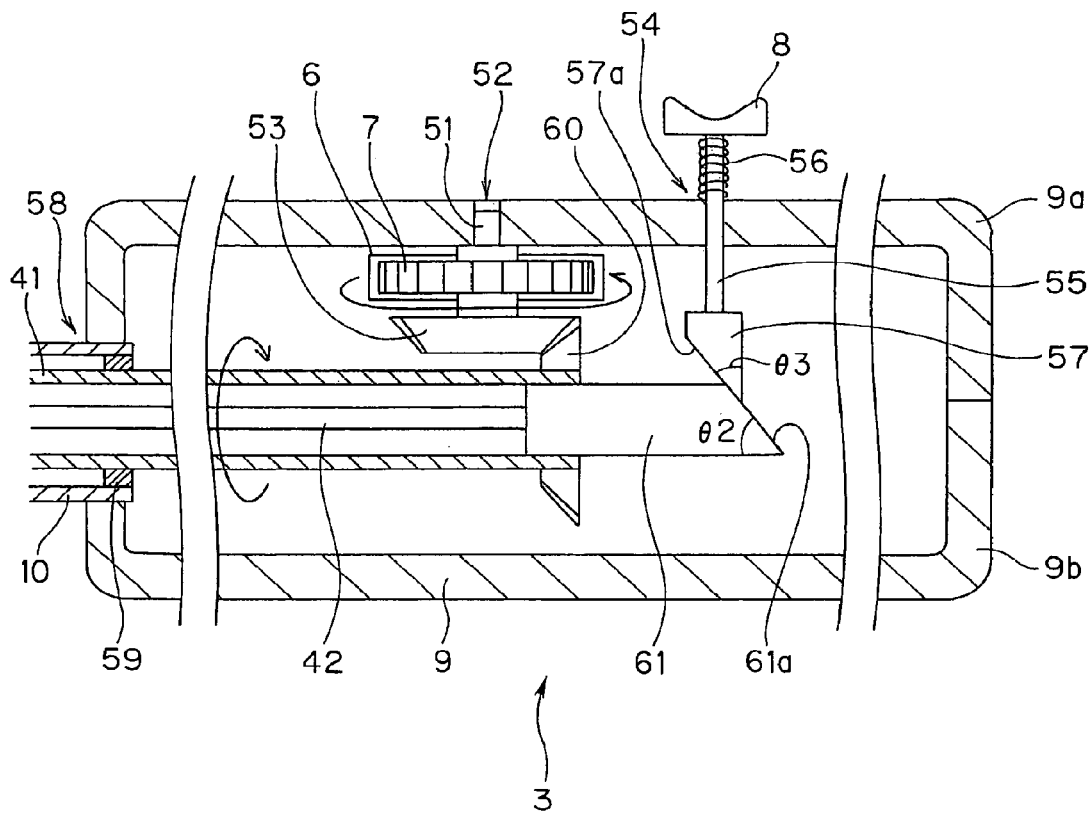
FIG. 4 is a cross-sectional view of a base end portion, including an operating unit, of a needle driver according to the first embodiment of the present invention.
Figure 5:
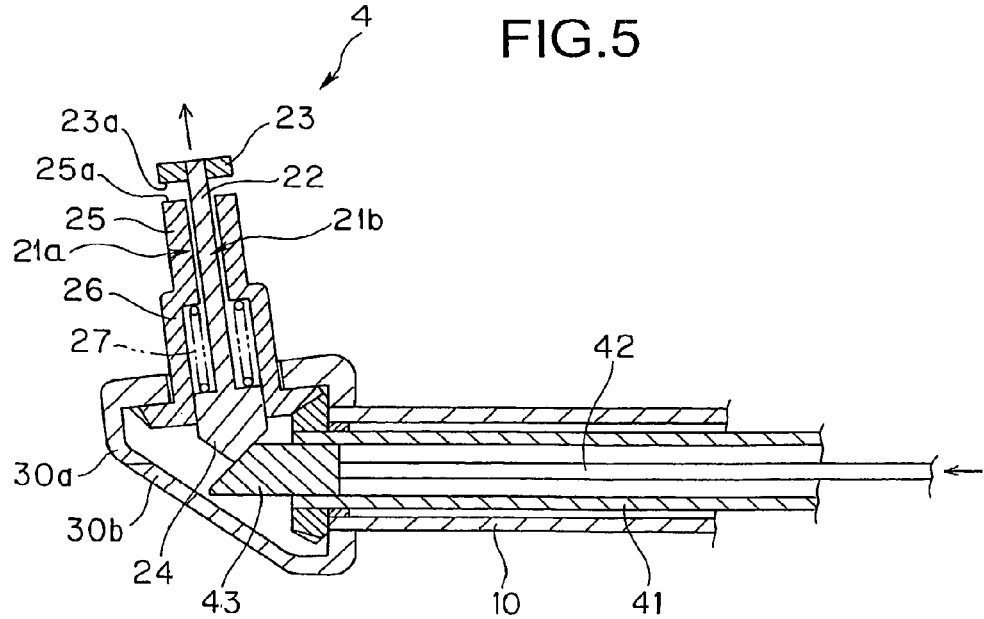
FIG. 5 is a cross-sectional view of the tip portion, showing a state wherein a gripping unit of the treatment unit is open, of a needle driver according to the first embodiment of the present invention.
Figure 6:
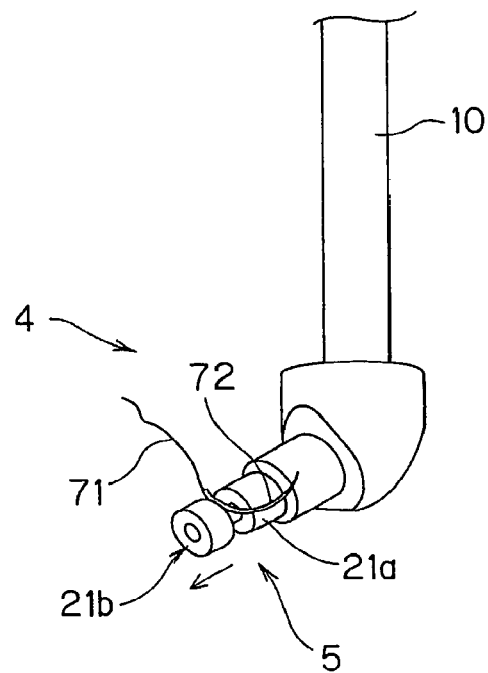
FIG. 6 is a diagram for describing the operation for opening the gripping unit on the treatment unit for gripping a needle.
Figure 7:
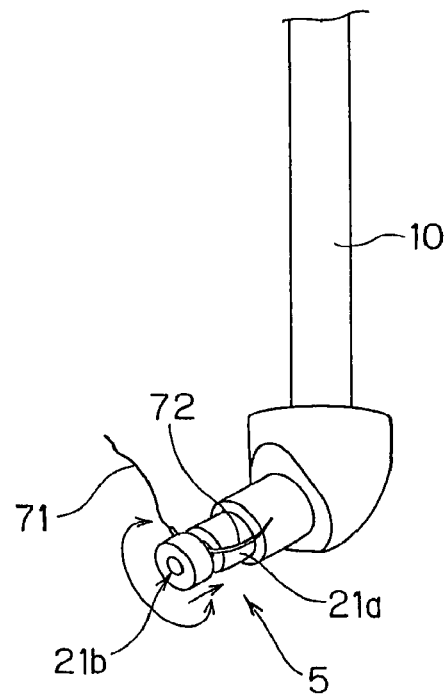
FIG. 7 is a diagram for describing the operation for gripping and turning a needle.

FIGS. 1 through 5 are diagrams for describing the configuration of a needle driver which is a surgical instrument used as a needle-holding device relating to a first embodiment of the present invention. First, the external configuration of the needle driver will be described with reference to FIGS. 1 and 2. FIG. 1 is a perspective view of the needle driver relating to the present embodiment, FIG. 2 is a plan view of the needle driver relating to the present embodiment, FIG. 3 is a cross-sectional view of a tip portion, including a treatment unit 4, of a needle driver 1 relating to the present embodiment, FIG. 4 is a cross-sectional view of a base end portion, including an operating unit 3, of the needle driver 1 relating to the present embodiment, FIG. 5 is a cross-sectional view of the tip portion, showing a state wherein a gripping unit of the treatment unit is open, of the needle driver relating to the present embodiment, FIG. 6 is a diagram for describing the operation for opening the gripping unit on the treatment unit for gripping a needle, and FIG. 7 is a diagram for describing the operation for gripping and turning a needle.

The needle driver 1 comprises an insertion unit 2, an operating unit 3 provided on the base end of the insertion unit 2, and a treatment unit 4 provided on the tip of the insertion unit 2. With the present embodiment, the insertion unit 2 is cylindrical and slender, and has a predetermined length. The operating unit 3 is cylindrical, having an axis which matches the axis of the insertion unit 2, and is in a shape so that the surgeon can grasp the unit with one hand and perform the operations to be described later. The treatment unit 4 is provided so as to protrude in the protruding direction of a predetermined angle as to the axis direction of the insertion unit 2. The treatment unit 4 has a gripping unit 5. On the operating unit 3 is provided a turning dial 7, which is a turning operation member provided such that one portion thereof protrudes from an oblong hole 6, and a opening/closing button 8 which is an opening/closing operation device. The oblong hole 6 is provided in two places on the operating unit 3, and a portion of the turning dial 7 protrudes from each of the oblong holes 6. The turning dial 7 and the opening/closing button 8 are formed of resin or metal. The opening/closing button 8 is pressed by the pressing force of an elastic member, from the front face of the operating unit 3, towards the outer diameter direction, as will be described later, and the opening/closing button 8 is pressed in the direction that is separated from the circumferential face of the operating unit 3. The operating unit 3 has an operating unit cover 9, which is made of resin. Also, the insertion unit 2 is covered by a metallic sheath 10 such as stainless steel.

First, the configuration of the tip portion which includes the treatment unit 4 of the needle driver 1 will be described with reference to FIG. 3.

The treatment unit 4 provided on the tip portion of the insertion unit 2 includes two gripping members 21a and 21b (hereafter, together these may be called 21) which constitutes the gripping unit 5. The first gripping member, 21b which is one of the two gripping members 21 comprises a shaft member 22 which is made of stainless steel, and a ring member 23 which is a gripping ring. The ring member 23 is made of stainless steel. The tip portion of the shaft member 22 is inserted through a hole in the ring member 23, and is affixed firmly to the ring member 23 by means such as welding. On the other end on the opposite side from the tip portion of the shaft member 22, a cylinder unit 24 with a diameter greater than the diameter of the shaft member 22 is formed, which has a cone-shaped wedge-receiving unit 24a.

The second gripping member 21a which is the other of the two gripping members 21 is cylindrical and is made of stainless steel, and has a first tube unit 25 through which the shaft member 22 can slide, and a second tube unit 26 of which the inner diameter is greater than that of the tube unit 25. A coil spring 27 made of stainless steel is arranged within the second tube unit 26, and one end of the coil spring is in contact with a step portion 28 which is in between the first tube unit 25 and the second tube unit 26, and the other end is in contact with a step portion 29 which is between the shaft member 22 and the cylinder unit 24, and also the coil spring 27 is arranged within the second gripping member 21a such that the shaft member 22 is inserted through the coil spring 27. In other words, the step portions 28 and 29 are each spring receptacles. Further, the coil spring 27 is disposed within the second gripping member 21a in a compressed state. Accordingly, the coil spring 27 constitutes a pressing member, that is, a biasing member, which presses, that is, biases, at least one of the two gripping members 21 in the direction of making constant contact as to the other.

The treatment unit 4 has a tip cover 30, and the tip cover 30 comprises a first tip cover 30a and a second tip cover 30b. The first tip cover 30a and the second tip cover 30b are made of resin. On the inner side of the first tip cover 30a and the second tip cover 30b, a space is formed such that a portion of the treatment unit 4 can be arranged within. Further, a hole 31 is formed on the first tip cover 30a so that the treatment unit 4 protrudes as to the axis direction of the insertion unit 2, with a predetermined angle θ1. The cone-shaped tip portion of the wedge-receiving unit 24a is positioned within the tip cover 30.

The base end portion of the second tube unit 26 has a flange portion which protrudes in the circumferential direction, and a bevel gear formed with multiple teeth is formed on the outer circumference portion of the flange portion. Accordingly, the base end portion of the second tube unit 26 comprises the bevel gear member 32. The two gripping members 21 is provided within the space formed within first tip cover 30a and the second tip cover 30b, so that the flange portion of the bevel gear member 32 is in contact with the inner side of the hole 31. The gripping unit 5 can turn while sliding inside the hole 31. Now, the flange portion is to serve a retaining function.

In a state wherein the first tip cover 30a and the second tip cover 30b are fit together, a sheath mounting hole 33 is formed on the tip cover 30. A cylindrical stainless steel pipe member (hereafter called a turning force transmitting member) 41, which is the first shaft member and which can turn about the axis of the insertion unit 2, is inserted through a sheath 10 of the insertion unit 2. The tip portion of the sheath 10 passes through the sheath mounting hole 33 and is affixed to the tip cover 30. Further, on the inner side of the turning force transmitting member 41 which is a pipe shape, a stainless steel opening/closing force transmitting rod 42 which is the second shaft member is inserted with the same axis as the turning force transmitting member 41. In other words, a turning force transmitting member 41, through which the opening/closing force transmitting rod 42 is inserted, is inserted through the sheath 10, and each of the end portions extend to the operating unit 3 and the treatment unit 4. A stainless steel wedge member 43 is affixed to the tip portion of the treatment unit 4 side of the opening/closing force transmitting rod 42. The wedge member 43 is provided so as to be able to slide in the axis direction within the turning force transmitting member 41.

A ring-shaped bevel gear member 44 is affixed on the outer circumference portion of the tip portion of the treatment unit 4 side of the turning force transmitting member 41. The bevel gear member 44 is made of stainless steel or resin. The positions of the bevel gear member 44 and the bevel gear member 32 are determined so as to have the teeth of the bevel gear member 44 and the teeth of the bevel gear member 32 mesh, and are positioned within the space formed within the first tip cover 30a and the second tip cover 30b. The form of each of the bevel gear members are designed so that the treatment unit 4 is at the predetermined angle θ1 as to the axis direction of the insertion unit 2, in the state wherein the teeth of the bevel gear member 44 and the teeth of the bevel gear member 32 mesh. Also, the outer diameter of the bevel gear member 44 is greater than the outer diameter of the sheath 10, and thus the bevel gear member 44 is arranged so as not to pull out of the tip cover 30.

Also, a ring member 45 which is a sliding bearing, formed of a resin or the like which slides well, is provided in between the sheath 10 and the turning force transmitting member 41, so that the turning force transmitting member 41 can turn within the sheath 10.

On the tip portion of the wedge member 43, a sloping portion is formed which has a sloping face 43a having a predetermined angle as to the axis of the insertion unit 2. The wedge member 43 and the first gripping member 21b have the positions determined so that the sloping face 43a and the sloping face 24a face one another. When the rod-shaped opening/closing force transmitting rod 42 is moved towards the tip portion direction of the insertion unit 2 according to the opening/closing operation of an opening/closing button 8 as will be described later, the sloping face 43a of the sloping portion of the wedge member 43 provided on the tip portion of the opening/closing force transmitting rod 42 presses against the wedge-receiving unit 24a of the first gripping member 21b, and thus the first gripping member 21b is moved in the direction which is the axis direction of the first gripping member 21b and wherein the ring member 23 moves away from the first tube unit 25.

The contact faces 23a and 25a which respectively make contact with the ring member 23 of the fist gripping member 21b and the first tube unit 25 of the gripping member 21a have been subjected to slip-resistant processing so that the gripped needle does not slip, and a needle can be fixed with certainty when the needle is gripped. The slip-resistant processing can be slip-resistant processing by electrical discharge, or it can be processing wherein knurling is performed on each contact face. Furthermore, the processing can be such that the surface is plated with metal, and a powder of particles with a high degree of hardness such as diamond or sapphire is embedded into the metal plating.

Also, the treatment unit 4 is extended in the direction approximately orthogonal as to the flat face of the contact faces of the ring member 23 and the first tube unit 25 which grip the needle, and in the direction at a predetermined angle θ1 as to the axis direction of the insertion unit 2.

Next, the configuration of the operating unit 3 of the needle driver 1 will be described.

The operating unit 3 is in an overall cylindrical shape, and has an operating unit cover 9 which is formed of a first operating unit cover 9a and a second operating unit cover 9b, each of which has a cross-sectional shape of a semicircle. The operating unit cover 9 is provided so as to cover the base end portion of the insertion unit 2 with the tip portion of the operating unit 3. The operating unit cover 9a and the second operating unit cover 9b are fastened to each other by unshown fastening members such as screws or the like. The first operating unit cover 9a and the second operating unit cover 9b are formed of a resin such as plastic.

The shaft member 51 which is provided in the orthogonal direction as to the axis of the operating unit 3 is inserted in the axis-receiving hole 52 provided on the operating unit cover 9, so as to be able to turn. The shaft member 51 has a turning dial 7 affixed thereto, for the purpose of functioning as a turning shaft member of the turning dial 7 as a turning wheel. The shaft member 51 also has a bevel gear member 53 affixed thereto. The turning dial 7 is formed of metal such as aluminum, or of plastic, and as shown in FIGS. 1 and 2, is a flat circular member having a diameter which protrudes from the oblong hole 6 of the operating unit 3. A processing such as knurling for slip-resistance is performed on the circumferential face of the turning dial 7.

The operating unit cover 9 has a button hole 54 formed thereupon; and a metal rod member 55 is inserted through the button hole 54 as a pushing rod. The opening/closing button 8 which is made of plastic or a metal such as aluminum is affixed to the tip portion of the rod member 55, on the outside of the tip cover 9. Also, the opening/closing button 8 has an approximately rectangular shape, and the face on the opposite side from the operating unit cover 9, that is to say, the face on which the surgeon places a finger, has a slightly concave shape. In between the face on the operating unit cover 9 side of the opening/closing button 8 and the circumferential face of the operating unit cover 9, a stainless steel coil spring 56 as an elastic member is arranged so that the rod member 55 passes through the coil spring 56. Thus, the opening/closing button 8 is constantly pressed in the direction separated from the operating unit cover 9.

Also, a wedge member 57 made of a metal such as stainless steel is affixed to the tip portion on the inner side of the operating unit cover 9 of the rod member 55, and when the opening/closing button 8 is pressed in by the surgeon finger, the wedge member 57 also moves in the direction of being pressed.

In a state wherein the operating unit cover 9a and the operating unit cover 9b are fit together, a sheath mounting hole 58 is formed on the tip side of the operating unit cover 9. The sheath 10 is affixed to the operating unit cover 9 through this sheath mounting hole 58. On the base end side of the insertion unit 2 also, a ring member 59 which is a sliding bearing made of a resin which slides well is provided between the sheath 10 and the turning force transmitting member 41, so that the turning force transmitting member 41 can turn within the sheath 10. The turning force transmitting member 41 is extended to the inner portion of the operating unit 3, and within the operating unit 3, a ring-shaped bevel gear member 60 is provided on the outer circumference portion of the base end side of the turning force transmitting member 41. The positions of the bevel gear member 60 and the bevel gear member 53 are determined so as to have the teeth of the bevel gear member 60 and the teeth of the bevel gear member 53 mesh, and are positioned within the space formed within the operating unit cover 9a and the operating unit cover 9b. The bevel gear member 60 and the bevel gear member 53 are formed of stainless steel or of resin. With the bevel gear member 60 and the bevel gear member 53, the turning direction of the turning dial 7 is changed to the turning direction on the turning axis of the turning transmitting member 41 which is orthogonal to the turning axis of the turning dial 7. Also, the opening/closing force transmitting rod 42 also extends to the inner portion of the operating unit 3.

A wedge member 61 is affixed to the base end portion of the operating unit 3 side of the opening/closing force transmitting rod 42 which is inserted within the turning force transmitting member 41. The wedge member 61 is provided so as to be slidable in the axis direction within the turning force transmitting member 41.

The wedge member 61 is configured such that a sloping portion which has a sloping face 61a having a predetermined angle θ2 as to the axis of the insertion unit 2 is formed on the tip portion of the base end side of the operating unit 3. The desired angle of the predetermined angle θ2 is for example equal to or more than 45 degrees. The wedge member 57 is configured such that a sloping portion which has a sloping face 57a having a predetermined angle θ3 as to the axis direction of the rod member 55 is formed on the tip portion thereof. Also, within the operating unit cover 9, the positions of the wedge member 57 and the wedge member 61 are determined so that the sloping face 57a and the sloping face 61a face one another in a parallel state. When the opening/closing button 8 is pressed, the rod member 55 is moved so as to press the wedge member 57 against the wedge member 61. When the sloping face 57a of the wedge member 57 moves while sliding along the surface of the sloping face 61a, the wedge member 61 moves the opening/closing force transmitting rod 42 to the treatment unit 4 side along the axis direction of the insertion unit 2.

When the opening/closing force transmitting rod 42 moves in the direction of the tip portion of the insertion unit 2, the sloping face 43a of the sloping portion of the wedge member 43 provided on the tip portion of the opening/closing force transmitting rod 42 presses against the wedge-receiving unit 24a of the first gripping member 21b, and so the first gripping member 21b moves in the axis direction of the first gripping member 21b which is the direction in which the ring member 23 moves away from the first tube unit 25.

Also, the positions of the bevel gear member 60 and the bevel gear member 53 are determined so as to have the teeth of the bevel gear member 60 and the teeth of the bevel gear member 53 mesh, and are positioned within the space formed within the operating unit cover 9a and the operating unit cover 9b. Accordingly, when the surgeon turns the turning dial 7 with a finger, the turning force turns the turning force transmitting member 41 about the axis of the insertion unit 2, via the bevel gear members 53 and 60. The turning force of the turning force transmitting member 41 turns the second gripping member 21a about the axis of the extension direction of the treatment unit 4, via the bevel gear members 44 and 32. At this time, the ring member 23 of the first gripping member 21b is in close contact with the second gripping member 21a so as to be pressed together with the coil spring 27, and thus the turning force of the turning force transmitting member 41 turns gripping members 21a and 21b of the gripping unit 5 together.

Next, the actions of the needle driver 1 according to the above-described configuration will be described. When the surgeon turns the turning dial 7, the turning force turns the turning force transmitting member 41 about the axis, with the two bevel gear members 53 and 60. The turning of the turning force transmitting member 14 turns the gripping unit 5 about the axis in the extension direction, with the two bevel gear members 44 and 32. Accordingly, the surgeon can turn the gripping unit 5 with the turning operation of the turning dial 7. In other words, the two gripping members 21 turn with the axis in the extension direction of the treatment unit 4 as the center, in conjunction with the turning of the turning dial 7.

Further, when the opening/closing button 8 is pressed down with a finger, the wedge member 61 is moved toward the treatment unit 4 side while sliding along each of the sloping faces from the movement of the wedge member 52. As a result, the opening/closing force transmitting rod 42 advances to the tip portion side, in conjunction with the opening operation of the opening/closing button 7, as shown in FIGS. 5 and 6, while sliding along the sloping face 43a of the wedge member 43 and the wedge-receiving portion 24a. As a result, the wedge member 43 slides the first gripping member 21b in the extension direction, and a gap is formed in between the first gripping member 21b and the second gripping member 21a.

In this state, as shown in FIG. 6, the base end of a needle 72 made of a metal such as stainless steel provided with a thread 71 which is formed of polypropylene or the like is positioned in this gap, and the opening/closing button 8 is released. Then the coil spring 27 is pressed so that the space between the first gripping member 21b and the second gripping member 21a is closed, and thus the retaining of the needle 72 can be maintained by this pressing force.

In other words, in conjunction with the opening/closing operation of the opening/closing button 8, the opening/closing force transmitting rod 42 advances or retreats and the opening/closing force is transmitted to the treatment unit 4. Then, only when the surgeon opens the first gripping member 21b and second gripping member 21a, pressure is applied to the opening/closing button 8 resisting the pressing force of the coil spring 27, but in the state wherein the first gripping member 21b and second gripping member 21a are closed, this state is maintained by the pressing force, and so the surgeon does not need to operate the opening/closing button 8, and can perform other operations, for example operating the turning dial 7. In other words, when the turning dial 7 is turned with the finger, this turning force is transmitted to the treatment unit 4, and as shown in FIG. 7, the needle 72 can be turned about the axis of the treatment unit 4 in the state that the needle 72 is retained. According to the above-described configuration, there is no limit to the turning angle in the state that the needle 72 is gripped by the gripping unit 5.

Thus, according to the surgical instrument in the present embodiment, opening/closing force is transmitted to the gripping unit 5 by the rod member, and the turning force is transmitted to the gripping unit 5 by the pipe member arranged on approximately the same axis as the rod member. Particularly, the gripping unit 5 is maintaining the gripping state independently without force applied from the outside, and therefore, there is no need to perform a turning operation while maintaining gripping force as has been with the conventional case. Thus, the surgeon can easily perform a turning operation in the state of gripping a gripped object such as a needle with the gripping unit 5, and this is extremely easy to use. The surgeon can focus on the turning of the gripped objects or other operations. Further, a rod member is arranged on approximately the same axis as the pipe member, and so space is conserved, and therefore the insertion unit 2 is made with a smaller diameter, and becomes easier to use with the reasons to be described later.

Accordingly, according to the present embodiment, a needle driver with good operational functionality can be realized with a simple configuration.

Second Embodiment

FIGS. 8 through 12 are diagrams for describing the configuration of a needle driver relating to a second embodiment of the present invention. Where components are the same as the first embodiment, the same reference numerals are used and the description thereof is omitted, and primarily only different components will be described. The present embodiment has a turning/opening/closing force transmitting member 142 which combines the functionality of both the turning force transmitting member 41 and the opening/closing force transmitting rod 42, instead of having the turning force transmitting member 41 and the opening/closing force transmitting rod 42 in the above-described first embodiment.

Figure 8:
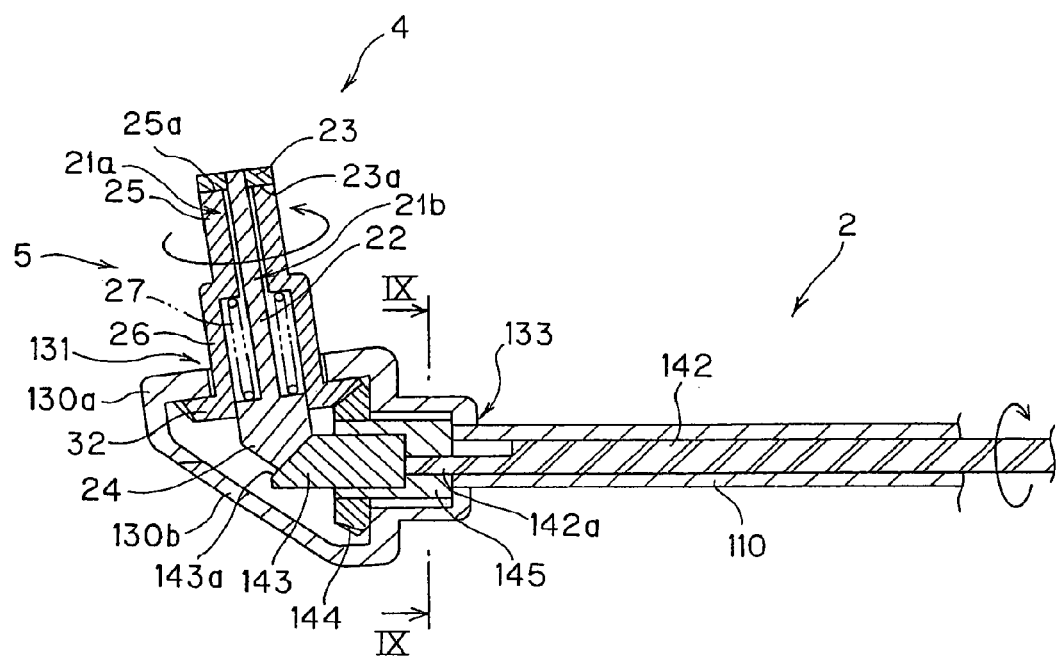
FIG. 8 is a cross-sectional view of a tip portion, including a treatment unit, of a needle driver according to a second embodiment of the present invention.
Figure 9:
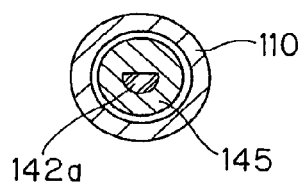
FIG. 9 is a cross-sectional view along the IX-XI line in FIG. 8.
Figure 10:
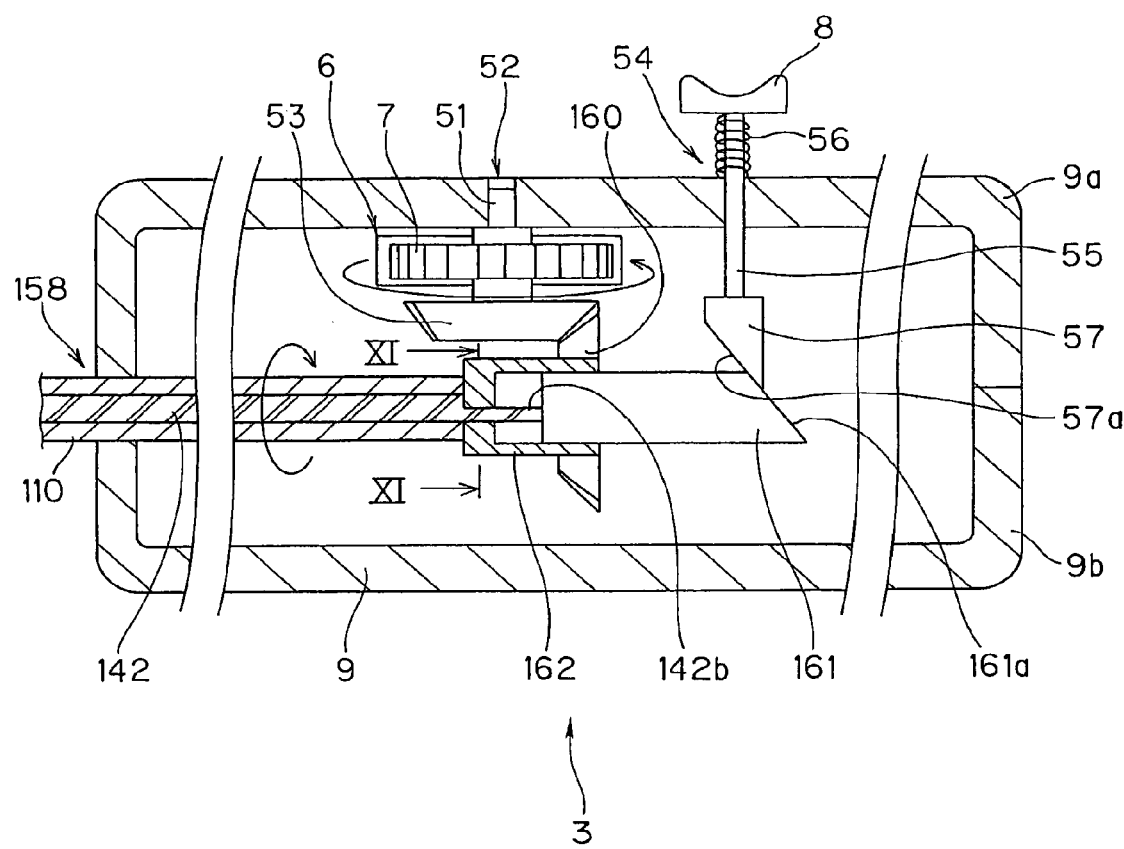
FIG. 10 is a cross-sectional view of a base end portion, including an operating unit, of a needle driver according to the second embodiment of the present invention.
Figure 11:
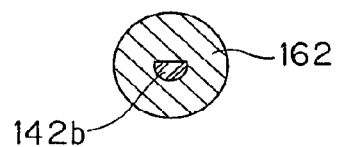
FIG. 11 is a cross-sectional view along the XI-XI line in FIG. 10.
Figure 12:
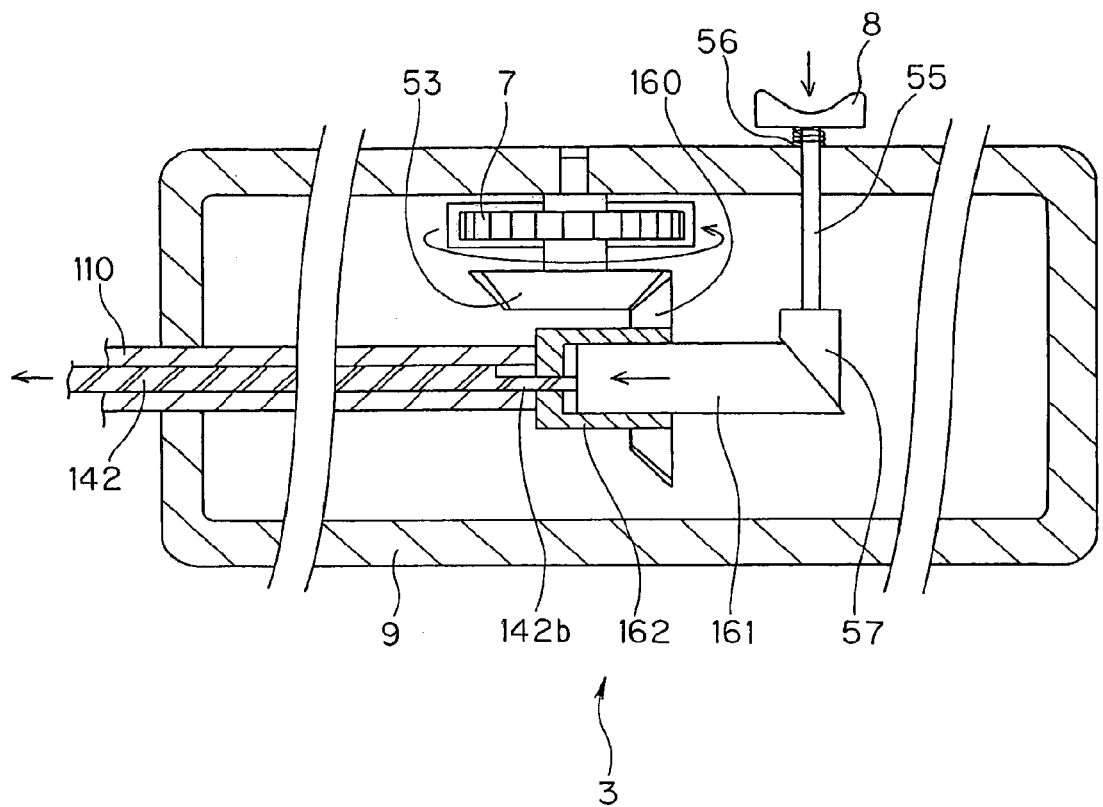
FIG. 12 is a cross-sectional view of a base end portion, including an operating unit, of a needle driver according to the second embodiment of the present invention.
Figure 13:
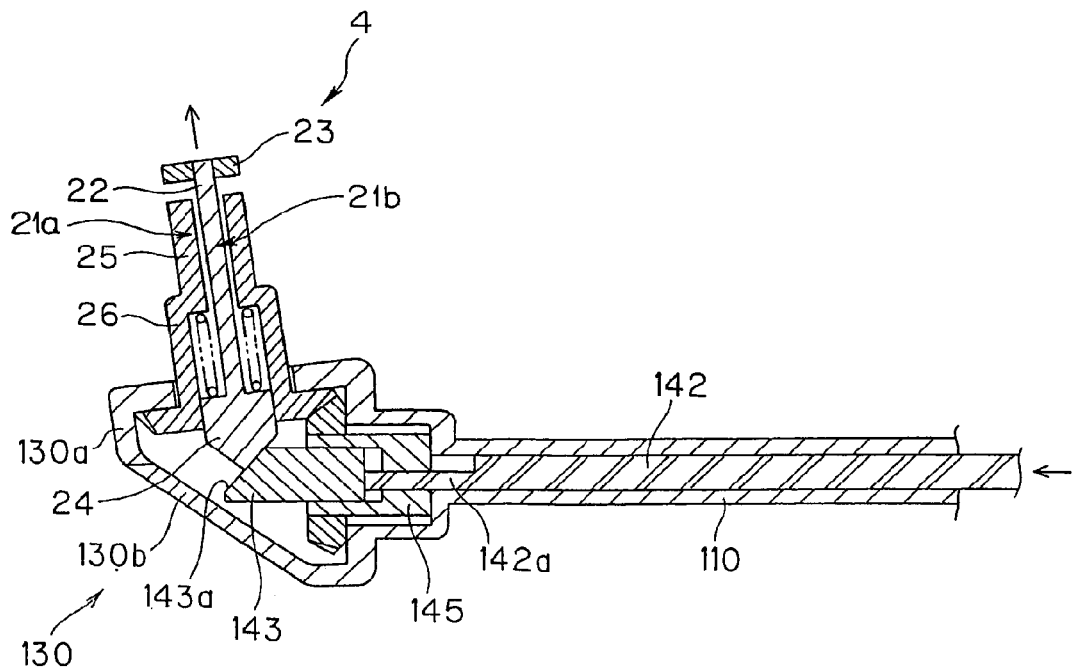
FIG. 13 is a cross-sectional view of the tip portion, showing a state wherein a gripping unit of the treatment unit is open, of a needle driver according to the second embodiment of the present invention.

FIG. 8 is a cross-sectional view of the tip portion including the treatment unit 4 of the needle driver 1 relating to the present embodiment, FIG. 9 is a cross-sectional view along the IX-XI line in FIG. 8, FIG. 10 is a cross-sectional view of the base end portion, including the operating unit 3 of the needle driver 1 according to the present embodiment. FIG. 11 is a cross-sectional view along the XI-XI line in FIG. 10, FIG. 12 is a cross-sectional view of the base end portion including the operating unit of a needle driver at the time of the operation for opening the treatment unit for the purpose of gripping the needle, and FIG. 13 is a cross-sectional view of the tip portion, showing a state wherein the gripping unit of the treatment unit of the needle driver is open.

The insertion unit 2 is covered by a sheath 110 made of a metal such as stainless steel. A rod member 142 passes through the inner side of the sheath 110 as a shaft member, as will be described below.

The treatment unit 4 has a tip cover 130, and the tip cover 130 is formed of a first tip cover 130a and a second tip cover 130b. On the inner side of the first tip cover 130a and the second tip cover 130b, a space is formed so as to be able to arrange a portion of the treatment unit 4. Further, a hole 131 is formed on the first tip cover 130a, so that the treatment unit 4 protrudes with a predetermined angle θ1 as to the axis direction of the insertion unit 2. The tip portion of the cone-shaped wedge-receiving unit 24a is positioned within the tip cover 30.

The base end portion of the second tube unit 26 has a flange portion which protrudes in the circumferential direction, and a bevel gear formed with multiple teeth is formed on the outer circumference portion of the flange portion. Accordingly, the flange portion of the bevel gear member 32 is provided so as to be in contact with the inner side of the hole 131 within the space formed within the first tip cover 130a and the second tip cover 130b.

In a state wherein the first tip cover 130a and the second tip cover 130b are fit together, a sheath mounting hole 133 is formed on the tip cover 130. A shaft member which can turn about the axis of the insertion unit 2, and which can slide in the axis direction of the insertion unit 2 (hereafter called a turning/opening/closing force transmitting member) 142, is inserted through a sheath 110 of the insertion unit 2. The tip portion of the sheath 110 passes through the sheath mounting hole 133 and is mounted and affixed to the tip cover 130. On the inner portion of the tip cover 130, a turning-receiving member 145 cannot move in the axis direction, but is stored so as to be able to turn in the axis direction. Here, the turning/opening/closing force transmitting member 142 is a rod member.

The turning-receiving member 145 is formed of stainless steel or resin, is in a cylindrical shape, and has a bottom face. A stainless, steel turning/opening/closing force transmitting member 142 has a D-shape portion 142a of a predetermined length in the axis direction, wherein the cross-sectional shape is a semi-circle, as shown in FIG. 9, on the tip portion of the treatment unit 4 side. The D-shape portion 142a is inserted in the tip side, so as to be slidable as to the D-shape hole provided on the bottom face portion of the turning-receiving member 145. The D-shape portion 142a has at least one flat face portion wherein the cross-sectional shape of the face which is orthogonal to the axis direction of the turning/opening/closing force transmitting member 142 is a straight line. The D-shape hole has at least one flat face portion wherein the cross-sectional shape of the face orthogonal to the direction of the hole is a straight line, and the flat face portion thereof is formed so as to face with the flat face portion of the D-shape portion 142a.

The cylindrically shaped turning-receiving member 145 has an opening portion on the opposite side from the insertion unit 2 side, and so a concave portion is formed on the tip side, and a wedge member 143 made of stainless steel is inserted therein so as to be slidable. The wedge member 143 has a flat face portion which is orthogonal to the axis direction on the base end side, and has a sloping face 143a having a predetermined angle as to the axis direction on the tip side. The tip face of the D-shape portion 142a and the base end face of the wedge member 143 are in contact with one another.

On the outer circumference portion of the tip portion of the treatment unit 4 side of the turning receiving member 145, a ring-shaped bevel gear member 144 is affixed. The positions of the bevel gear member 144 and the bevel gear member 32 are determined so as to have the teeth of the bevel gear member 144 and the teeth of the bevel gear member 32 mesh, and are positioned within the space formed within the first tip cover 130a and the second tip cover 130b.

Also, when the turning/opening/closing force transmitting member 142 is moved toward the tip side within the sheath 110, the D-shape portion 142a passes through the D-shape hole of the turning receiving member 145, and advances out so as to move the wedge member 143 toward the tip side along the axis direction of the insertion unit 2. Also, the turning receiving member 145 is formed to be larger than the inner diameter of the sheath 10, and thus the turning receiving member 145 and the bevel gear member 144 are prevented from moving toward the operating unit 3 side.

Next, the configuration of the operating unit 3 of the needle driver 1 will be described. In a state wherein the operating unit cover 9a and the operating unit cover 9b are fit together, a sheath mounting hole 158 is formed on the tip side of the operating unit cover 9. The sheath 110 and the turning/opening/closing force transmitting member 142, extend into the inner portion of the operating unit 3, and further, on the base end side of the insertion unit 2, the sheath 110 is affixed to the operating unit cover 9. On the inner portion of the operating unit cover 9, a turning receiving member 162 is stored so as to be unable to move in the axis direction but able to turn about the axis. The turning receiving member 162 is made from stainless steel or resin, is in a cylindrical shape, and has a bottom face portion. In the inner portion of the operating unit 3, the base end portion of the sheath 110 is in contact with bottom face portion of the turning receiving member 162.

Also, the turning/opening/closing force transmitting member 142 has a D-shape portion 142b of which the cross-sectional shape is semicircle, as shown in FIG. 11, on the base end portion of the operating unit 3 side. The D-shape portion 142b of the turning/opening/closing force transmitting member 142 inserted inside the sheath 10 protrudes by a predetermined length on the base end side from the back end face of the sheath 10. The D-shape portion 142b is inserted through the D-shape hole provided on the turning receiving member 162 so as to be slidable. The D-shape portion 142b has at least one flat face portion wherein the cross-sectional shape of the face which is orthogonal to the axis direction of the turning/opening/closing force transmitting member 142 is a straight line. The D-shaped hole provided on the turning receiving member 162 has at least one flat face portion wherein the cross-sectional shape of the face which is orthogonal to the direction of the hole is a straight line, and this flat face portion is formed so as to face the flat face portion of the D-shape portion 142b.

In the above-described example, the D-shaped hole has at least one straight line portion in the cross-sectional shape orthogonal to the direction of the hole, and the D-shape portion has a straight line portion which faces this straight line portion. In other words, the turning/opening/closing force transmitting member 142 has D-shape portions 142a and 142b over a predetermined length on both end portions, which engages with the D-shape hole provided on the turning receiving member 145 and the turning receiving member 162, but the holes for the turning receiving member 145 and the turning receiving member 162 are not limited to a D-shaped hole, and can be a non-circular hole, and it is sufficient for the turning/opening/closing force transmitting member 142 to have a cross-sectional shape portion which engages with the shape of the non-circular hole, for the turning receiving member 145 and the turning receiving member 162 to interlock.

The turning receiving member 162 has an opening portion on the opposite side from the insertion unit 2 side, and therefore a concave shape is formed on the base end side, and a wedge member 161 made of a metal such as stainless steel is inserted thereto so as to be slidable. With the wedge member 161, the tip side has a flat face portion which is orthogonal to the axis direction, and the base end side has a sloping face 161a having a predetermined angle as to the axis direction.

A ring-shaped bevel gear member 160 is affixed to the outer circumference portion of the base end side of the turning receiving member 162. The positions of the bevel gear member 160 and the bevel gear member 53 are determined so as to have the teeth of the bevel gear member 160 and the teeth of the bevel gear member 53 mesh, and are positioned within the space formed within the operating unit cover 9a and the operating unit cover 9b.

As described above, the wedge member 161 has a sloping portion which has a sloping face 161a having a predetermined angle as to the axis of the insertion unit 2, which is formed on the tip portion of the base end side of the operating unit 3. Within the operating unit cover 9, the positions of the wedge member 57 and the wedge member 161 are determined so that the sloping face 57a and the sloping face 161a are in contact. When the opening/closing button 8 is pressed, the rod member 55 moves so as to press the wedge member 57 against the wedge member 161. When the sloping face 57a of the wedge member 57 moves while sliding along the surface of the sloping face 161a, the wedge member 161 moves the turning/opening/closing force transmitting member 142 towards the treatment unit 4 side along the axis direction of the insertion unit 2.

The positions of the bevel gear member 160 and the bevel gear member 53 are determined so as to have the teeth of the bevel gear member 160 and the teeth of the bevel gear member 53 mesh, and are positioned within the space formed within the operating unit cover 9a and the operating unit cover 9b. Accordingly, when the surgeon turns the turning dial 7 with a finger, the turning force turns the turning/opening/closing force transmitting member 142 about the axis of the insertion unit 2, via the bevel gear members 53 and 160 and the turning receiving member 162. The turning force of the turning/opening/closing force transmitting member 142 turns the second gripping member 21a about the axis of the treatment unit 4, via the bevel gear members 144 and 32. At this time, the ring member 23 of the first gripping member 21b is pressed into close contact with the second gripping member 21a by the coil spring 27, and accordingly the turning force of the turning/opening/closing force transmitting member 142 turns the gripping members 21a and 21b of the gripping unit 5.

The operation and actions of the needle driver 1 as configured above will be described. When the surgeon turns the turning dial 7, the turning force thereof turns the turning/opening/closing force transmitting member 142 about the axis thereof, with the two bevel gear members 53 and 160. The transmitting of the turning force is performed by the turning/opening/closing force transmitting member 142 and the turning receiving members 145 and 162 turning as one unit, since the flat face portions of the two D-shape portions provided on both end portions of the turning/opening/closing force transmitting member 142 and the flat face portions of the two D-shape holes are in contact with one another. As a result, the turning of the turning/opening/closing force transmitting member 142 turns the gripping unit 5 with the two bevel gear members 144 and 32. Thus, the surgeon can turn the gripping unit 5 by the turning operation of the turning dial 7. That is to say, the two gripping members 21 are turned with the axis of the treatment unit 4 in the center, with the turning of the turning dial 7.

Further, when the opening/closing button 8 is pressed with a finger, as shown in FIG. 12, the wedge member 161 is moved towards the treatment 4 side while sliding over each of the sloping faces 57a and 161a by the movement of the wedge member 57. The D-shape portion 142b which is a transmitting axis unit of the opening/closing force moves toward the tip side within the sheath 110, through the D-shape hole which is the opening/closing force transmitting hole portion of the turning receiving member 162.

When the turning/opening/closing force transmitting member 142 moves in the direction of the tip portion of the insertion unit 2, as shown in FIG. 13, the sloping face 143a of the wedge member 143 provided on the tip portion of the turning/opening/closing force transmitting member 142 presses against the wedge-receiving unit 24a of the first gripping member 21b, and thus the first gripping member 21b moves in the direction of the axis of the first gripping member 21b and the direction wherein the ring member 23 moves away from the first tube 25.

In this state, when the opening/closing button 8 is released, the turning/opening/closing force transmitting member 142 moves toward the base end direction of the insertion unit 2, and further, the first gripping member 21b and the second gripping member 21a are closed with the coil spring 27. That is to say, the turning/opening/closing force transmitting member 142 comprises a turning and advancing/retreating mechanism, that is, a transmitting mechanism, which transmits the opening/closing force wherein the turning/opening/closing force transmitting member 142 advances or retreats within a predetermined distance between two bevel gears, while the turning force of each bevel gear is transmitted on both ends.

The method of gripping a needle and so forth is similar to the method as described in the first embodiment, and so the description thereof will be omitted.

Thus, according to the surgical instrument of the present embodiment, the configuration is such that the opening/closing force and the turning force is transmitted to the gripping unit, with the rod member which has a D-shape portion on both end portions. Specifically, the transmitting mechanism of the opening/closing force and the transmitting mechanism of the turning force are one unit, and so compared to the configuration of the first embodiment, the diameter of insertion unit 2 can be made even smaller. Accordingly, a needle driver with good operating capabilities can be realized with a simple configuration.

Figure 14:
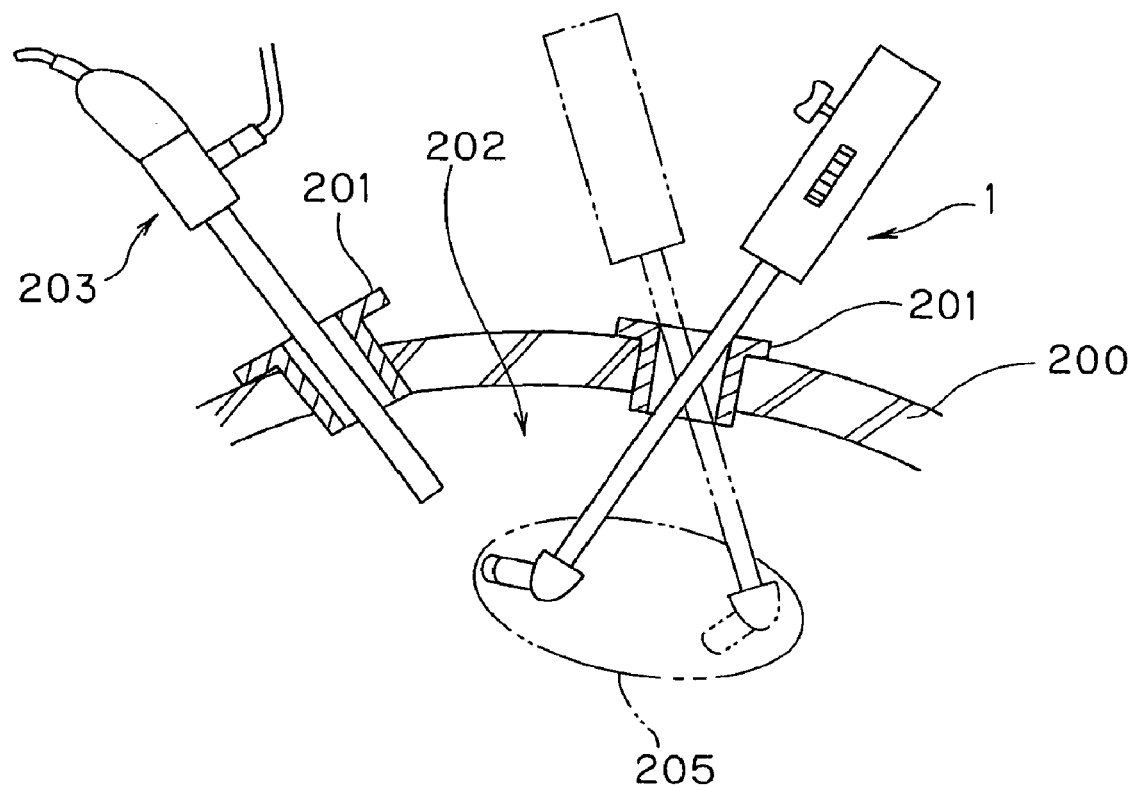
FIG. 14 is a schematic view showing the state of approaching the surgical area with the needle driver via a trocar.

FIG. 14 is a schematic view showing the state of approaching the surgical area with the needle driver relating to the above-described embodiments, via a trocar. Here, description is made for a case wherein the trocar is not an airtight trocar. A trocar 201 is attached to a body cavity 200, and various surgery is performed while observing the body cavity inside 202 while using an endoscope 203. The needle driver 1 and the endoscope 203 are each inserted into the body cavity inside 202 via the trocar 201, but there is a limit to the inner diameter of the hole of the trocar 201. According to the present invention, the insertion unit 2 can be made with a smaller diameter, and therefore the insertion unit 2 can make various movements within the hole of the trocar 201.

As a result, as shown in FIG. 14, the moveable range 205 of the treatment unit 4 within the body cavity 205 is increased, and the surgeon can perform surgery more easily, and the usability thereof is also improved. Particularly, according to the configuration relating to the second embodiment, the insertion unit can be made smaller than the needle driver with a configuration relating to the first embodiment, and therefore the moveable range 205 of the treatment unit 4 within the body cavity is increased.

Thus, according to the present embodiment, a needle driver with good operational functionality can be realized with a simple configuration.

Third Embodiment

Next, a third embodiment will be described.

Figure 15:
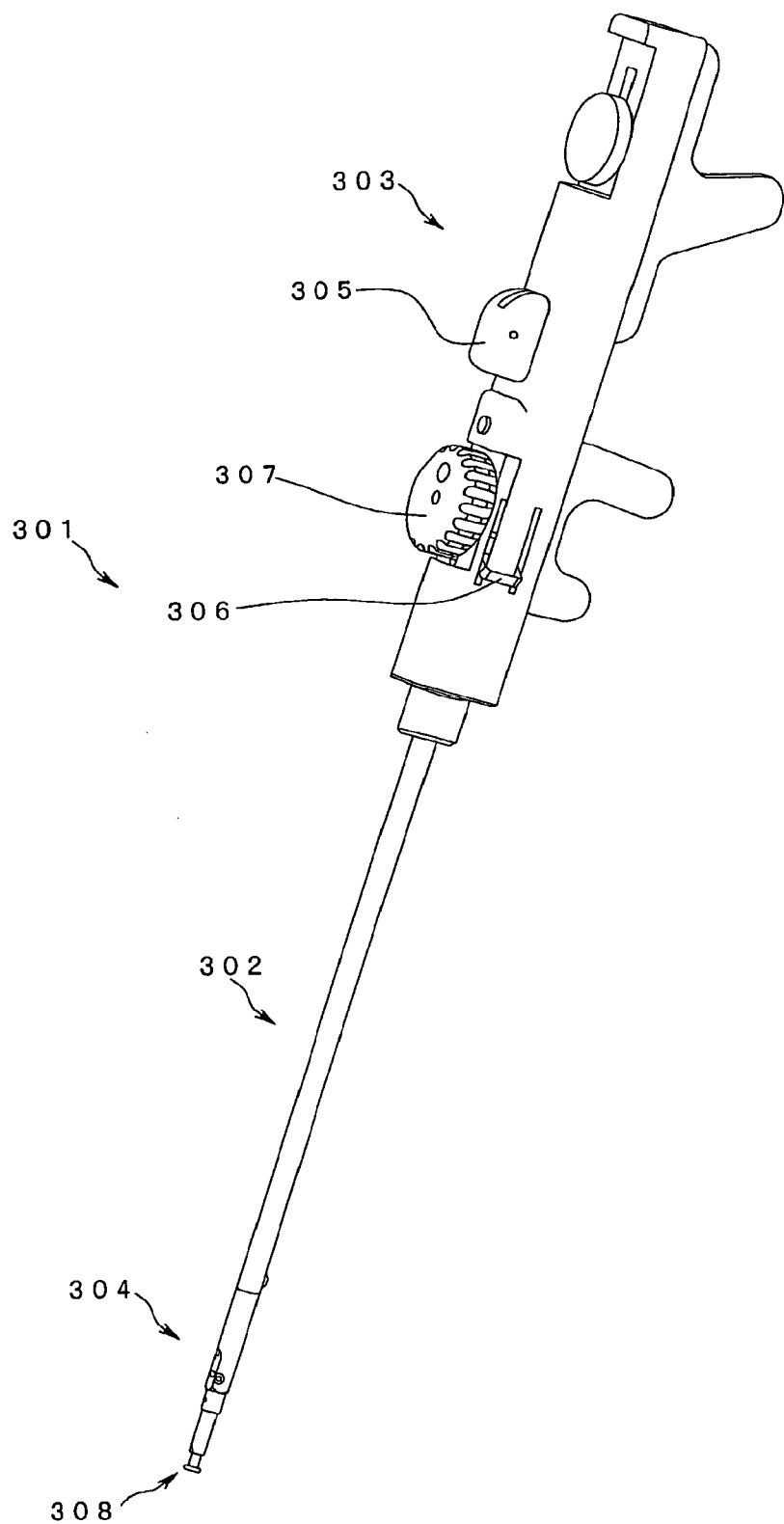
FIG. 15 is an external perspective view of a needle driver according to a third embodiment of the present invention, seen from one front diagonal side.
Figure 16:
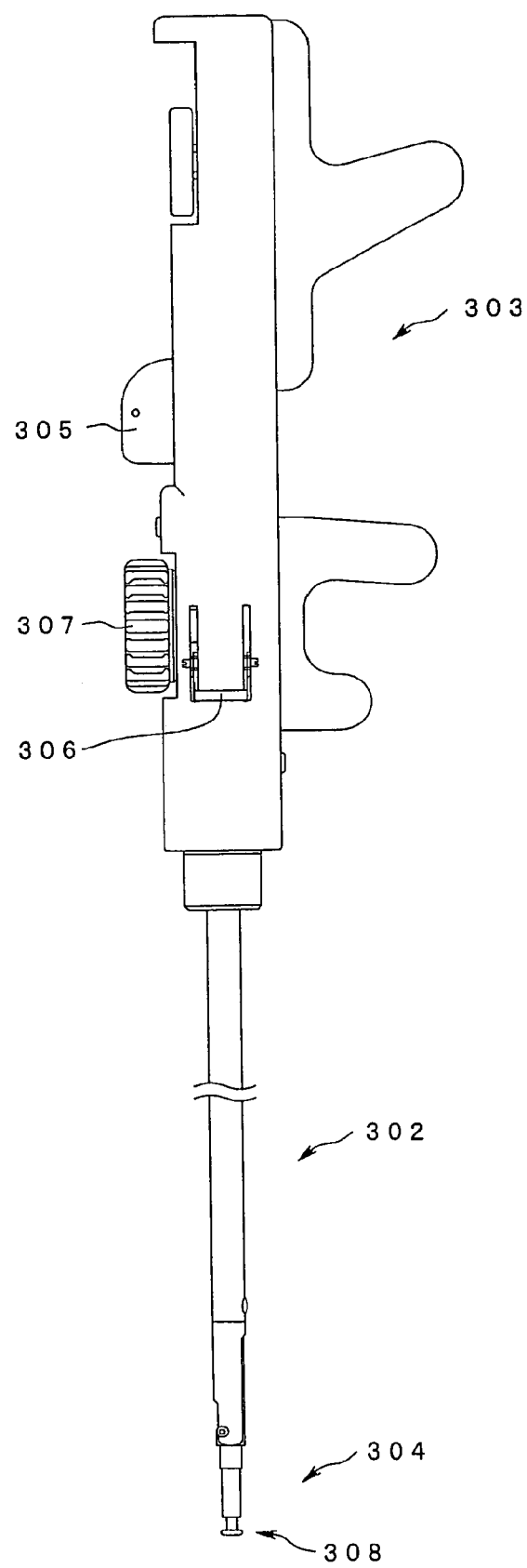
FIG. 16 is a front view of a needle driver according to the third embodiment of the present invention.
Figure 17:
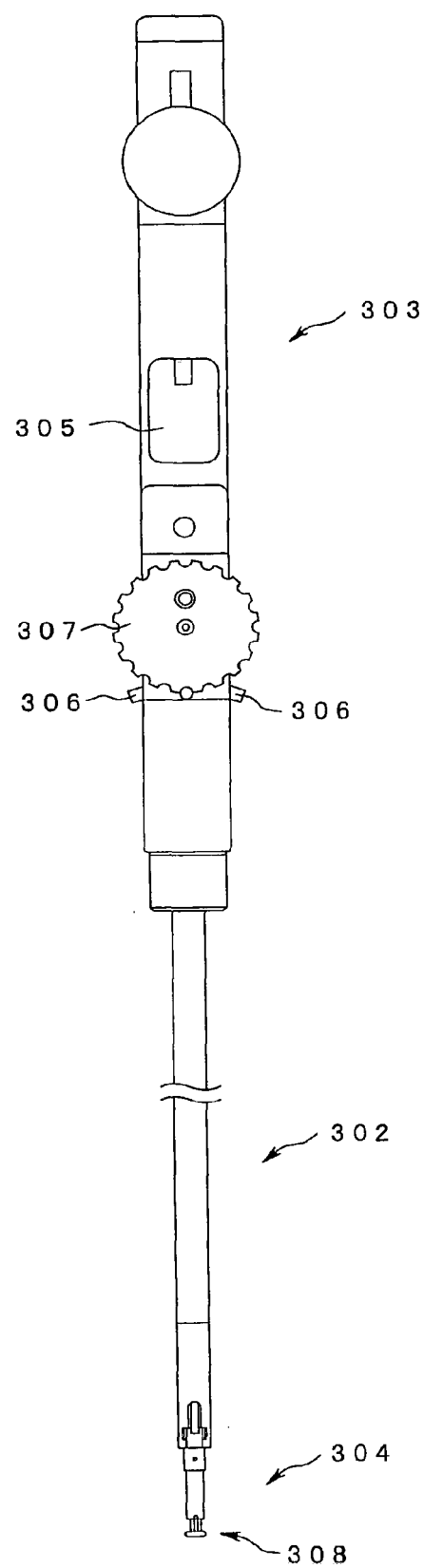
FIG. 17 is a left side view of a needle driver according to the third embodiment of the present invention, seen from one side (the left side)
Figure 18:
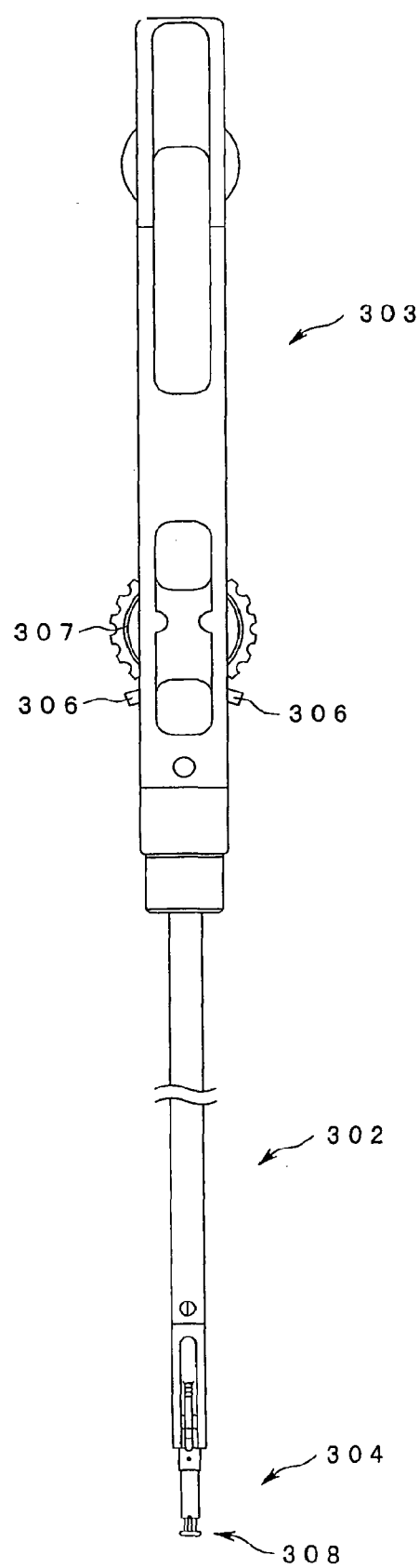
FIG. 18 is a right side view of a needle driver according to the third embodiment of the present invention, seen from another side (the right side)

FIG. 15 is an external perspective view of a needle driver relating to a third embodiment, seen from one front diagonal side. FIG. 16 is a front view of the needle driver according to the present embodiment, FIG. 17 is a left side view of the needle driver according to the present embodiment, seen from one side (the left side), and FIG. 18 is a right side view of a needle driver according to the present embodiment, seen from another side (the right side).

As shown in FIGS. 15 through 18, a needle driver 301 primarily comprises an insertion unit 302, an operating unit 303 which is provided on one side (the base end side) of the insertion unit 302, and a treatment unit 304 which is provided so as to extend from the other end of the insertion unit 302.

The insertion unit 302 has a general cylindrical shape with a predetermined length. Also the operating unit 303 is a member on the base end side of the insertion unit 302, having an approximate rectangular shape which is arranged as one unit on the same axis as the long axis of the insertion unit 302, and the shape is such that the surgeon can grip this with one hand and perform operation to be described later.

Also, an opening/closing button 305 which is an opening/closing member for performing opening/closing operations of the treatment unit 304, an angle-variable lever 306 which is an angle changing operating member for performing operations to change the angle in the extension direction of the treatment unit 304, and a turning dial 307 which is a turning operating member for performing turning operations of the treatment unit 304, are provided on the operating unit 303.

The base end portion of the opening/closing button 305 is pressed to the direction separated from the exterior of the operating unit 303 by the pressing force of the spring to be described later. Also, one end on the base end side of the traction wire to be described later is retained by the member engaged with the opening/closing button 305. When the opening/closing button 305 is pressed, a force is applied to the traction wire to resist the pressing force of the spring within the treatment unit which will be described later. The configuration of the opening/closing button 305 will be described later.

The treatment unit 304, which is provided so as to extend from one end of the insertion unit 302, has a gripping unit 308 on the tip side, and the axis direction of the gripping unit 308, that is to say, the extension direction of the treatment unit 304 can change within a range of a predetermined angle as to the axis direction of the insertion unit 302, for example within the range of 0 to 90 degrees. In other words, angle-changing means for changing the angle in the extension direction of the treatment unit 304 as to the axis of the insertion unit 302 is provided on the needle driver 301.

Figure 19:
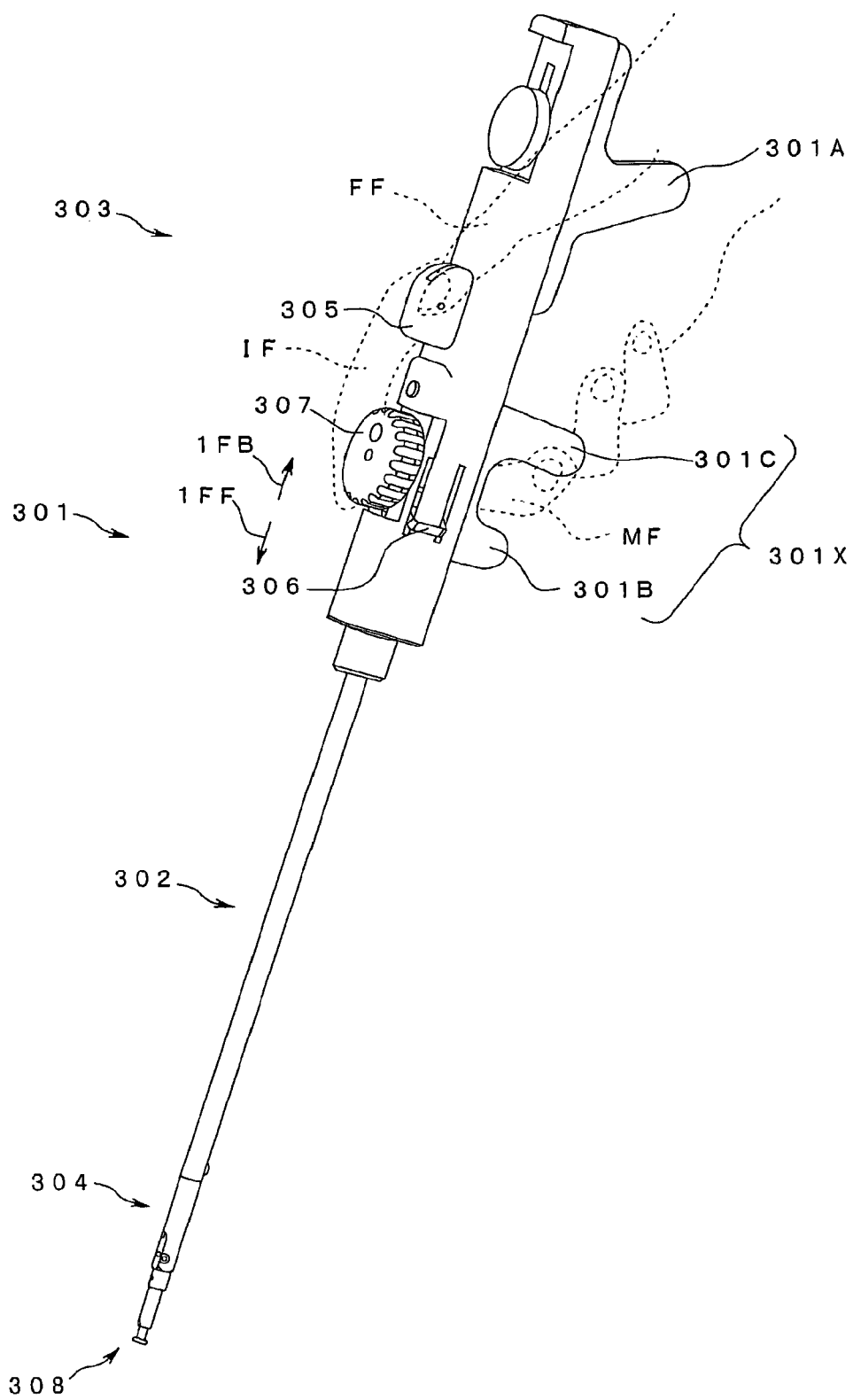
FIG. 19 is a diagram describing a state of grasping the needle driver in FIG. 15.

FIG. 19 is a diagram describing a state of grasping the needle driver 301 in FIG. 15. As shown in FIG. 19, the surgeon places the base portion between the thumb FF and index finger IF on the palm resting member 301A made of resin, and places the middle finger MF between the two protruding portions 301B and 301C of the finger resting member 301X made of resin, and thus the surgeon can firmly and securely grip the needle driver 301. As shown in FIG. 19, in a state of gripping the needle driver 301, the surgeon can operate the turning dial 307 and the angle-variable lever 306 with the index finger IF. The turning dial 307 and the angle-variable lever 306 can be operated by the index finger IF in the directions of the tip direction IFF and the base end direction IFB of the insertion unit 302. Further, the opening/closing button 308 can be operated with the thumb FF.

Further, the palm resting member 301A is extended diagonally slightly toward the base end side from the side portion of the operating unit 303, and therefore the palm resting member 301A and the palm are in close contact when gripping, and thus the surgeon can firmly grip the needle driver 301.

Next, the configuration of the tip portion of the needle driver 301 will be described with reference to FIGS. 20 through 25.

FIGS. 20 through 23 are diagrams for describing the configuration of a tip portion which includes the treatment unit 304 of the needle driver 301.

Figure 20:
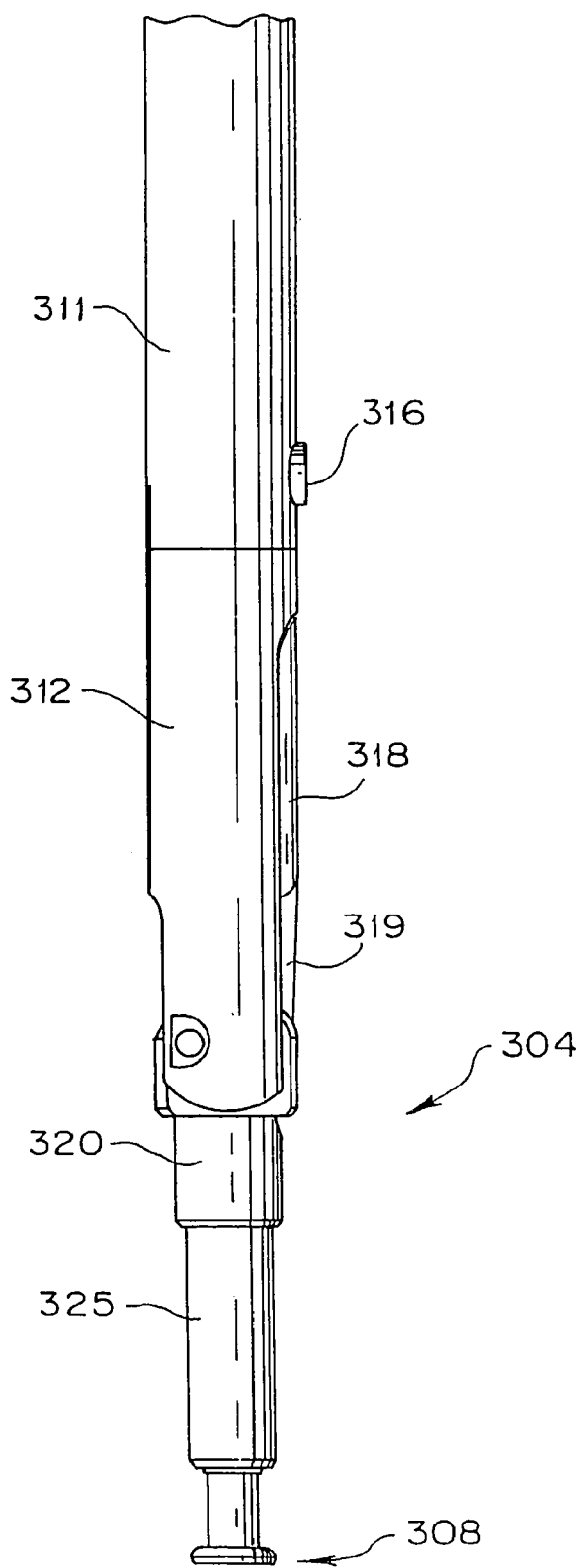
FIG. 20 is a front view of the tip portion, including a treatment unit, of the needle driver according to the third embodiment.
Figure 21:
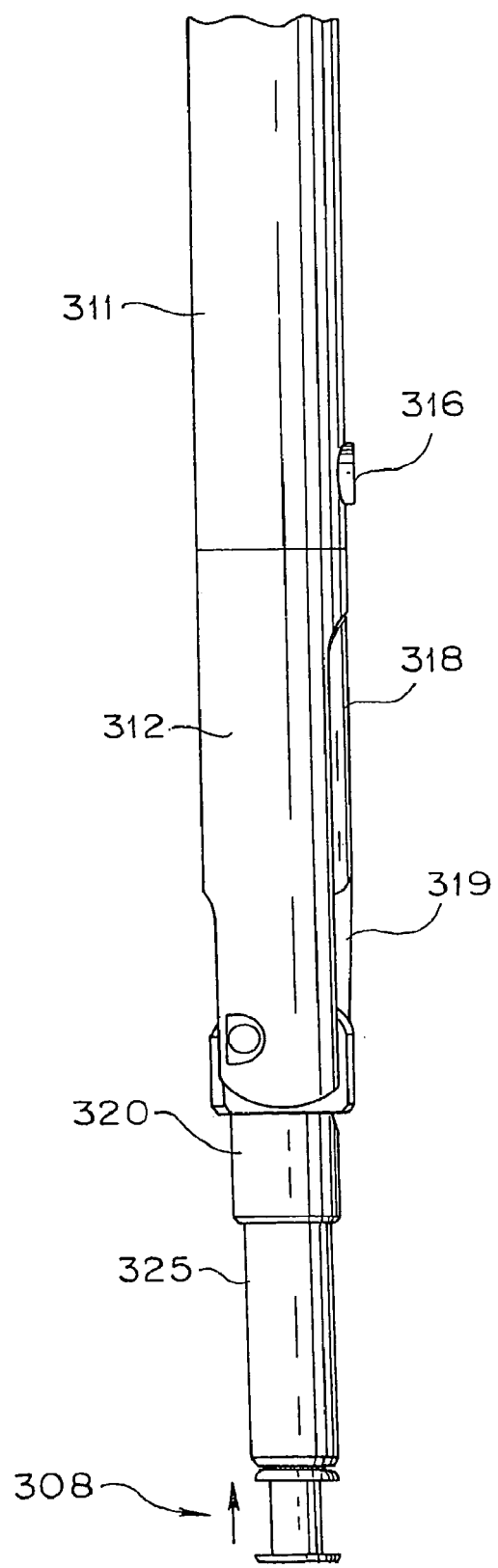
FIG. 21 is a front view of the tip portion, showing a state wherein a gripping unit of the treatment unit is open, according to the third embodiment.
Figure 22:
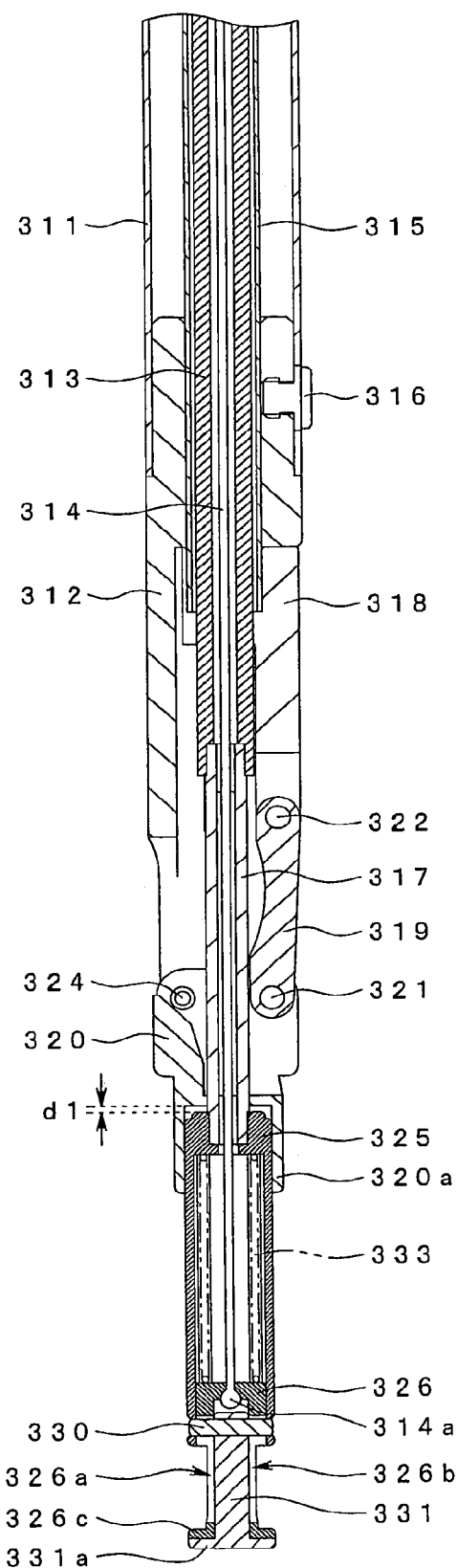
FIG. 22 is a cross-sectional view of the tip portion, including a treatment unit, along the axis direction of the needle driver according to the third embodiment.
Figure 23:
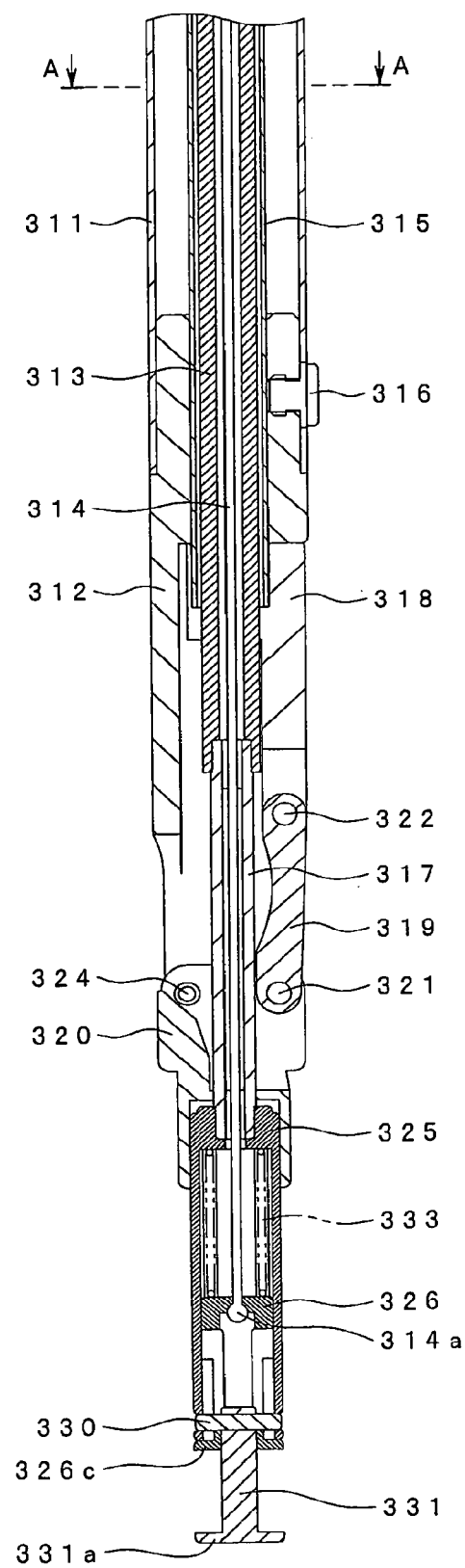
FIG. 23 is a cross-sectional view of the tip portion, showing a state wherein the gripping unit of the treatment unit is open, along the axis direction of the needle driver according to the third embodiment.
Figure 24:
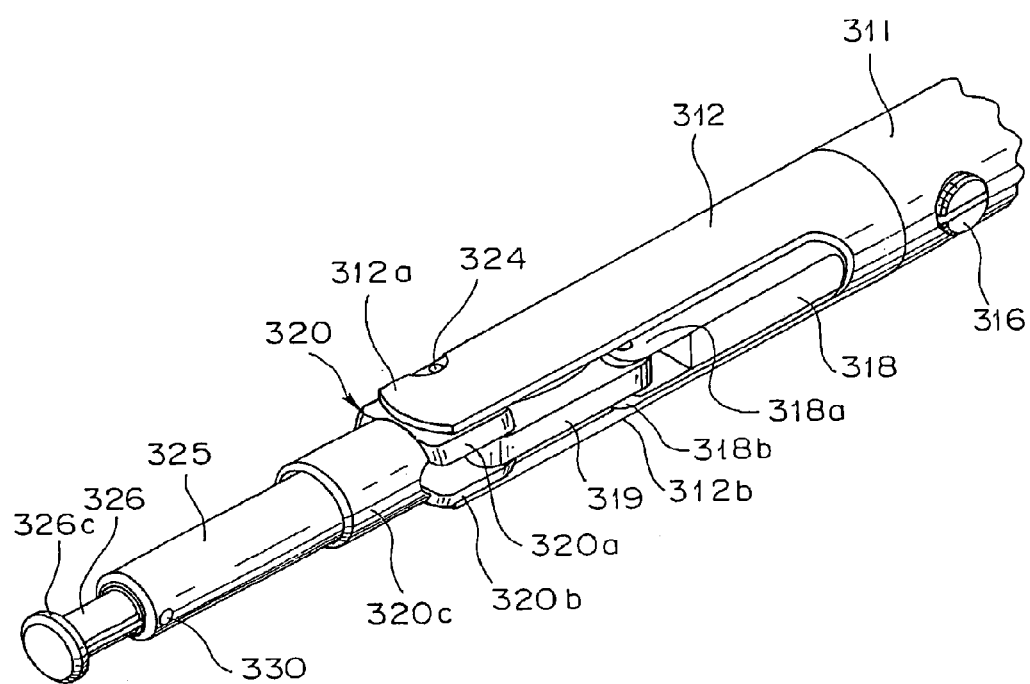
FIG. 24 is a perspective view describing the internal configuration of the tip portion according to the third embodiment.
Figure 25:
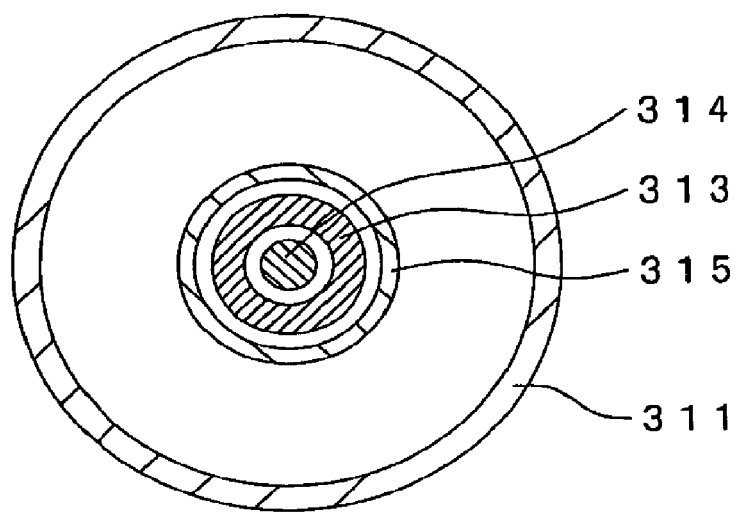
FIG. 25 is a cross-sectional view along the A-A line in FIG. 23.

FIG. 20 is a front view of the tip portion including the treatment unit 304 of the needle driver 301, FIG. 21 is a front view of the tip portion, showing a state wherein the gripping unit 308 of the treatment unit 304 is open, FIG. 22 is a cross-sectional view of the tip portion including the treatment unit 304, along the axis direction of the needle driver 301, FIG. 23 is a cross-sectional view of the tip portion, showing a state wherein the gripping unit 308 of the treatment unit 304 is open, along the axis direction of the needle driver 301, FIG. 24 is a perspective view describing the internal configuration of the tip portion, and FIG. 25 is a cross-sectional view along the A-A line in FIG. 23.

The insertion unit 302 has a stainless steel pipe, that is to say, a sheath 311 which is a cylindrical member. The tip side of the sheath 311, that is to say, on the treatment unit 304 side, a stainless steel tip housing member 312 is fixed thereupon.

The tip housing member 312 has a cylindrical fitting unit which fits to the inner surface of the sheath 311 on the base end side of the tip housing member 312, that is to say, on the sheath 311 side.

As shown in FIG. 24, the center portion of the tip housing member 312 has a space inside, and has a channel shaped portion wherein the cross-sectional shape orthogonal to the axis of the insertion unit 302 is in a channel shape. The tip housing member 312 has two arm units 312a and 312b which extend to the tip side, so as to be on either side of the inner space communicating with the inner space within the channel-shaped unit on the tip side (in other words on the gripping unit 308 side), as shown in FIG. 24.

As shown in FIG. 22, a stainless steel bending force transmitting pipe 315 which is a shaft member is inserted through the sheath 311. The bending force transmitting pipe 315 is a member for changing the angle of the extension direction of the treatment unit 304 so as to bend the treatment unit 304.

A bending force transmitting pipe 315 is inserted through the sheath 311, and a turning force transmitting pipe 313 made of stainless steel, which is a shaft member, is inserted through the bending force transmitting pipe 315. The turning force transmitting pipe 313 is a pipe for transmitting turning force to the tip portion. A traction wire 314 formed of stainless steel for the opening/closing operation of the gripping unit 308 to be described later is inserted through the turning force transmitting pipe 313.

Accordingly, as shown in FIG. 25, the bending force transmitting pipe 315, the turning force transmitting pipe 313, and the traction wire 314 are arranged on the inner side of the sheath 311, on the same axis thereof.

The traction wire 314 is a wire member which is pulled towards the operating unit 303 side for performing opening operations of the gripping unit 308, and is knit togethe with a thin stainless steel wire and is configured to be flexible. Also, the wire surface can be coated with a fluorine resin, so as to lower the sliding resistance and enable advancing or retreating to be easier on the inner portion.

The tip housing member 312 is fixed to the sheath 311 with a stopping screw 316 made of stainless steel. Further, the tip portion of the sheath 311 and the tip housing member 312 are fixed by applying an adhesive such as an epoxy resin adhesive.

The turning force transmitting pipe 313 as described above is inserted so as to be capable of turning and sliding, with the axis of the turning force transmitting pipe 313 as the center of the turning, and the bending force transmitting pipe 315 is inserted so as to be capable of advancing or retreating in the axis direction of the bending force transmitting pipe 315.

On the tip of the turning force transmitting pipe 313, a turning force transmitting coil 317 made of stainless steel is fixed. The turning force transmitting coil 317 is a flexible coil for transmitting the turning force to the tip portion of the insertion unit 302. A traction wire 314 is inserted through the inside of the turning force transmitting coil 317. The turning force transmitting pipe 313 is made of metal, and therefore the turning force from the turning operation of the turning dial 307 at the operating unit 303 can be securely transmitted to the turning force transmitting coil 317.

The turning force transmitting coil 317 which is connected to the turning force transmitting pipe 313 has a triply-layered-winding-adhering configuration wherein three coils are layered together. A second coil is provided in the roll direction opposite from the roll direction of the bottom-most coil, so as to layer the second coil on top of the bottom-most coil, and a third coil is provided in the roll direction opposite from the roll direction of the second coil (the same direction as the bottom-most coil), so as to layer the third coil on top of the second coil.

Both ends of the turning force transmitting coil 317 are brazed, and after being brazed, are cut. As a result, the thickness of both end portions are thinner than the thickness of the center portion. Also, the end portions are each fixed to the turning force transmitting pipe 313 and a turning unit base member 325 by brazing.

The bending force transmitting pipe 315 is linked to the bending unit base member 320 made of stainless steel, via a linking member 319 made of stainless steel and a joint member 318 which is a linking member made of stainless steel. The base end portion of the joint member 318 is configured so that the turning force transmitting pipe 313 is inserted so as to be slidable in the axis direction of the turning force transmitting pipe 313 and about the axis thereof. Further, the bending force transmitting pipe 315 is linked with the joint member 318, by being provided between the joint member 318 and the base end portion in close contact, and therefore, along with the bending force transmitting pipe 315 advancing or retreating along the axis direction of the insertion unit 302, the joint member 318 also advances or retreats in the same direction.

Figure 26:
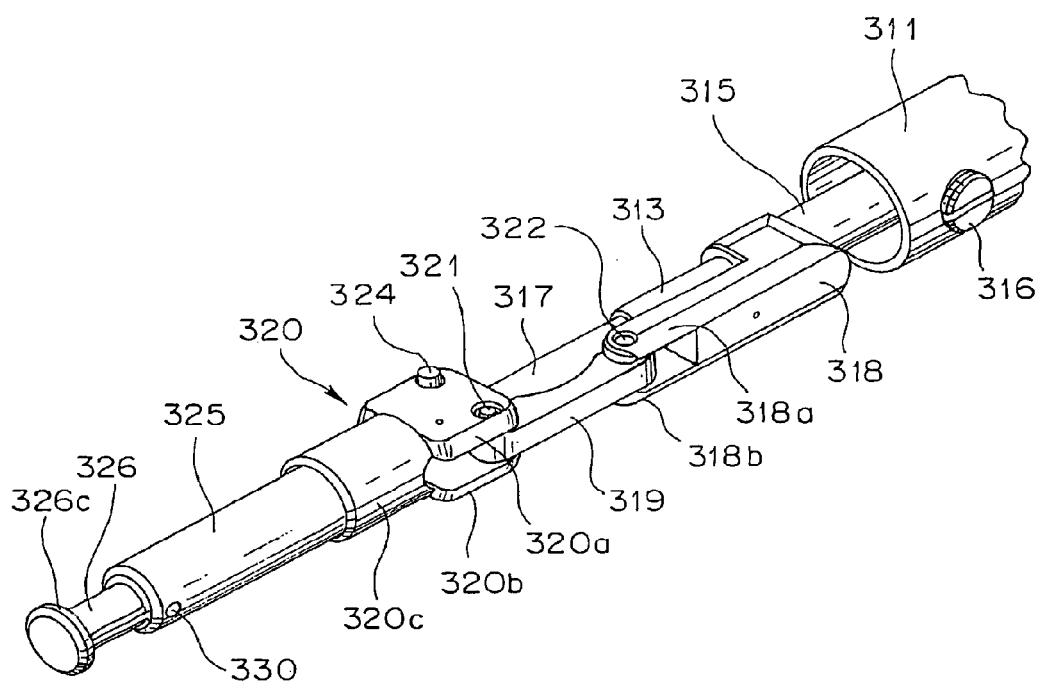
FIG. 26 is a perspective view describing the internal configuration of the tip portion according to the third embodiment, wherein the tip housing member is omitted.

The connection relationships between the bending force transmitting pipe 315, the joint member 318, the linking member 319, and the bending unit base member 320 will be described with reference to FIGS. 24 and 26. FIG. 26 is a perspective view describing the internal configuration of the tip portion, wherein the tip housing member 312 is omitted.

As shown in FIG. 24, the tip housing member 312 fits with the inner surface of the sheath 311 on the base end side of the tip housing member 312. Within the center portion and the tip portion of the tip housing member 312, a portion of the bending force transmitting pipe 315, the turning force transmitting coil 317, the joint member 318, and a portion of the linking member 319 and the bending unit base member 320 are arranged. A bending unit base member 320 is arranged between the two arm units 312a and 312b of the tip housing member 312, and the bending unit base member 312 and the tip housing member 312 are linked with a pin 324. Specifically, the bending unit base member 320 and the tip housing member 312 are linked by having a pin 324, which fits in the two arm units 312a and 312b, to fit into a hole provided on the bending unit base member 320, and the bending unit base member 320 can turn, with the axis of the pin 325 as the turning center.

Also, as shown in FIG. 26, the joint member 318 has two arm units 318a and 318b on the tip side thereof. The linking member 319 is a rod member having a hole portion on each of both end portions. The bending unit base member 320 has two arm units 320a and 320b on the base end side. Also, the bending unit base member 320 has a cylindrical portion 320c on the tip side thereof, and the base end portion of the turning unit base member 325 is fit into the inner side of the cylindrical unit 320c.

The bending unit base member 320 and the linking member 319 are linked by a pin 321 which passes through the two arm units 320a and 320b and the hole in the tip portion of the linking member 319, so as to sandwich the tip portion of the linking member 319 between the two arm units 320a and 320b of the bending unit base member 320. The pin 321 is fixed with a laser welding with the tip portion of the bending unit base member 320, but the linking member 319 can turn with the axis of the pin 321 as the turning center.

Also, the joint member 318 and the linking member 319 are linked by a pin 322 which passes through the two arm units 318a and 318b and the hole in the tip portion of the linking member 319, so as to sandwich the base end portion of the linking member 319 between the two arm units 318a and 318b. The pin 322 is fixed with a laser welding with the tip portion of the joint member 318, but the linking member 319 can turn with the axis of the pin 322 as the turning center.

Figure 27:
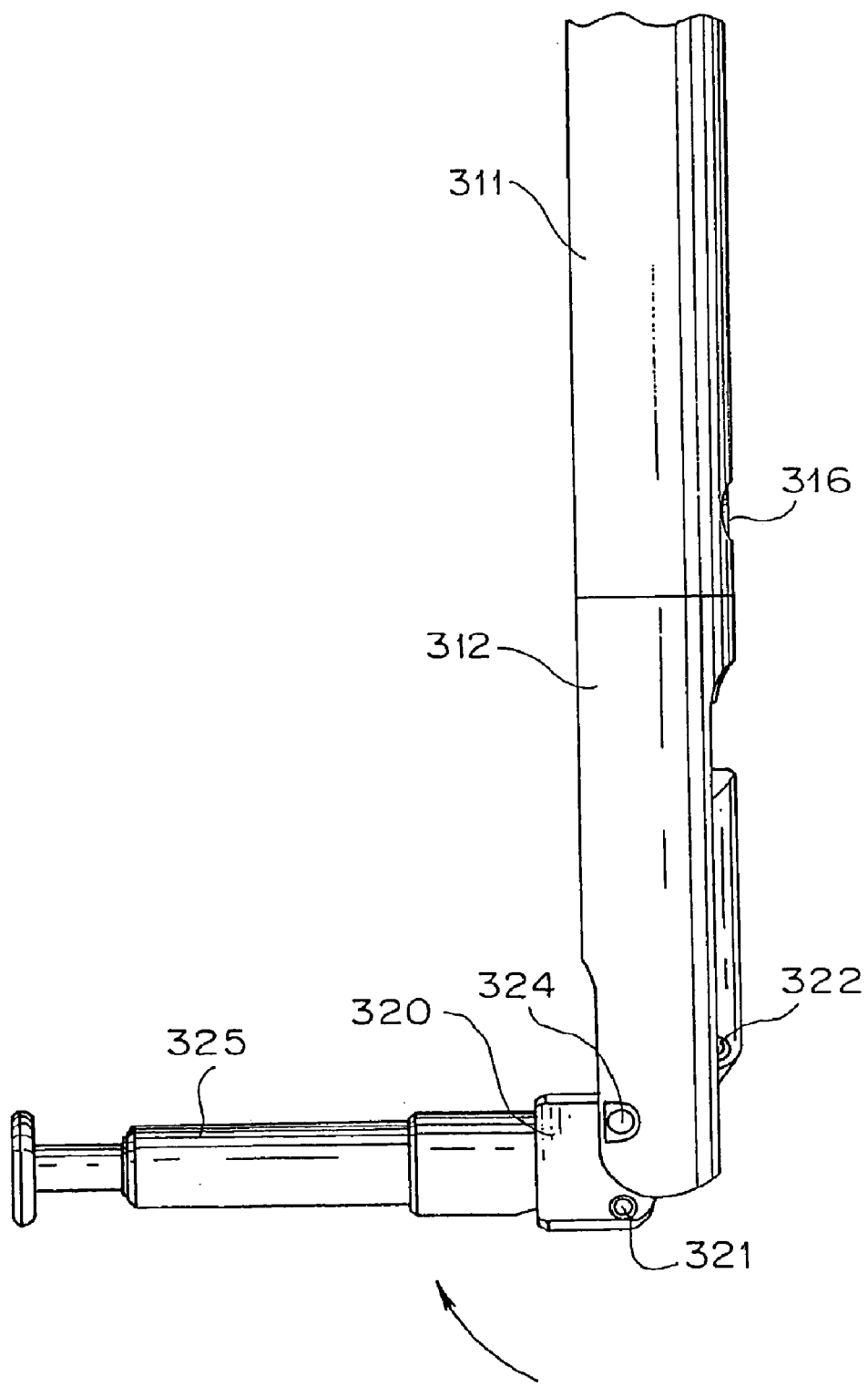
FIG. 27 is a front view of the tip portion according to the third embodiment, showing the state wherein the treatment unit is bent at a 90-degree angle as to the axis of the insertion unit.
Figure 28:
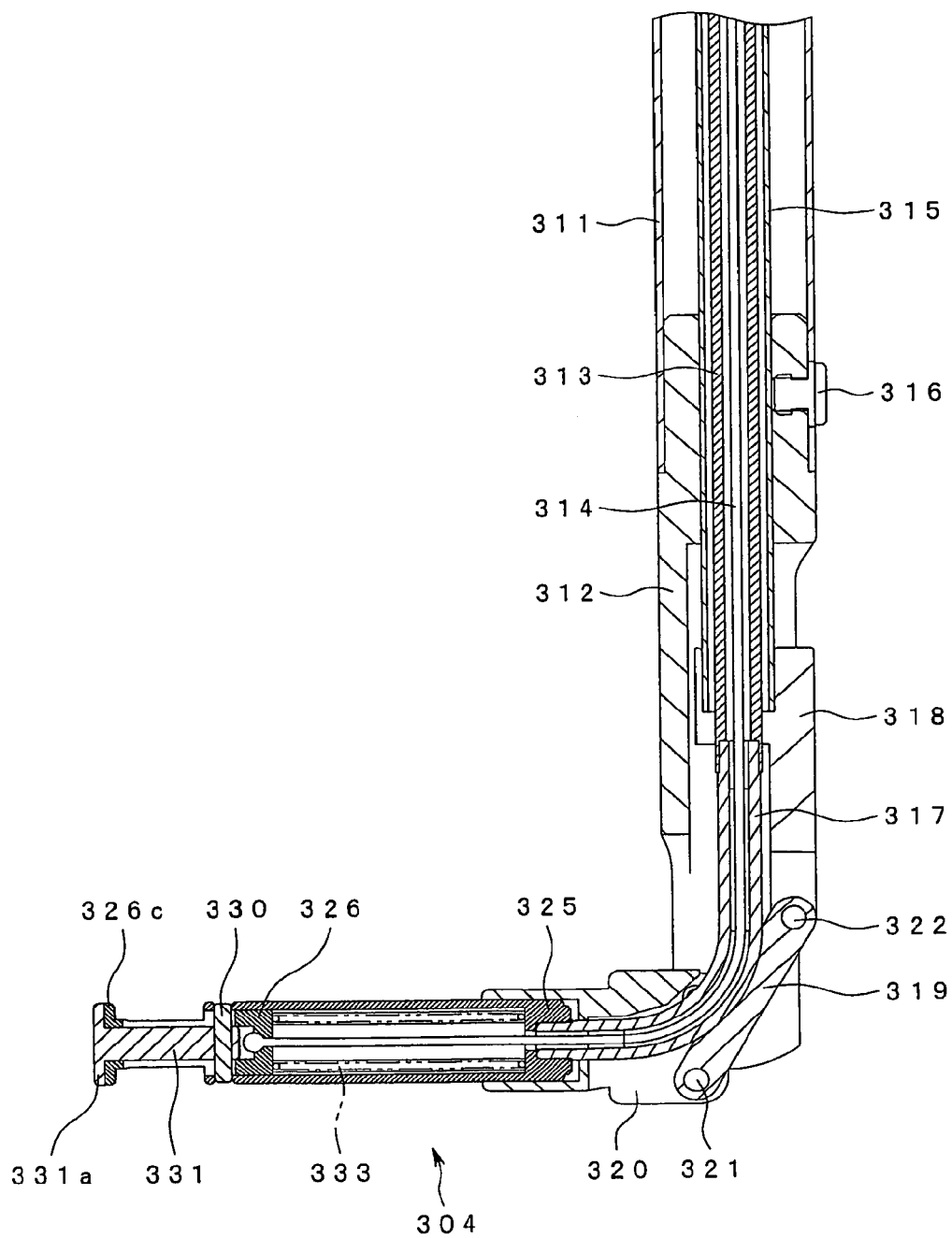
FIG. 28 is a cross-sectional view of the tip portion according to the third embodiment, showing the state wherein the treatment unit is bent at a 90-degree angle as to the axis of the insertion unit.

Accordingly, when the bending force transmitting pipe 315 is advanced to the tip side in the axis direction of the operating unit 303 by operating an angle-variable lever 306 on the operating unit 303, the bending unit base member 320 turns with a pin 324 as the turning center. FIG. 27 is a front view of the tip portion, showing the state wherein the treatment unit 304 is bent at a 90-degree angle as to the axis of the insertion unit 302. FIG. 28 is a cross-sectional view of the tip portion, showing the state wherein the treatment unit 304 is bent at a 90-degree angle as to the axis of the insertion unit 302. Also, when the bending force transmitting pipe 315 is returned to the base end side of the axis direction of the operating unit 303 by operating the angle-variable lever 306, the extension direction of the treatment unit 304 is an angle smaller than 90 degrees as to the axis of the insertion unit 302. The pins 321, 322, and 324 are made of stainless steel. A mechanism will be described later, by which the bending force transmitting pipe 315 advances or retreats in the axis direction of the operating unit 303, by using a finger to cause the angle-variable lever 306 on the operating unit 303 to advance or retreat in the axis direction of the insertion unit 302.

Returning to FIG. 22, a cylindrical turning unit base member 325 is fit into the inside of the cylindrical unit 320a of the bending unit base member 320, so as to be capable of turning with the axis of the turning unit base member 325 as the turning center. The turning unit base member 325 has an opening portion on the tip side, and a bottom portion on the base end side. A hole is formed on the bottom portion of the base end side of the turning unit base member 325, and the tip portion of the turning force transmitting coil 317 is inserted into the hole, and is fixed by welding as described above.

The turning force transmitting coil 317 is fixed by welding to the turning force transmitting pipe 313 on the base end side, as described above, and on the tip side also is fixed by welding to the turning unit base member 325. The tip portion of the turning force transmitting coil 317 is inserted into the bottom portion on the base end side of the turning unit base member 325, and is welded. The base end portion of the turning force transmitting coil 317 is inserted to the step portion formed within the tip portion of the turning force transmitting pipe 313 and is welded. Thus, when the turning force transmitting pipe 313 is turned with the axis of the turning force transmitting pipe 313 as the turning center, the turning force transmitting coil 317 and the turning unit base member 325 also are similarly turned, so as to transmit the turning amount of the turning force transmitting pipe 313 to the treatment unit 304.

As shown in FIG. 22, in a state wherein the treatment unit 304 is not bent, the base end side bottom portion of the turning unit base member 325 and the base end side bottom portion of the turning unit base member 325 is separated by a predetermined distance of d1. As the treatment unit 304 is increasingly bent, the base end side bottom portion of the turning unit base member 325 and the base end side bottom portion of the turning unit base member 325 move closer together. Accordingly, when the treatment unit 304 is bent the maximum amount (for example up to 90 degrees) as will be described later, the base end side bottom portion of the turning unit base member 325 and the base end side bottom portion of the turning unit base member 325 is separated in advance by the predetermined distance of d1, so that the base end side bottom portion of the turning unit base member 325 and the base end side bottom portion of the turning unit base member 325 do not make contact and generate friction resistance. If the distance d1 is set at 0 (zero), the friction resistance increases, but suppressing movement in the long axis direction of the treatment unit 304 of the turning unit base member 325 as to the bending unit base member 320 which accompanies the bending operation, is possible.

On the tip portion of the treatment unit 304, a gripping unit 308 which includes two gripping members for gripping a needle are provided, and one of these is a movable gripping section 326, and the other is a fixed gripping section 331.

The turning unit base member 325 is made of stainless steel, and a portion of the movable gripping section 326 which is one of the gripping members 308 of the treatment unit 304 is inserted from the opening portion of the tip side, into the turning unit base member 325. The movable gripping section 326 is made of stainless steel, and is a cylindrical member having a inner facing flange portion on the base end side.

On the bottom portion of the base end side of the movable gripping section 326, a hole is provided through which the traction wire 314 can be inserted. On the tip portion of the traction wire 314, an enlarged end portion 314a which is formed by melting the tip portion is formed, and this enlarged end portion 314a is fixed on the inner side of the bottom portion of the movable gripping section 326. Accordingly, when the traction wire 314a is pulled to the operating unit 303 side, the movable gripping section 326 also is moved towards the operating unit 303 side.

Figure 29:
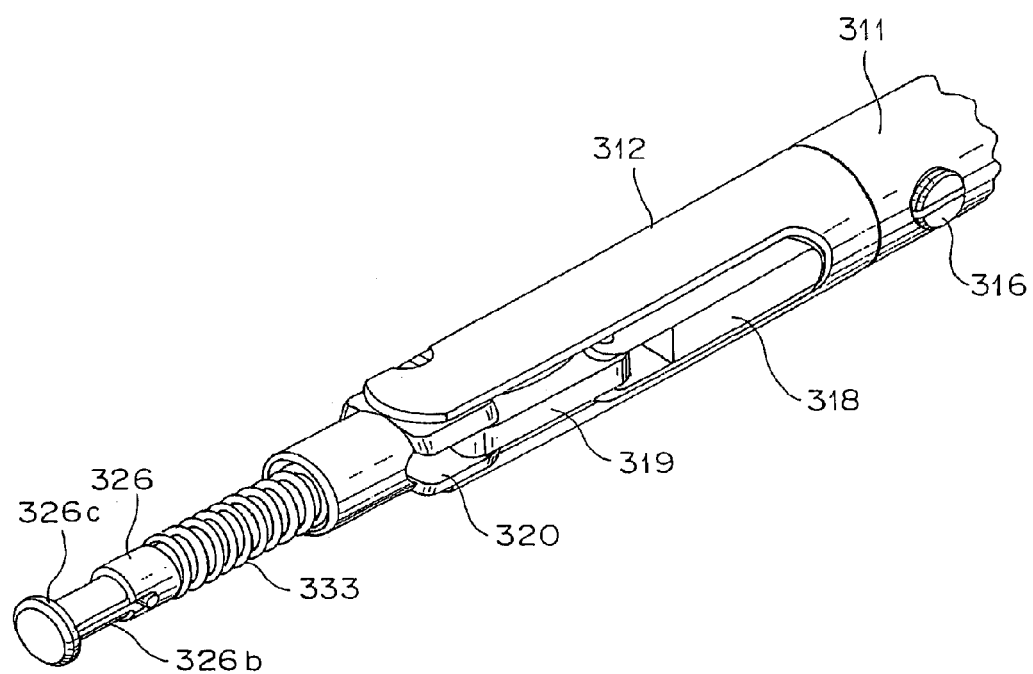
FIG. 29 is a perspective view describing the internal configuration of the tip portion according to the third embodiment, wherein the turning unit base member is omitted.

On the inner side of the cylindrical portion of the turning unit base member 325, and between the circumferential face of the bottom portion of the movable gripping section 326 and the interior face of the bottom portion of the turning unit base member 325 which faces against the circumferential face thereof, a spring 333 made of stainless steel is provided so as to be fit to the traction wire 314 in a state of being compressed. FIG. 29 is a perspective view describing the internal configuration of the tip portion, wherein the turning unit base member 325 is omitted. As shown in FIG. 29, the spring 333 is provided on the inner portion of the turning unit base member 325 while in a state of being compressed.

As described above, a portion of the moveable gripping section 326 made of stainless steel, which is one of the gripping members, is fit into the tip portion side of the turning unit base member 325. The movable gripping section 326 is an approximately cylindrical shape having two oblong hole portions 326a and 326b, and the base end portion has a bottom portion as described above. On this bottom portion, an inner-facing flange portion is formed. The tip portion of the moveable gripping section 326 has a flange portion 326c. The tip side face of the flange portion 326c of the tip portion of the moveable gripping section 326 has a flat face portion for gripping a needle, and here this flat face of the flat face portion is orthogonal as to the axis of the approximately cylindrically-shaped moveable gripping section 326.

On the tip portion of the turning unit base member 325, a base end portion of the fixed gripping section 331 made of stainless steel, which is another gripping member, is fixed by a pin 330 made of stainless steel. The fixed gripping section 331 is a cylindrical member having a flange portion 331a on the tip portion. The fixed gripping section 331 and the turning unit base member 325 are fixed by the pin 330 which passes through the tip portion of the turning unit base member 325 and the base end portion of the fixed gripping section 331. The pin 330 is fitted into the two oblong holes 326a and 326b of the moveable gripping section 326 so as to be capable of sliding. The pin 330 is fixed to the turning unit base member 325 by laser welding on the end portions.

The fixed gripping section 331 which is the gripping section on the tip side is ring-shaped, and has a flat face portion which is parallel to the flat face portion of the tip portion of the moveable gripping section 326.

With the operating unit 303, when the opening/closing button 305 is not in operation, the spring 333 presses on the bottom portion of the moveable gripping section 326, but the tip side face of the flange portion 326c of the moveable gripping section 326 is in contact with the base end side face of the flange portion 331a of the fixed gripping section 331, and cannot expand any further, and so remains in a compressed state. Accordingly, when the opening/closing button 305 of the operating unit 303 is not in operation, the flat faces of the moveable gripping section 326 and fixed gripping section 331 are pressed so as to be in close contact and so the needle can be securely gripped. Also, when the opening/closing button 305 is pressed, the movable gripping section 326 moves towards the base end side from the fixed gripping section 331, and therefore the needle which is gripped between the flat faces of each of the moveable gripping section 326 and fixed gripping section 331 can be released, or the flat faces can be moved apart in order to grip a needle.

Also, the flange portion 331a of the fixed gripping section 331 and the flange portion 326c of the moveable gripping section 326 are formed thin, and so a needle can easily be placed in contact between the flat faces. Thus, regardless of the situation of the state of the body cavity wall or the bending angle of the gripping unit 308, the surgeon can easily grip a needle.

Accordingly, as will be described later, a needle is gripped so as to be nipped between the flat face portion of the fixed gripping section 331 and the flat face portion of the moveable gripping section 326 in accordance with opening/closing operations as to the opening/closing button 305. Accordingly, the spring 333 comprises a portion of the pressing member which constantly presses at least one of the two gripping members in the direction of coming into close contact with the other side.

The surfaces of each of the flat face portion of the fixed gripping section 331 and the flat face portion of the moveable gripping section 326, which are gripping faces which grip the needle, have been subjected to slip-resistant processing. Examples of slip-resistant processing include electrical discharge processing, knurling, spraying of diamond dust onto metal plating, and so forth.

Next, the operation of the treatment unit 304 of the needle driver 301 configured as above will be described.

As described above, the cylindrical portion of the base end side of the fixed gripping section 331 is inserted through the hole portion of the moveable gripping section 326, and the cylindrical portion is fixed to the turning unit base member 325, and so the fixed gripping section 331 has a fixed position relationship to the turning unit base member 325. In other words, the fixed gripping section 331 has a fixed position relationship in the long axis direction as to the bending base member 320.

On the other hand, when the opening operation of the opening/closing button 305 is performed, that is to say, when the opening/closing button 305 is pressed, the traction wire 314 is pulled according to the amount the button is pushed in, and thus the moveable gripping section 326 which is capable of moving towards the operating unit 303 side resists the force applied in the direction of the extension of the spring 333, and the moveable gripping section 326 moves towards the operating unit 303 side so that the flange portion 326c separates from the flange portion 331a of the fixed gripping section 331. Accordingly, when the traction wire 314 is pulled, the moveable gripping section 326 is moved in the direction shown by the arrow in FIG. 21, by the amount that the traction wire 314 is pulled. In other words, resisting the pressing force by the spring 333 in the direction of being in close contact with the fixed gripping section 331, the moveable gripping section 326 is moved in the direction of separating from the fixed gripping section 331 which is positioned on the tip portion of the treatment unit 304, by the opening operation of the opening/closing button 305. At this time, as shown in FIG. 23, the spring 333 is in a state of being compressed even further than in the state wherein the opening operation of the opening/closing button 305 is not performed as shown in FIG. 22, and force is applied to push back on the opening/closing button 305. When the opening operation is no longer performed, with the extension force of the spring 333 the traction wire 314 is pulled to the treatment unit 304 side, by the force in the direction whereby the moveable gripping section 326 comes into contact with the fixed gripping section 331. As a result, with the gripping unit 308, a needle is gripped in a position between the flat face of the fixed gripping section 331 and the flat face of the moveable gripping section 326.

Next the turning operation will be described. In a state wherein a needle is gripped, or in a state wherein a needle is not gripped, and the turning dial 307 is turned, the turning force transmitting pipe 313 which is a shaft member turns with the axis as the turning center, and therefore the turning force transmitting coil 317 which is fixed to the turning force transmitting pipe 313 turns, and the turning unit base member 325 which is fixed to the turning force transmitting coil 317 also turns. The turning force transmitting pipe 313 turns according to the amount that the turning dial 307 is turned, and therefore the turning amount according to amount that the turning dial 307 is turned is transmitted to the treatment unit 304. As a result, the fixed gripping section 331 and the moveable gripping section 326 which configure the gripping unit 308 turn along with the turning of the turning unit base member 325.

Also, at this time, the traction wire 314 is slidable as to the hole on the bottom portion of the turning unit base member 325, and therefore, even if the turning unit base member 325 turns, the traction wire 314 does not turn along with the turning unit base member 325.

Next, the angle-variable operation will be described. By moving the angle-variable lever 306 from the tip side of the insertion axis direction towards the base end side thereof, as shown in FIG. 28, the tip portion which includes the treatment unit 304 bends. When the angle-variable lever 306 is moved from the tip side of the insertion axis direction towards the base end side thereof, the bending force transmitting pipe 315 presses the joint member 318 to the tip side, and as a result, the joint member 318 pushes the linking member 319. The linking member 319 which has been pushed further pushes the bending unit base member 320, but because the bending unit base member 320 is linked to the tip housing member 312 with a pin 324, the bending unit base member 320 turns on the pin 324 as a turning center.

When the bending force transmitting pipe 315 advances or retreats according to the turning amount of the angle-variable lever 306, the bending amount of the treatment unit 304, that is to say, the bending angle changes. Thus, the surgeon can set the treatment unit 304 at a desired angle as to the axis of the insertion unit 302, according to the situation in surgery, and can perform treatment, as described above.

Figure 30:
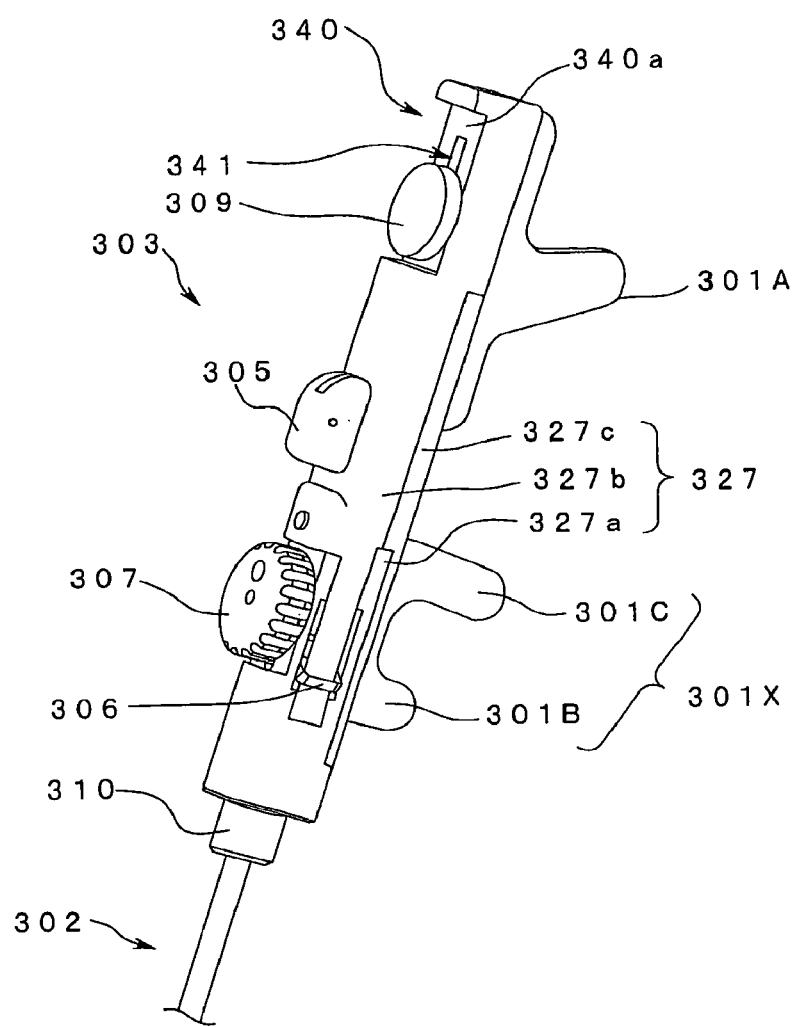
FIG. 30 is an external perspective view of the operating unit of a needle driver according to the third embodiment of the present invention, seen from one front diagonal side.
Figure 31:
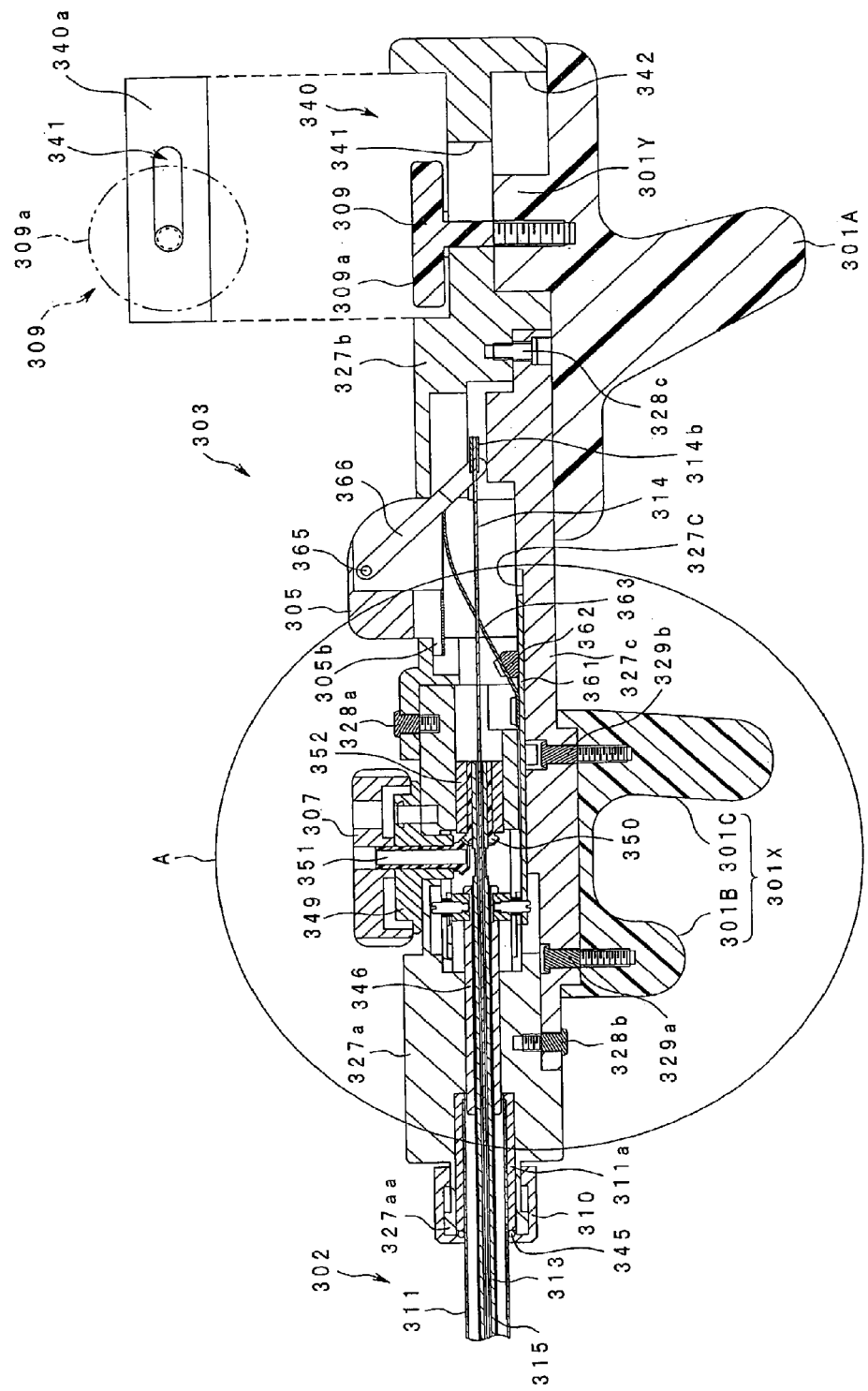
FIG. 31 is a cross-sectional view of the operating unit according to the third embodiment, along the axis direction of the needle driver.
Figure 32:
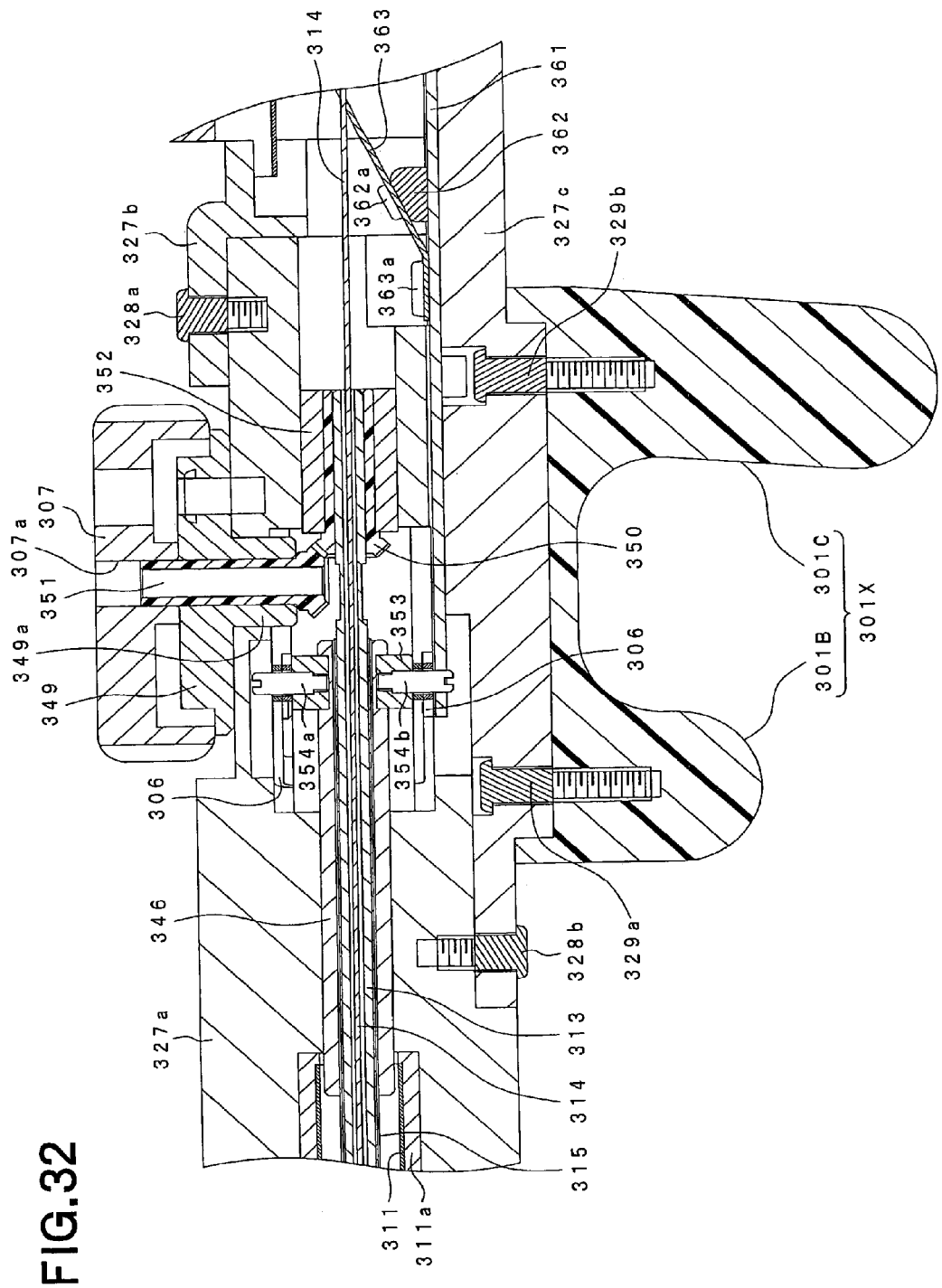
FIG. 32 is a cross-sectional view of the operating unit wherein the portion surrounded by the circle A in FIG. 17 has been enlarged.
Figure 33:
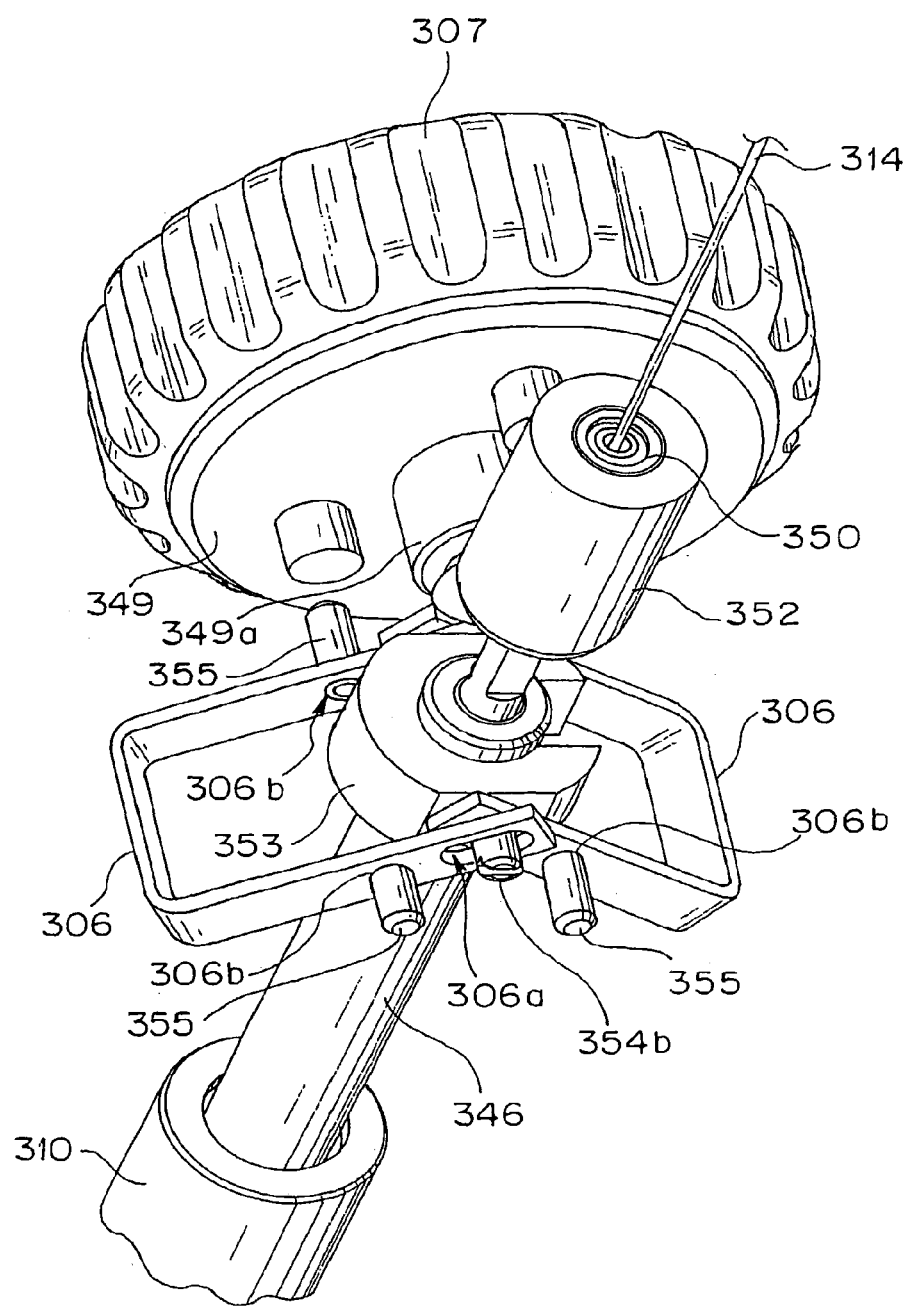
FIG. 33 is a perspective view showing the internal configuration of the operating unit provided in the periphery of the turning dial, wherein the exterior member of the operating unit of the third embodiment is omitted.
Figure 34:
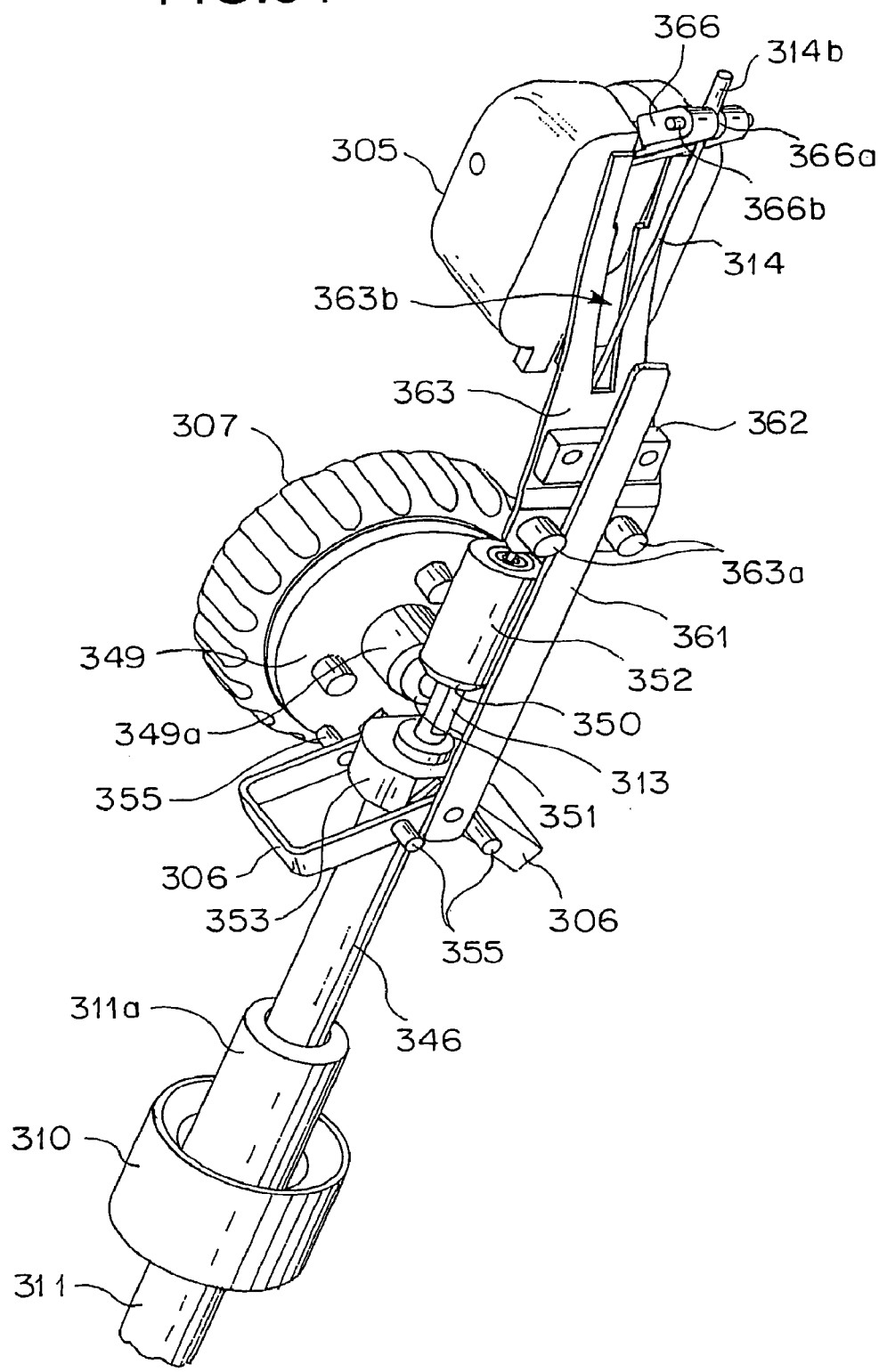
FIG. 34 is a perspective view of the various configuration members within the operating unit of the third embodiment, seen from a lower diagonal side.
Figure 35:
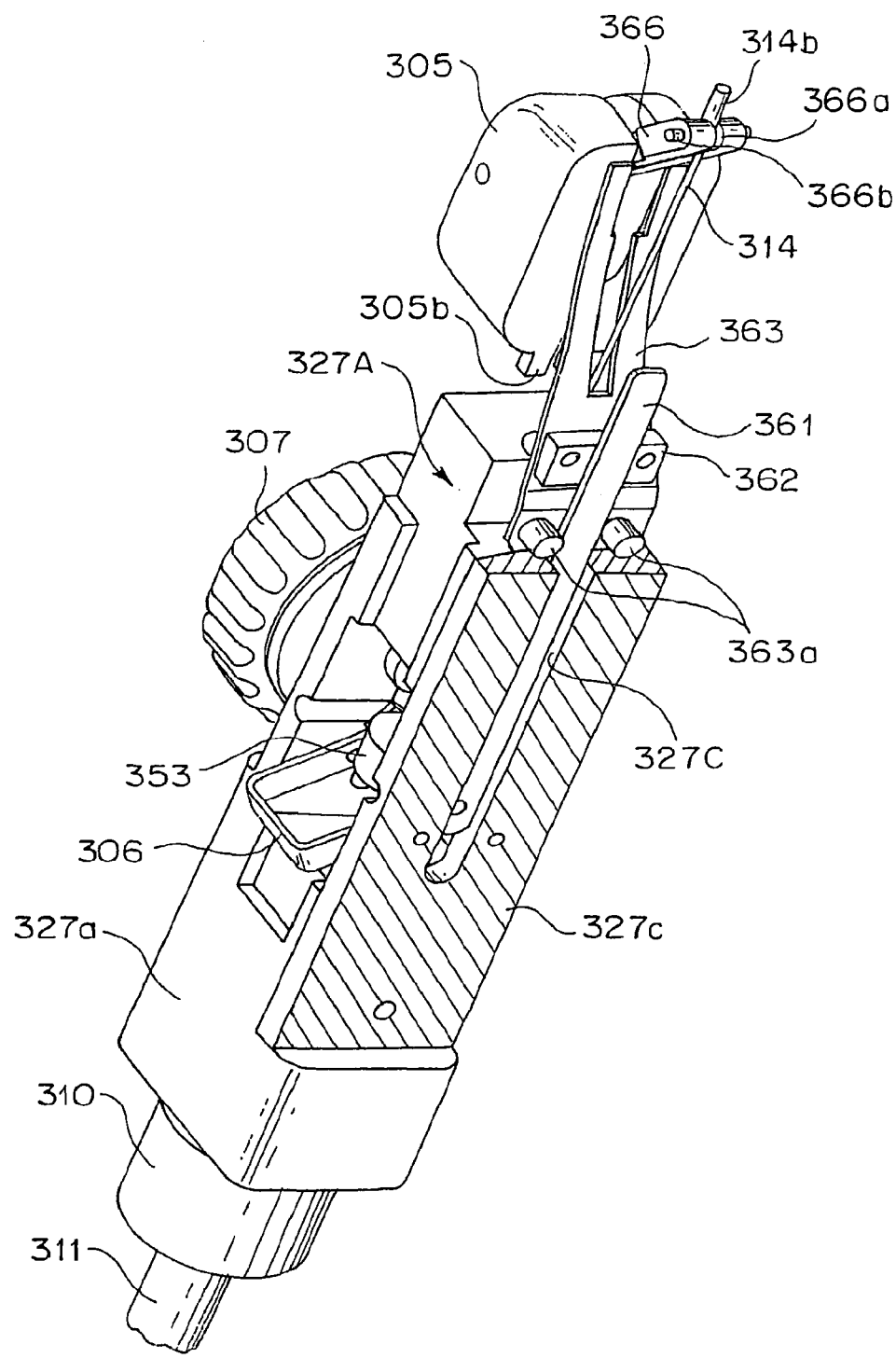
FIG. 35 is a perspective view of a portion of the exterior member of the operating unit of the third embodiment, wherein the various configuration members within the operating unit are seen from a lower diagonal side.
Figure 36:
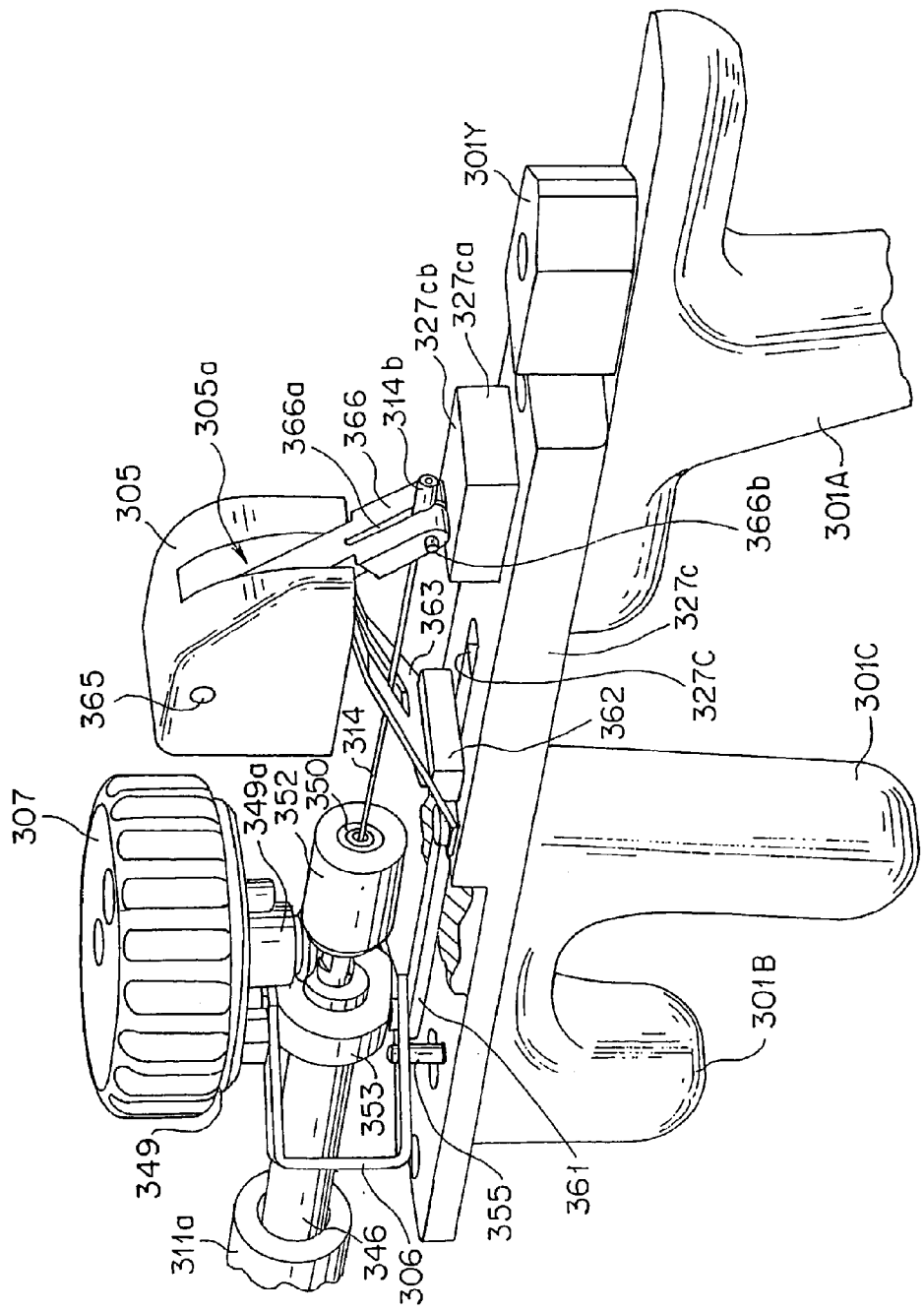
FIG. 36 is a perspective view of a portion of the exterior member of the operating unit of the third embodiment, wherein the various configuration members within the operating unit are seen from a diagonal side on the base end side.
Figure 37:
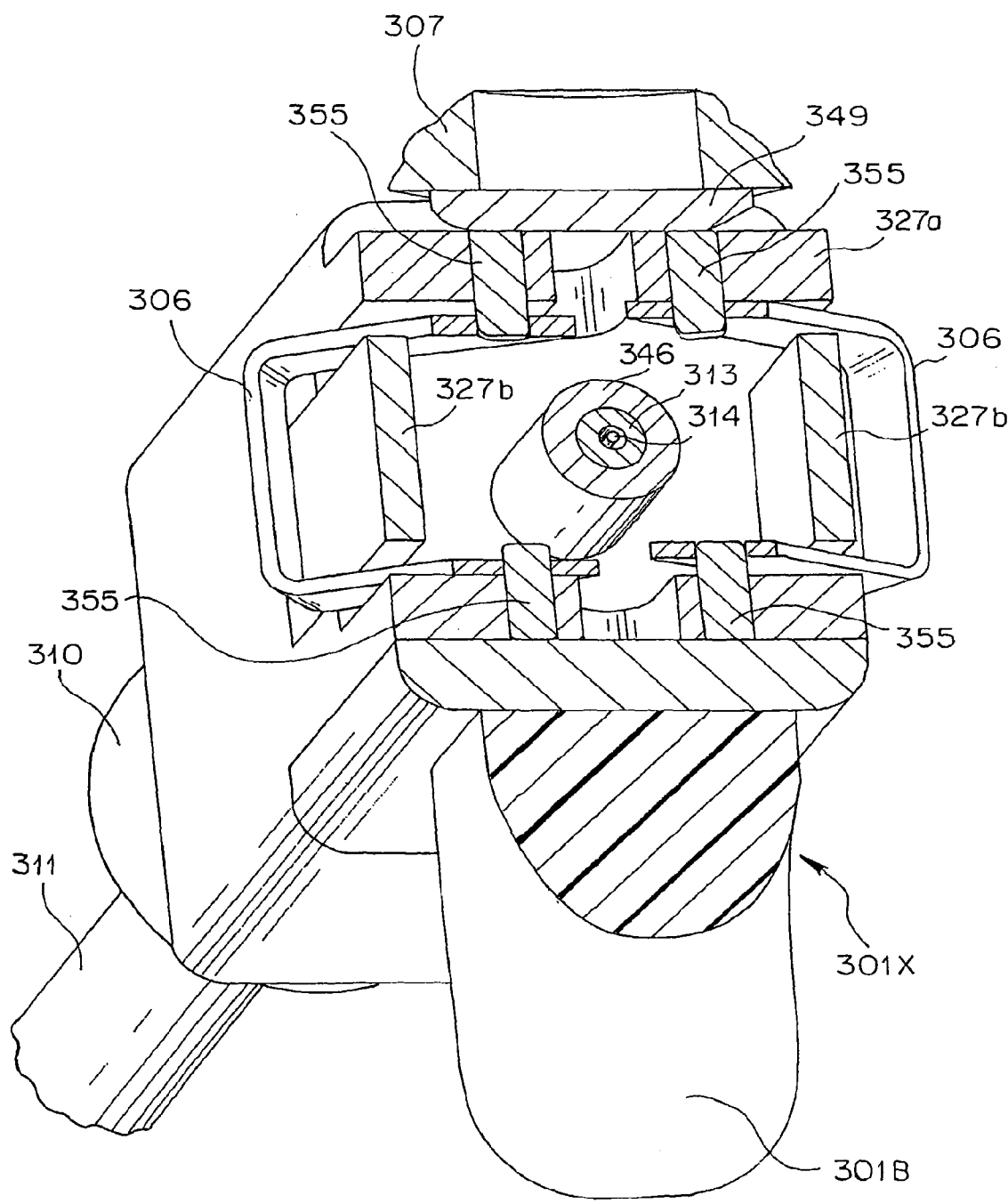
FIG. 37 is a cross-sectional view wherein a mid-section of the operating unit has been cut along the direction which is orthogonal as to the axis of the needle driver of the third embodiment.
Figure 38:
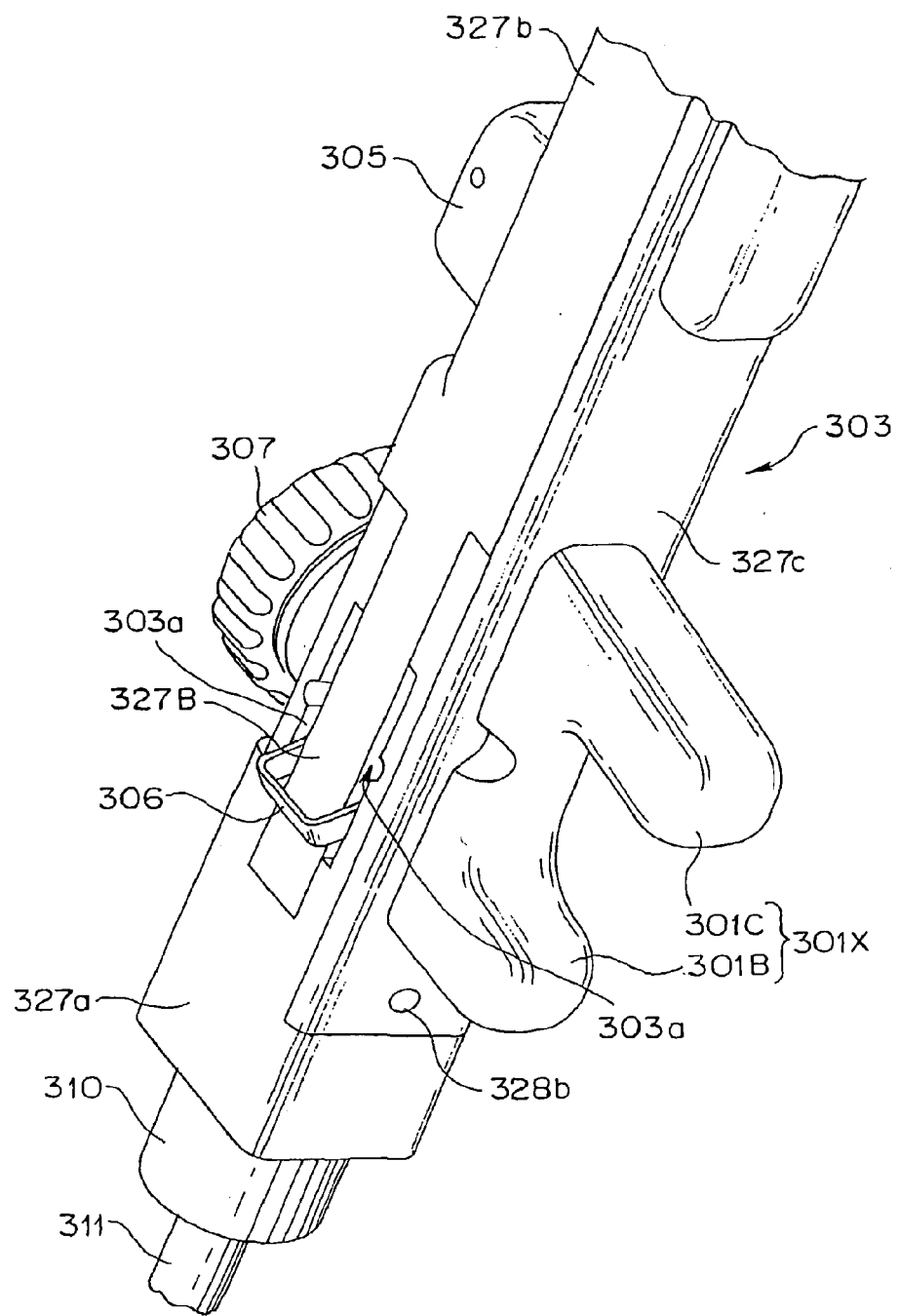
FIG. 38 is a perspective view of the operating unit of the third embodiment seen from a side face directional side.
Figure 39:
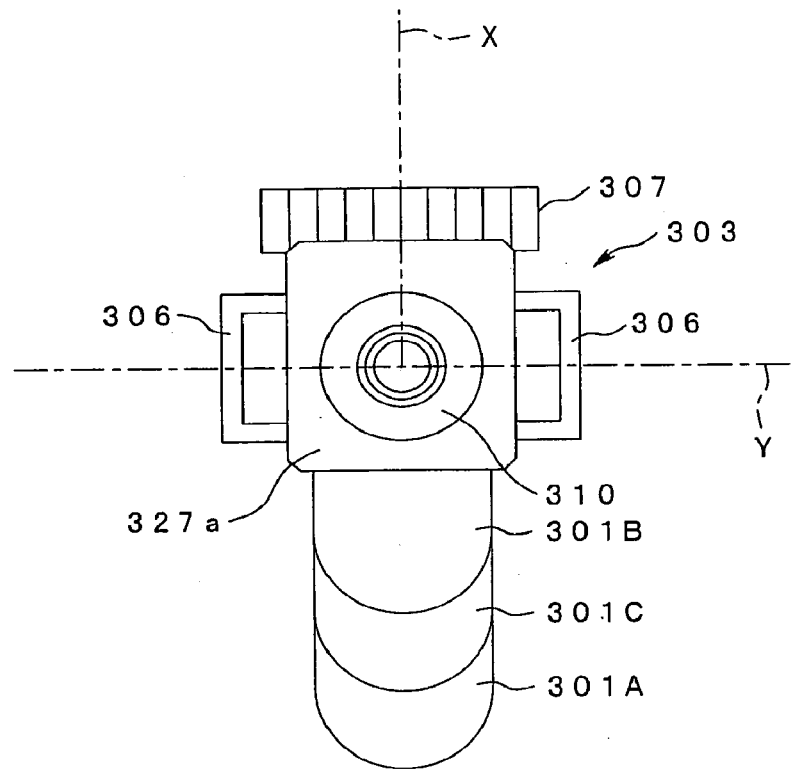
FIG. 39 is a front view of the needle driver of the third embodiment, seen from the tip side.

Next, the operating unit 303 of the needle driver 301 according to the present embodiment will be described with reference to FIGS. 30 through 39. FIG. 30 is an external perspective view of the operating unit 303 of the needle driver 301, seen from one front diagonal side, FIG. 31 is a cross-sectional view of the operating unit 303, along the axis direction of the needle driver 301, FIG. 32 is a cross-sectional view of the operating unit 303 wherein the portion surrounded by the circle A in FIG. 17 is enlarged, FIG. 33 is a perspective view showing the internal configuration of the operating unit 303 provided in the periphery of the turning dial 307, wherein the exterior member of the operating unit 303 is omitted, FIG. 34 is a perspective view of the various configuration members within the operating unit 303, seen from a lower diagonal side, FIG. 35 is a perspective view of a portion of the exterior member of the operating unit 303, wherein the various configuration members within the operating unit 303 are seen from a lower diagonal side, FIG. 36 is a perspective view of a portion of the exterior member of the operating unit 303, wherein the various configuration members within the operating unit 303 are seen from a diagonal side on the base end side, FIG. 37 is a cross-sectional view wherein a mid-section of the operating unit 303 is cut along the direction which is orthogonal as to the axis of the needle driver 301, FIG. 38 is a perspective view of the operating unit 303 seen from a side face directional side, and FIG. 39 is a front view of the needle driver 301, seen from the tip side.

As shown in FIG. 30, the operating unit 303 is arranged on the same axis as the long axis of the insertion unit 2 on the base end side of the insertion unit 302, and is covered by an exterior member 327 which has an approximately rectangular shape. This exterior member 327 is configured as one unit with three metal members fitting together, which are made of aluminum or the like, and comprises a tip side exterior member 327a for forming the exterior of the tip side (the insertion unit 302 side), a main unit exterior member 327b on which the turning dial 307 and an opening/closing button 305 is arranged on one face thereof, and a cover exterior member 327c on which a finger holding member 301X is arranged on one face, and which is fit together on the opposite side from the face on which the turning dial 307 and the opening/closing button 305 of the main unit exterior member 327b are provided.

The tip side exterior member 327a and the main unit exterior member 327b are fixed with a fixing screw 328a. Also, after the finger holding member 301X is fixed to one face of the cover exterior member 327c with two fixing screws 329a and 329b, the cover exterior member 327c is fixed to the tip side exterior member 327a with a fixing screw 328b, and is fixed to the main unit exterior member 327b with a fixing screw 328c. The exterior member 327 can be made of resin.

A hole portion is formed on the inner side of the tip side exterior member 327a for the space in which a mechanism in the periphery of a thruster 353 to be described later and the angle-variable lever 306 are arranged, and on both sides a concave-shaped step portion 327A is formed from the base end to the mid-section towards the tip side (see FIG. 35. It should be noted that FIG. 35 only shows the step portion 327A on one side face side of the tip side exterior member 327a).

The main unit exterior member 327b has two arm units 327B (see FIG. 38, it should be noted that FIG. 38 only shows the arm units 327B on one side face side of the main unit exterior member 327b), which extend toward the tip side, on both side portions of the tip side, and these two arm units 327B are each fitted in two step portions 327A of the tip side exterior member 327a.

Also, in the state wherein the main unit exterior member 327b comes in close contact with the tip side exterior member 327a, on the portions to be both side faces of the operating unit 303, the angle-variable lever 306 can protrude from each side face, and also a long groove 303a is formed thereupon for the purpose of a pivoting operation (see FIG. 38). There are two such long groove 303a formed on one side face of the operating unit 303.

As shown in FIG. 31, a step portion 340 is formed on the base end portion of the main unit exterior member 327b. This step portion 340 has a seat portion 340a which is in contact with the dial head portion 309a of an adjusting dial 309 which is made of resin. An oblong hole 341 is formed along the long axis direction of the operating unit 303 in the approximate center of the step portion 340 on the seat portion 340a. The protruding portion 301Y of the palm resting member 301A enters the surface of the main unit exterior member 327b on the opposite side of the step portion 340, and a groove portion 342 is formed along the long axis direction of the operating unit 303. The oblong hole 341 is a hole for communicating the step portion 340 and the groove portion 342.

The adjusting dial 309 is inserted from the step portion 340 side, and a screw portion of the adjusting dial 309 is screwed into a female screw hole formed in the protruding portion 301Y, the palm resting member 301A is fixed to the adjusting dial 309 by being screwed in, and the palm resting member 301A is fixed to the main exterior member 327b. At the time of the fixing, the position of the adjusting dial 309 in the oblong hole 341, in the long axis direction of the main unit exterior member 327b, can be adjusted, and thus the position of the palm resting member 301A in the long axis direction of the main unit exterior member 327b can be adjusted to the hand size of the surgeon.

The dial head portion 309a of the adjusting dial 309 has an outer diameter that is longer than the length of the width direction of the operating member 303, so as to protrude from both side faces of the operating unit 303, for the purpose of being able to more easily grip the outer circumference portion.

Also, the tip side exterior member 327a has a cylindrical linking portion 327aa which is formed so as to protrude on the tip side. A hole portion which connects to the opening portion of the tip side of the cylindrical linking unit 327aa is formed on the tip side exterior member 327a. This hole portion has a step portion partway down on the base end side from the tip side. A screw groove is cut into the circumferential face of the linking unit 327aa.

A holding ring 310 which is an approximately ring shape having a screw groove cut into the inner surface is provided so as to cover the linking unit 327aa. The holding ring 310 made of aluminum has an opening portion on the tip side. The base end portion of the sheath 311 of the insertion unit 302 is inserted into the tip side exterior member 327a so as to pass through the opening portion of the holding ring 310 and the opening portion of the linking portion 327aa, and also, the holding ring 310 is fixed to the linking portion 327aa by screwing together the screw groove on the inner surface and the screw groove on the circumferential face of the linking portion 327aa.

To describe in detail, the sheath 311 has an approximately cylindrical sheath end member 311a in close contact with the outside of the base end portion, and is inserted into the hole portion of the tip side exterior member 327a along with the sheath end member 311a, to be capable of sliding and turning about the axis of the sheath end member 311a. The sheath end member 311a is made of aluminum. Also, the face to be the tip side of the holding ring 310 has a hole portion (opening portion) formed, wherein the hole diameter is approximately the same as the outer diameter of the sheath 311. In other words, the face on the tip side of the holding ring 310 forms the inner-facing flange, and by the sheath end members 311a of the sheath 311 making contact with the inner-facing flange, the sheath 311 which forms the exterior of the insertion unit 302 does not pull out from the tip side exterior member 327a.

The holding ring 310 moves toward the base end side, as the amount being screwed into the linking unit 327aa increases. An O-ring 345 made of silicon is provided between the holding ring 310 and the sheath end member 311a. Thus, the inner-facing flange face of the holding ring 310 presses the sheath end member 311a of the sheath 311 toward the base end side, via the O-ring 345.

Then, the sheath end member 311a which is fixed to the base end portion of the sheath 311 has the base end face thereof in contact with the tip face of the step portion formed on the hole portion of the tip side exterior member 327a, with the elasticity of the O-ring 345. As a result, the insertion unit 302 is securely fixed to the operating unit 303 without wobbling.

Further, the O-ring 345 presses on the sheath end member 311a with a predetermined pressure, to the extent that the insertion unit 302 is securely fixed to the operating unit 303, and the insertion unit 302 can turn about the axis of the insertion unit 302 as to the operating unit 303. This is realized by setting the distance for the O-ring 345 to be compressed and to generate such a predetermined pressure, wherein such distance is between the tip inner surface of the holding ring 310 and the sheath end member 311a, when the tip inner face of the holding ring 310 makes contact with the tip portion of the linking unit 327aa.

The turning force transmitting pipe 313 through which the traction wire 314 is inserted has a passive side bevel gear member 350 made of synthetic resin such as polyacetal adhered and fixed on the base portion. The turning force transmitting pipe 313 is pressed and fixed in the hole portion formed on the length direction of the passive side bevel gear member 350, so that the turning axis of the passive side bevel gear member 350 overlaps with the cross-sectional center in the orthogonal direction to the length direction axis of the turning force transmitting pipe 313.

The end portion having a gear of this passive side bevel gear member 350 faces the tip side, and the axis portion is supported on an approximately cylindrical bearing 352 so as to turn about the axis. The bearing 352 which is made of aluminum or resin is inserted and fixed into the tip side exterior member 327a.

Also, a turning dial 307 is arranged on the step portion which is formed on one face of the tip side exterior member 327a. A bearing plate 349 in an approximately disc shape is provided on the face of the operating unit 303 side of the turning dial 307 which is made of aluminum or resin. This bearing plate 349 is fixed to the tip side exterior member 327a. A wheel axis 349a protrudes from the center portion of the face on the opposite side from the face of the turning dial 307 side of the bearing plate 349 made of aluminum or resin. The bearing plate 349 has a hole portion formed, which passes through the axis center of the wheel axis 349a from the center of the face on the turning dial 307 side.

This hole portion in the bearing plate 349 has an active bevel gear member 351 made of a synthetic resin such as polyacetal, which is inserted through so as to be capable of turning about the axis of the active side bevel gear 351. Also, the end portion on the opposite side from the side which has the gear on the active side bevel gear member 351 is fitted into a portion of the hole portion 307a formed on the turning axis center of the turning dial 307, and is fixed thereupon. In other words, the turning dial 307 and the active side bevel gear member 351 are one unit.

Also, the bearing plate 349 is provided so that the teeth of the active side bevel gear member 351 mesh with the teeth of the passive side bevel gear member 350.

Accordingly, when the turning dial 307 is turned in a predetermined direction by the surgeon, the turning is transmitted to the active side bevel gear member 351, and by the teeth action, the turning force is transmitted to the passive side bevel gear member 350. In other words, when the turning dial 307 is operated to turn about the axis which is orthogonal to the length direction of the operating unit 303, the turning force is transmitted about the axis in the length direction to the turning force transmitting pipe 313 with the passive side bevel gear member 350, via the active side bevel gear member 351. As a result, the turning force transmitting pipe 313 transmits the turning force to the turning force transmitting coil 317 (see FIG. 9) which is fixed to the tip of the turning force transmitting pipe 313, and the gripping unit 308 (see FIG. 1) turns.

The bearing plate 349 also functions as a protection plate for preventing deterioration by attrition between the turning dial 307 and the tip side exterior member 327a, from friction which is generated by the turning and so forth. Also, the outer circumference portion of the turning dial 307 protrudes further than both side faces of the operating unit 303, as described above. Therefore, there may be a case wherein force is applied to pull out the turning dial 307 from the end portion on the opposite side from the side having the bear of the active side bevel gear member 351, due to handling by the surgeon or nurse. As a measure against this, a bearing plate 349 is provided on the side face of the turning dial 307, and prevents a force great enough to pull out the turning dial 307 from the active side bevel gear member 351.

In other words, the bearing plate 349 has an outer diameter which is slightly smaller than that of the turning dial 307. Thus, the operability of the turning dial 307 for the surgeon to directly operate the turning with the index finger is not lost, and the direction of pulling out, that is to say, the direction separated from the tip side exterior member 327a is prevented from having a great force applied.

As shown in FIG. 32, the bending force transmitting pipe 315 through which the turning force transmitting pipe 313 is inserted so as to be capable of turning on the long axis has an approximately cylindrical fixing pipe 346 adhered thereto so as to be slidable in the long axis direction as to the tip side exterior member 327a of the base end portion. This fixing pipe 346 which is made of aluminum is moved so as to advance or retreat in the long axis direction, along with the bending force transmitting pipe 315, by the operation of the angle-variable lever 306.

Also, as shown in FIGS. 32 and 33, a thruster 353 made of a metal such as stainless steel is solidly fit to the base end portion of the fixing pipe 346. This thruster 353 has two screw holes cut from the circumferential face side on the same axis, and screw pins 354a and 354b which are each made of a metal such as stainless steel are screwed into these two screw holes.

Specifically, the thruster 353 is cut so that the portions on both ends of the outer side of the approximately cylindrically shaped member has parallel faces, and two screw holes are formed from each of these cut faces toward the inner side, in the direction orthogonal as to the cut faces. Also, the screw pins 354a and 354b are each screwed into the two screw holes so as to have a raised end portion of each of the screw pins 354a and 354b.

The two hole portions into which the screw pins 354a and 354b are screwed in are formed on the thruster 353 so as to have each hole axis on the same axis. In other words, in the position wherein the two screw pins 354a and 354b have each of the long axes along the same axis, and become symmetric on the portions on both ends on the outer side of the thruster 353, each is raised toward the circumferential direction of the thruster 353. These two screw pins 354a and 354b respectively have a groove formed on the screw head so as to be screwed in with a flat-head screwdriver.

Also, on the thruster 353, a notch is formed which is orthogonal to the axis of the two screw pins 354a and 354b and which faces the center from the outer circumference portion on one direction side which is orthogonal to the long axis of the fixing pipe 346. The notched portion of the thruster 353 has two facing parallel flat faces.

The fixing pipe 346 has an external groove formed on the exterior of the base end portion, and the external groove is formed with a shaping processing to have a groove face corresponding to the parallel two flat faces on the portions notched on the thruster 353. Thus, the thruster 353 is fitted to the external groove of the fixing pipe 346 from the circumferential direction of the notched portion so that the two faces of the notched portion and the groove face of the external groove of the fixing pipe 346 come into contact.

Thus, the thruster 353 is fit to the fixing pipe 346 so that the axes of the two screw pins 354a and 354b are orthogonal to the long axis of the fixing pipe 346.

The angle-variable lever 306 is a member which has a metal plate member in a sideways U-shape on which an oblong hole 306a is cut open on both end portions. On the two arm units of the sideways U-shaped angle-variable lever 306, a hole portion 306b (see FIG. 33) is cut open, into which a pivot pin 355 to be described later is inserted near each of the oblong holes 306a. That is to say, the angle-variable lever 306 is provided with two oblong holes 306a and two hole portions 306b.

Also, the angle-variable lever 306 has the position of each of the oblong holes 306a and each of the hole portions 306b determined on a portion having a face which faces the sideways U-shaped arm unit, so that the center of each of the two oblong holes 306a pass through the same axis, and the center of the two hole portions 306b pass through the same axis, and holes opened therein. Further, the position for each of the oblong holes 306a and each of the hole portions 306b is determined so as to have the axis passing through each of the centers thereof be orthogonal as to the above-mentioned facing face. Two of the above-described angle-variable levers 306 are arranged on the needle driver 301 according to the present embodiment so as to protrude from both side faces of the operating unit 303, as shown in FIG. 39.

The two screw pins 354a and 354b of the thruster 353 are inserted into each of the oblong holes 306a of the two angle-variable levers 306 so as to be capable of sliding and turning about the axis of the screw pins 354a and 354b, as shown in FIG. 33. Also, the two angle-variable levers 306 are arranged so as to sandwich the thruster 353 and have the long axis of the fixing pipe 346 become symmetric as to the long axis of the two screw pins 354a and 354b.

The arm units of these two angle-variable levers 306 overlap so as to be staggered near the screw pins 354a and 354b in the state of being provided on the thruster 353. In other words, in the case wherein the portion of the one angle-variable lever 306 has the screw pin 354a inserted into the oblong hole 306a on the thruster 353 side, the other angle-variable lever 306 has the screw pin 354b inserted into the oblong hole 306a on the thruster 353 side.

Also, pivot pins 355 are inserted from the outside face direction into each of the hole portions 306b of the two angle-variable levers 306. That is to say, with the present embodiment, one pivot pin 355 is inserted into each of the two hole portions 306b of one angle-variable lever 306 so as to be capable of sliding and turning about the axis of each pivot pin 355, and therefore, with an operating unit 303 which has two angle-variable levers 306 provided thereupon, a total of four pivot pins 355 are provided.

These four pivot pins 355 are each pressed and fixed into the tip side exterior members 327a (see FIG. 37). Also, the two pivot pins 355 which are inserted into the two hole portions 306b of one angle-variable lever 306 are each pressed and fixed so as to face the tip side exterior member 327a so that the long axes of each are on the same axis. Accordingly, the two angle-variable levers 306 can freely turn on the axes of each of the pivot pins 355 corresponding to each hole portion 306b.

With the above configuration, the two angle-variable levers 306 operate by turning about the axis of the pivot pins 355, and thus can move the fixing pipe 346 to advance or retreat in the long axis direction, via the thruster 353. Thus, the bending force transmitting pipe 315 is linked to the advancing or retreating movement of the fixing pipe 346, and advances or retreats in the long axis direction.

Then along with the advancing or retreating movement of the bending force transmitting pipe 315 in the long axis direction, the joint member 318 provided on the tip portion of the bending force transmitting pipe 315 pushes the linking member 319 toward the tip side or pulls it toward the base end side. Also, by the linking member 319 pushing the bending unit base member 320 toward the tip side or pulling towards the base end side, the bending unit base member 320 turns with the pin 324 as the turning center. Thus, the treatment unit 304 can perform bending operation within a range of 90 degrees as to the axis of the insertion unit 302.

Also, as shown in FIG. 39, when the needle driver 301 of the present embodiment is seen from the tip side, the two angle-variable levers 306 are provided so as to protrude from both side faces of the operating unit 303. To describe in detail, each center portion of the two sideways U-shaped angle-variable levers 306 protrudes in the direction orthogonal as to the vertical axis X, and also, in the direction separated from the operating unit 303, in the horizontal axis Y direction from both side faces of the operating unit 303 which intersect with the horizontal axis Y which passes through the center of the operating unit 303. The vertical axis X links the turning dial 307 provided on the upper side as seen on paper in FIG. 39 of the operating unit 303, and the palm resting member 301A and finger holding members 301B and 301C provided on the lower side as seen on paper in FIG. 39 of the operating unit 303, and also, passes through the center of the operating unit 303.

Thus, by operating one of the angle-variable levers 306, the surgeon can perform a bending operation of the treatment unit 304 in the range of 90 degrees as to the axis of the insertion unit 302. Thus, the needle driver 301 of the present embodiment provides one angle-variable lever 306 on both side faces of the operating unit 303 and therefore the treatment unit 304 can be easily bent as to the axis of the insertion unit 302, regardless of the dominant hand of the surgeon (right-handed or left-handed).

The mechanism in the periphery of the thruster 353 which is fit to the fixing pipe 346 and on which two angle-variable levers 306 are provided is arranged in the internal space formed by the tip side exterior member 327a, the main unit exterior member 327b, and the cover exterior member 327c.

Also, as shown in FIG. 34, a brake bar 361 made of a metal plate such as stainless steel is provided at one screw pin 354b on the thruster 353 such that one end portion of the brake bar 361 is overlapped with the portion having the oblong hole 306a of the two angle-variable levers 306, and on the other end portion of the brake bar 361 extends toward the base end side. On the one end portion described above of this brake bar, a hole portion is formed, and the screw pin 354b is inserted into the hole portion.

The brake bar 361 is guided straight ahead by being provided in the groove portion 327C which is formed on one face of the cover exterior member 327c which is on the inner side of the operating unit 303, and the mid-section thereof is sandwiched so as to apply a predetermined amount of friction force on the tip side exterior member 327a and the cover exterior member 327c. With this friction force, a certain amount of turning force is necessary when the angle-variable lever 306 is turned. Thus, the surgeon can maintain the treatment unit 304 in a bent state at a predetermined angle as to the axis of the insertion unit 302, by operating the angle-variable lever 306.

The groove portion 327C is formed on the tip side exterior member 327a so as to have the length in the same long axis direction approximately as the advancing or retreating amount of the bending force transmitting pipe 315 and the fixing pipe 346 which moves in the long axis direction by turning of the two angle-variable levers 306.

Also, on the above-described mid-section of one face of the cover exterior member 327c, one end portion of the plate spring 363 which presses the opening/closing button 305 in one direction is fixed with two pins 363a. Also, the brake bar 361 is, as shown in FIG. 34, inserted between the plate spring 363 and the cover exterior member 327c and between the two pins 363a which fix the plate spring 363, and is held so that the entire body is buried in the groove portion 327C of the cover exterior member 327c.

The stainless steel plate spring 363 has a notch 363b formed in an approximately rectangular shape from the base end to the mid-section, and the base end portion which is to become the other end portion is in contact with the back face on the base end side of the opening/closing button 305. A traction wire 314 is inserted through the notch portion 363b of the plate spring 363. A wire retaining member 314b which is made of stainless steel is provided on the base end portion of the traction wire 314.

A brake shoe 362 made of a metal such as stainless steel is provided on the mid-section of the plate spring 363 on the face side facing the cover exterior member 327c and the brake bar 361. When the opening/closing button 305 is pressed in toward the inner side of the operating unit 303, this brake shoe 362 is pushed toward the brake bar 361 side according to the movement force toward the cover exterior member 327c side received by the plate spring 363. Thus, the pressure on both end faces, which each are in contact with the groove portion of the cover exterior member 327c and the brake shoe 362, increases on the brake bar 361, and receives a great friction force. Accordingly, the brake bar 361 is regulated so as not to be able to move in the long axis direction.

As a result, by regulating the movement of the brake bar 361, the angle-variable lever 306 cannot be turned, and the thruster 353, fixing pipe 346, and bending force transmitting pipe 315 also cannot advance or retreat in the long axis direction, and when the opening/closing button 305 is pushed in toward the inner side of the operating unit 303, the state of the treatment unit 304 being bent at a predetermined angle as to the axis of the insertion unit 302 can be maintained with certainty.

Also, as shown in FIG. 36, the opening/closing button 305 is an approximately square column block unit made of resin or a metal such as aluminum, and has a guide groove 305a formed with a notch, from the base end portion to the face on which one end portion of the plate spring 363 makes contact. One end portion of a pull link 366 which is made of metal is inserted into the guide groove 305a of the opening/closing button 305. Also, a pin 365 which maintains the turning of the pull link 366 is provided to the opening/closing button 305 in the direction orthogonal to the axis direction of the guide groove 305a. Also, as shown in FIG. 31, the opening/closing button 305 has two protruding portions 305b which protrude on the tip side toward the tip portion of the face side on which one end portion of the plate spring 363 is in contact.

The opening/closing button 305 is fit into the hole portion provided on the main unit exterior member 327b from the face side of the main unit exterior member 327b which is on the inner side of the operating unit 303. At this time, the opening/closing button 305 is prevented from being pulled out of the operating unit 303 by having the two protruding portions 305b being in contact with one face of the main unit exterior member 327b.

Also, the opening/closing button 305 is moveable so as to advance or retreat in the direction orthogonal to the long axis of the operating unit 303 within the interior space of the operating unit 303 which is formed with the main unit exterior member 327b and the cover exterior member 327c, and normally, is pressed in the outer surface direction of the main unit exterior member 327b by the plate spring 363 as described above, that is to say, so that the two protruding portions 305b are in contact with one face of the main unit exterior member 327b.

The pull link 366 one end portion of which is supported on the opening/closing button 305 by the pin 365 so as to be capable of turning has a groove 366a formed on the other end portion, and this groove 366a grips the wire retaining member 314b for the traction wire 314. Also, the other end portion of the pull link 366 has a pin 366b provided for retaining the traction wire 314 in the groove 366a.

As shown in FIG. 36, the cover exterior member 327c has a guide protrusion 327ca which protrudes from the face of the base end portion on the side forming the inner space of the operating unit 303. This guide protrusion 327ca has a flat face portion 327cb on the protruding side, and the above-described other end portion of the pull link 366 is in contact with this flat face portion 327cb.

The pull link 366 which is turned by the surgeon pressing the opening/closing button 305 is directly guided along the flat face portion 327cb of the guide protrusion 327ca, and the above-described other end portion slides toward the base end side on the face of the flat face portion 327cb. At this time, the traction wire 314 is pulled toward the base end side along the long axis without much slipping.

Thus, the amount of protruding of the guide protrusion 327ca of the cover exterior member 327c, the length of the pull link 366, and the arrangement position of the wire retaining member 314b of the traction wire 314 which the above-described other end portion of the pull link 366 grips is set so as to each corresponds to the tightening or loosening of the traction wire 314 to the base end side or the tip side without slipping, with the button operation of the opening/closing button 305.

Thus, the opening/closing button 305 is pushed in towards the inner side of the operating unit 303 by the surgeon, and with the linked pull link 366, when the traction wire 314 is pulled toward the base end side along the long axis direction, the enlarged end portion 314a on the traction wire 314 moves the moveable gripping section 326 (see FIG. 28) which is fixed on the inner side of the bottom portion toward the base end side. Thus, the tip side face of the flange portion 326c of the moveable gripping section 326 moves away from the base end side face of the flange portion 331a of the fixed gripping section 331.

Also, when the pushing in of the opening/closing button 305 toward the inner side of the operating unit 303 by the surgeon is released, the opening/closing button 305 receives pressing force from the plate spring 363, and moves toward the outer side of the operating unit 303. At this time, the spring 333 in the turning unit base member 325 presses on the bottom portion of the moveable gripping section 326, and extends until the tip side face of the flange portion 326c of the moveable gripping section 326 makes contact with the base end side face of the flange portion 331a of the fixed gripping section 331. Accordingly, when the opening/closing button 305 of the operating unit 303 is not operated, the flat faces of each of the moveable gripping section 326 and the fixed gripping section 331 are pressed so as to be in close contact.

As a result of the above, by the operation or non-operation of the pressing in of the opening/closing button 305, the movable gripping section 326 moves from the fixed gripping section 331 towards the base end side, and so the flat faces can be moved apart to release a needle which is gripped between the flat faces of each of the moveable gripping section 326 and the fixed gripping section 331, or to grip a needle.

Also, when the opening/closing button 305 is pressed and the traction wire 314 is pulled toward the base end, a force is generated in which the traction wire 314 forms a straight line by the extension force. Thus, when the opening/closing button 305 is pressed in a state wherein the treatment unit 304 is bent at a predetermined angle as to the axis of the insertion unit 302, the traction wire 314 receives a force which causes it to form a straight line, and the predetermined angle, at which the treatment unit 304 which has the traction wire 314 inserted therein is bent as to the insertion unit 302, cannot be maintained. Thus, the surgeon cannot keep the desired bent state of the treatment unit 304 as to the insertion unit 302, and therefore suturing becomes difficult.

Thus, when the opening/closing button 305 is pressed, the brake shoe 362 pushes the brake bar 361, and because movement is regulated, the needle driver 301 of the present embodiment is configured so that the state of the treatment unit 304 being bent at a predetermined angle as to the insertion unit 302 can be maintained with certainty. As a result, the surgeon can keep the desired bent state of the treatment unit 304 as to the insertion unit 302, and therefore suturing becomes easier.

As described above, the end portions having gear teeth of the passive side bevel gear member 350 face the tip side. Also, the insertion unit 302 can be turned about the axis of the insertion unit 302 as to the operating unit 303. Accordingly, when the surgeon sees the operating unit 303 from the side of the turning dial 307, when the extension direction of the treatment unit 304 as to the insertion axis of the insertion unit 302 is the same as the direction of the eye of the surgeon who sees this, the turning direction of the turning dial 307 (that is to say, clockwise or counter-clockwise as seen by the surgeon) becomes the same direction as the turning direction of the treatment unit 304. Also, when the insertion unit 302 is turned about the axis of the insertion unit 302 as to the operating unit 303, and the surgeon views the operating unit 303 from the side of the turning dial 307, and when the extension direction of the treatment unit 304 as to the insertion axis of the insertion unit 302 is the same as the line of sight of the surgeon, the turning direction of the turning dial 307 becomes the opposite direction as the turning direction of the treatment unit 304.

At the time of suturing, a needle driver 301 and a forceps are often used. In such a case, when the surgeon sees the operating unit 303 from the side of the turning dial 307, the extension direction of the treatment unit 304 as to the insertion axis of the insertion unit 302 is the same direction as the eye of the surgeon who sees this, and therefore the turning operation of the treatment unit 304 of the needle driver 301 has good operability.

Figure 40:
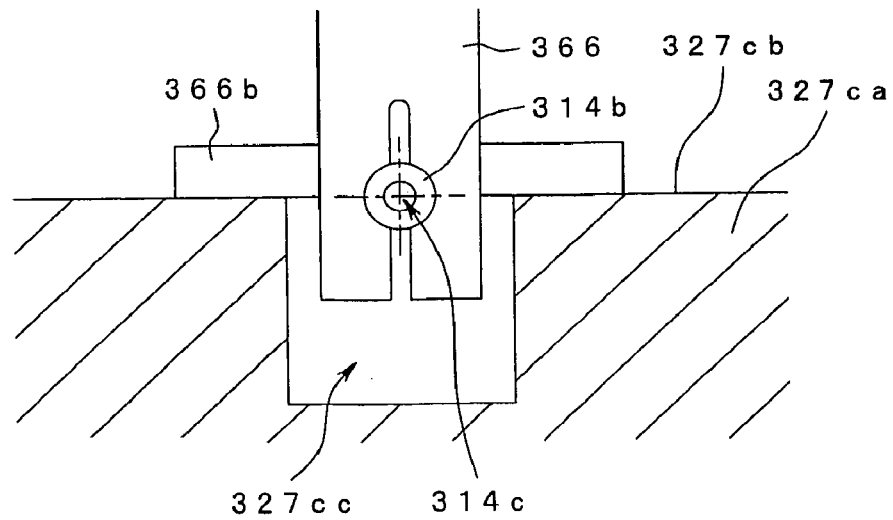
FIG. 40 is a diagram to describe another configuration for pulling a traction wire straight towards the base end side.

In order for the traction wire 314 to be pulled straight toward the base end side, the pull link 366 is configured to make contact with the flat face 327cb of the guide protrusion 327ca, but can have a configuration such as that in FIG. 40. FIG. 40 is a diagram to describe another configuration for pulling the traction wire 314 straight towards the base end side, and is a diagram seen from the base end side of the traction wire 314 wherein the pull link 366 and the guide protrusion 327ca are in contact with one another. As shown in FIG. 40, the pin 366b provided on the pull link 366 is in contact with the flat face portion 327cb of the guide protrusion 327ca. A groove portion 327cc is formed on the guide protrusion 327ca, along the axis direction of the operating unit 303, and one end of the pull link 366 is inside the groove portion 327cc. The axis center 314c of the traction wire 314 is positioned on the flat face of the flat face portion 327cb, in a state wherein the pin 366b is in contact with the flat face portion 327cb. Accordingly, when the opening/closing button 305 is pressed, one end of the pull link 366 moves along the groove portion 327cc, and the traction wire 314 is pulled toward the base end side. At this time, the traction wire 314 is pulled toward the base end side, while the axis center 314c of the traction wire 314 is constantly positioned on the flat face of the flat face portion 327cb. Accordingly, the traction wire 314 is pulled straight toward the base end side.

Thus, according to the needle driver 301 relating to the present embodiment, with the operating unit 303, when opening/closing operations, turning operations, and angle-changing operations of the extension direction of the gripping unit 308 on the treatment unit 304 are performed, the three shaft members arranged on the same axis transmit the opening/closing force, turning force, and angle-variable force, respectively, to the treatment unit 304. Specifically, the three shaft members arranged on the same axis transmit the opening/closing force, turning force, and angle-variable force corresponding to the operations linked to each of the opening/closing button 305 as an opening/closing operating member on the operating unit 303, the turning dial 307 as a turning operating member, and the angle-variable lever 306 as an angle-changing operating member to the treatment unit 304.

Further, the three shaft members described above are positioned on the inner side of the sheath 311 which is a shaft member in a pipe shape, and the sheath 311 also can turn about the axis as to the operating unit 303. Thus, the sheath 311 on the insertion unit 302 is also on the same axis as the three shaft members, and can turn about the axis of the insertion unit 302 as to the operating unit 303. Accordingly, not only can the surgeon perform opening/closing operations of the treatment unit 304, turning operations, and angle-changing operations in the extension direction, but can also change the extension direction of the treatment unit 304, since the sheath 311 can be turned about the axis.

Therefore, according to each of the needle drivers relating to the above-described present embodiments, a surgical instrument can be realized which has good operability for tissue anastomosis with an endoscope, and has an insertion unit with a smaller diameter. The operability is better, and so tissue anastomosis with an endoscope becomes easier, and the surgery quality is improved, the duration of surgery can be shortened, and because the diameter is smaller, the surgery is less invasive, and the patient can be discharged from the hospital sooner and return to society sooner.

According to the present embodiment, a surgical instrument can be realized which has good operability for tissue anastomosis with an endoscope, and has an insertion unit with a smaller diameter.

The present invention should not be limited to the above-described embodiments, and various changes and modifications can be made within the scope of the present invention.

What is claimed is:

1. A surgical instrument comprising:
an insertion unit;
an operating unit provided on one end of the insertion unit;
a treatment unit provided so as to protrude from the other end of the insertion unit;
a first shaft member for transmitting turning force to the treatment unit in conjunction with the turning operation of a turning operation member provided on the operating unit;
a second shaft member for transmitting opening/closing force to the treatment unit in conjunction with the opening/closing operation of an opening/closing member provided on the operating unit; and
a third shaft member for transmitting angle-variable force which changes the angle in the protruding direction of the treatment unit as to the axis of the insertion unit in conjunction with an angle-variable operation of a angle-variable operating unit provided on the operating unit;
wherein the first shaft member, the second shaft member, and the third shaft member are positioned on approximately the same axis, the first shaft member, second shaft member and third shaft member extend from a distal end of the insertion unit to the operating unit;
and wherein the treatment unit can turn about the axis in the protruding direction according to the turning operation with the turning operation member, and the treatment unit can move at least one of two gripping members, each having a gripping face according to the opening/closing operation with the opening/closing operation member, and so can be opened or closed, and the treatment unit can change the angle in the protruding direction according to the angle-variable operation with the angle-variable operating unit and wherein the first and third shaft members are each in a pipe shape, and the second shaft member is in a rod shape, wherein the second shaft member is inserted within the first shaft member, and the first shaft member is inserted within the third shaft member.

2. The surgical instrument of claim 1, wherein the first shaft member only transmits a turning force, the second shaft member only transmits an opening/closing force and the third shaft member only transmits an angle-variable force.

3. A surgical instrument comprising:
an insertion unit;
an operating unit provided on one end of the insertion unit;
a treatment unit provided so as to protrude from the other end of the insertion unit;
a first shaft member for transmitting turning force to the treatment unit in conjunction with the turning operation of a turning operation member provided on the operating unit;
a second shaft member for transmitting opening/closing force to the treatment unit in conjunction with the opening/closing operation of an opening/closing member provided on the operating unit; and
a third shaft member for transmitting angle-variable force which changes the angle in the protruding direction of the treatment unit as to the axis of the insertion unit in conjunction with an angle-variable operation of a angle-variable operating unit provided on the operating unit;
wherein the first shaft member, the second shaft member, and the third shaft member are positioned on approximately the same axis, the first shaft member, second shaft member and third shaft member extend from a distal end of the insertion unit to the operating unit;
wherein the treatment unit can turn about the axis in the protruding direction according to the turning operation with the turning operation member, and the treatment unit can move at least one of two gripping members, each having a gripping face according to the opening/closing operation with the opening/closing operation member, and so can be opened or closed, and the treatment unit can change the angle in the protruding direction according to the angle-variable operation with the angle-variable operating unit, and
wherein the treatment unit further comprises two gripping members and a biasing member which biases at least one of the two gripping members in the direction which is constantly in contact with the other gripping member, and the one gripping member resists the biasing force of the biasing member by the opening operation of the opening/closing operation, and thus moves in the direction which separates it from the other gripping member.

4. The surgical instrument according to claim 3, wherein the first and third shaft members are each in a pipe shape, and the second shaft member is in a rod shape, wherein the second shaft member is inserted within the first shaft member, and the first shaft member is inserted within the third shaft member.

5. The surgical instrument according to claim 4, wherein the insertion unit has a fourth shaft member in a pipe shape, and the third shaft member is inserted within the fourth shaft member.

6. A surgical instrument comprising:
an insertion unit;
an operating unit provided on one end of the insertion unit;
a treatment unit provided so as to protrude from the other end of the insertion unit;
first shaft means for transmitting turning force to the treatment unit in conjunction with the turning operation of a turning operation means provided on the operating unit;
second shaft means for transmitting opening/closing force to the treatment unit in conjunction with the opening/closing operation of opening/closing means provided on the operating unit; and
third shaft means for transmitting angle-variable force which changes the angle in the protruding direction of the treatment unit as to the axis of the insertion unit in conjunction with an angle-variable operation of a angle-variable operating means provided on the operating unit;
wherein the first shaft means, the second shaft means, and the third shaft means are positioned on approximately the same axis, the first shaft means, second shaft means and third shaft means extend from a distal end of the insertion unit to the operating unit;
and wherein the treatment unit can turn about the axis in the protruding direction according to the turning operation with the turning operation means, and the treatment unit can move at least one of two gripping members, each having a gripping face according to the opening/closing operation with the opening/closing operation means, and so can be opened or closed, and the treatment unit can change the angle in the protruding direction according to the angle-variable operation with the angle-variable operating unit and wherein the first and third shaft means are each in a pipe shape, and the second shaft means is in a rod shape, wherein the second shaft means is inserted within the first shaft means, and the first shaft means is inserted within the third shaft means.

7. The surgical instrument of claim 6, wherein the first shaft means only transmits a turning force, the second shaft means only transmits an opening/closing force and the third shaft means only transmits an angle-variable force.

8. A surgical instrument comprising:
an insertion unit;
an operating unit provided on one end of the insertion unit;
a treatment unit provided so as to protrude from the other end of the insertion unit;
first shaft means for transmitting turning force to the treatment unit in conjunction with the turning operation of a turning operation means provided on the operating unit;
second shaft means for transmitting opening/closing force to the treatment unit in conjunction with the opening/closing operation of opening/closing means provided on the operating unit; and
third shaft means for transmitting angle-variable force which changes the angle in the protruding direction of the treatment unit as to the axis of the insertion unit in conjunction with an angle-variable operation of a angle-variable operating means provided on the operating unit;
wherein the first shaft means the second shaft means and the third shaft means are positioned on approximately the same axis, the first shaft means, second shaft means and third shaft means extend from a distal end of the insertion unit to the operating unit;
wherein the treatment unit can turn about the axis in the protruding direction according to the turning operation with the turning operation means, and the treatment unit can move at least one of two gripping members, each having a gripping face according to the opening/closing operation with the opening/closing operation means, and so can be opened or closed, and the treatment unit can change the angle in the protruding direction according to the angle-variable operation with the angle-variable operating unit, and
wherein the treatment unit further comprises two gripping members and biasing means which biases at least one of the two gripping members in the direction which is constantly in contact with the other gripping member, and the one gripping member resists the biasing force of the biasing means by the opening operation of the opening/closing operation, and thus moves in the direction which separates it from the other gripping member.

9. The surgical instrument according to claim 8, wherein the first and third shaft means are each in a pipe shape, and the second shaft means is in a rod shape, wherein the second shaft means is inserted within the first shaft means, and the first shaft means is inserted within the third shaft means.

10. The surgical instrument according to claim 9, wherein the insertion unit has fourth shaft means in a pipe shape, and the third shaft means is inserted within the fourth shaft means.

11. A surgical instrument comprising:
an insertion unit;
an operating unit provided on one end of the insertion unit;
a treatment unit provided so as to protrude from the other end of the insertion unit;
first operation means provided on the operating unit for turning the treatment unit about an axis in the protruding direction according to the turning operation;
second operation means provided on the operating unit to open or close the treatment unit by moving at least one of two gripping members thereof in response to an opening/closing operation;
third operation means provided on the operating unit for changing the angle in the protruding direction of the treatment unit as to the axis of the insertion unit in response to an angle-variable operation;
first shaft means in a pipe shape for transmitting a first force to turn the treatment unit in conjunction with the turning operation input from the first operation means;
second shaft means inserted within the first shaft means for transmitting a second force to open or close the treatment unit in conjunction with the opening/closing operation input from the second operation means; and
third shaft means in a pipe shape which is provided in the insertion unit and within which the first shaft means is inserted, for transmitting a third force to change the angle in conjunction with an angle-variable operation input from the third operation means, wherein the first shaft means, second shaft means and third shaft means extend from a distal end of the insertion unit to the operating unit.

12. The surgical instrument of claim 11, wherein the first shaft means only transmits a turning force, the second shaft means only transmits an opening/closing force and the third shaft means only transmits an angle-variable force.

* * * * *

UNITED STATES PATENT AND TRADEMARK OFFICE
CERTIFICATE OF CORRECTION

PATENT NO.       : 7,972,345 B2
APPLICATION NO.  : 11/599543
DATED            : July 5, 2011
INVENTOR(S)      : Manabu Miyamoto et al.

It is certified that error appears in the above-identified patent and that said Letters Patent is hereby corrected as shown below:

IN THE CLAIMS:

Column 37, line 29 (claim 8) should read: wherein the first shaft means, the second shaft means, and Signed and Sealed this
Eleventh Day of October, 2011

David J. Kappos
*Director of the United States Patent and Trademark Office*